United States Patent
Xiong et al.

(10) Patent No.: US 10,851,112 B2
(45) Date of Patent: Dec. 1, 2020

(54) ANTI-HCMV VIRUS COMPOUND

(71) Applicant: MEDSHINE DISCOVERY INC., Jiangsu (CN)

(72) Inventors: Jian Xiong, Shanghai (CN); Jingjing Wang, Shanghai (CN); Wentao Wu, Shanghai (CN); Haizhong Tan, Shanghai (CN); Xuanjia Peng, Shanghai (CN); Yang Zhang, Shanghai (CN); Kevin X. Chen, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 16/323,074

(22) PCT Filed: Aug. 8, 2017

(86) PCT No.: PCT/CN2017/096366
§ 371 (c)(1),
(2) Date: Feb. 4, 2019

(87) PCT Pub. No.: WO2018/028556
PCT Pub. Date: Feb. 15, 2018

(65) Prior Publication Data
US 2019/0202838 A1 Jul. 4, 2019

(30) Foreign Application Priority Data

Aug. 8, 2016 (CN) .......................... 2016 1 0644091

(51) Int. Cl.
*C07D 495/04* (2006.01)
*A61P 31/22* (2006.01)
*A61K 31/519* (2006.01)

(52) U.S. Cl.
CPC .......... *C07D 495/04* (2013.01); *A61K 31/519* (2013.01); *A61P 31/22* (2018.01)

(58) Field of Classification Search
CPC .................................................. C07D 495/04
See application file for complete search history.

(56) References Cited

U.S. PATENT DOCUMENTS

| 2005/0065160 A1 | 3/2005 | Wunberg et al. |
| 2008/0132515 A1 | 6/2008 | Wunberg et al. |

FOREIGN PATENT DOCUMENTS

| WO | WO-2004096778 A1 | 11/2004 |
| WO | WO-2005113552 A1 | 12/2005 |
| WO | WO-2016109360 A1 | 7/2016 |

OTHER PUBLICATIONS

International Search Report and Written Opinion of PCT/CN2017/096366 dated Oct. 20, 2017.
Extended European Search Report issued in European patent application No. 17838686.8 dated May 27, 2019.
Berge S. M. et al., "Pharmaceutical salts", Journal of Pharmaceutical Sciences, vol. 66, No. 1, 1977, p. 1-19.
Quintela J. M. et al., "A novel synthesis of dihydropyrimidothienopyridazine derivatives", Tetrahedron, Elsevier Science Publishers, Amsterdam, NL, vol. 54, No. 28, 1998, p. 8107-8122.
Remington, The Science and Practice of Pharmacy, 21st Ed, Lippincott, Williams & Wilkins, 2005.

*Primary Examiner* — Brian E McDowell
(74) *Attorney, Agent, or Firm* — Harness, Dickey & Pierce, P.L.C.

(57) ABSTRACT

Disclosed are a class of fused cyclic compounds against the HCMV virus, and use thereof in the preparation of a drugs for treating diseases associated with the HCMV virus. In particular, disclosed is the compound shown in formula (II) and pharmaceutically acceptable salts thereof.

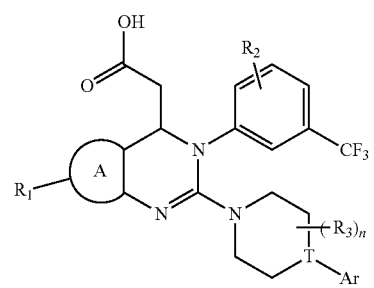

(II)

25 Claims, No Drawings

ANTI-HCMV VIRUS COMPOUND

CROSS REFERENCE TO RELATED APPLICATIONS

This application is a 371 National Phase of PCT/CN2017/096366 filed Aug. 8, 2017, which claims the benefit of Chinese Patent Application No. CN201610644091.1, filed on Aug. 8, 2016. The entire disclosures of the above applications are incorporated herein by reference.

FIELD OF THE INVENTION

The present invention relates to a class of fused cyclic compounds against HCMV virus, a use thereof in manufacturing a medicament for treating a disease associated with HCMV virus. Specifically, the present invention relates to a compound represented by formula (I) or formula (II) and a pharmaceutically acceptable salt thereof.

BACKGROUND OF THE INVENTION

Human cytomegalovirus (HCMV) is one of the eight species human herpesviruses with a worldwide distribution and a high clinical finding. Despite the advance in diagnosis and treatment, human cytomegalovirus infections still have significant complications in clinical conditions associated with pregnancy and immunocompromised like organ or bone marrow transplants, cancer and AIDS. Currently approved antiviral drugs include ganciclovir (GCV) and its prodrug valganciclovir (VGCV), foscavir (FOS) and cidofovir (CDV), which are all viral DNA polymerase inhibitors. Although these drugs are effective, their use are limited by severe toxic side effects, low oral bioavailability (except VGCV) and drug resistance. Ganciclovir has limited efficacy against cytomegalovirus and toxicity. Foscavir and cidofovir are the most common alternatives, but both have nephrotoxicity. Mutations in viral DNA polymerase targeted by these agents may lead to drug resistance, therefore there is still a largely unsatisfied need in the clinic. Novel and safer anti-human cytomegalovirus drugs are urgently needed.

WO2004096778 discloses compound A:

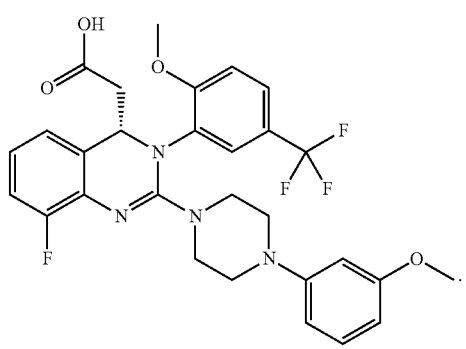

CONTENT OF THE INVENTION

The present invention provides a compound represented by formula (II), a pharmaceutically acceptable salt or a tautomer thereof,

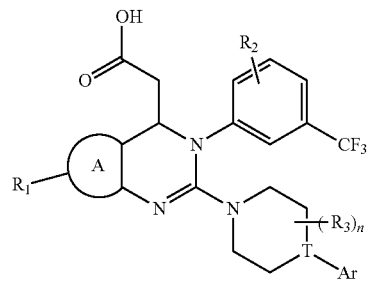

wherein, ring A is a 5-membered heteroaromatic ring;

$R_1$ is H or halogen, or selected from the group consisting of $C_{1-6}$ alkyl and $C_{1-6}$ heteroalkyl, each of which is optionally substituted by 1, 2 or 3 R;

$R_2$ is H, or $C_{1-6}$ alkoxy which is optionally substituted by 1, 2 or 3 R;

$R_3$ is H, or selected from the group consisting of $C_{1-6}$ alkyl and $C_{1-6}$ heteroalkyl, each of which is optionally substituted by 1, 2 or 3 R;

T is N or C(R);

n is 1 or 2;

Ar is selected from the group consisting of phenyl and 6-membered heteroaryl, each of which is optionally substituted by 1, 2 or 3 R;

R is H, F, Cl, Br, I, OH, CN, $NH_2$, or $C(=O)NH_2$, or selected from the group consisting of $C_{1-6}$ alkyl and $C_{1-6}$ heteroalkyl, each of which is optionally substituted by 1, 2 or 3 R';

R' is F, Cl, Br, I, OH, CN, $NH_2$, COOH, Me, Et, $CF_3$, $CHF_2$, $CH_2F$, $NHCH_3$ or $N(CH_3)_2$;

the heteroatom or heteroatom group in the 5-membered heteroaromatic ring, 6-membered heteroaryl or $C_{1-6}$ heteroalkyl is selected from the group consisting of —C(=O)NH—, —NH—, —S(=O)$_2$NH—, —S(=O)NH, —O—, —S—, N, —C(=O)O—, —C(=O)—, —S(=O)— and —S(=O)$_2$—;

in any of the above cases, the number of the heteroatom or the heteroatom group is independently 1, 2 or 3.

The present invention provides a compound represented by formula (I), a pharmaceutically acceptable salt or a tautomer thereof,

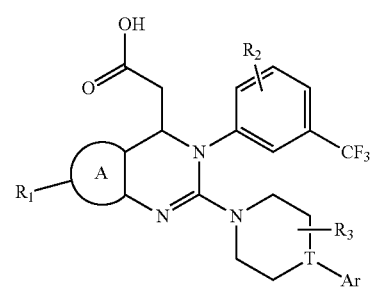

wherein, ring A is a 5-membered heteroaromatic ring;

$R_1$ is H or halogen, or selected from the group consisting of $C_{1-6}$ alkyl and $C_{1-6}$ heteroalkyl, each of which is optionally substituted by 1, 2 or 3 R;

$R_2$ is H or $C_{1-6}$ alkoxy which is optionally substituted by 1, 2 or 3 R;

$R_3$ is H, or selected from the group consisting of $C_{1-6}$ alkyl and $C_{1-6}$ heteroalkyl, each of which is optionally substituted by 1, 2 or 3 R;

T is N or C(R);

Ar is selected from the group consisting of phenyl and 6-membered heteroaryl, each of which is optionally substituted by 1, 2 or 3 R;

R is H, F, Cl, Br, I, OH, CN, $NH_2$, C(=O)$NH_2$, or selected from the group consisting of $C_{1-6}$ alkyl and $C_{1-6}$ heteroalkyl, each of which is optionally substituted by 1, 2 or 3 R';

R' is F, Cl, Br, I, OH, CN, $NH_2$, COOH, Me, Et, $CF_3$, $CHF_2$, $CH_2F$, $NHCH_3$ or N($CH_3$)$_2$;

the heteroatom or heteroatom group in the 5-membered heteroaromatic ring, 6-membered heteroaryl or $C_{1-6}$ heteroalkyl is selected from the group consisting of —C(=O)NH—, —NH—, —S(=O)$_2$NH—, —S(=O)NH, —O—, —S—, N, —C(=O)O—, —C(=O)—, —S(=O)— and —S(=O)$_2$—;

in any of the above cases, the number of the heteroatom or the heteroatom group is independently 1, 2 or 3.

In some embodiments of the present invention, R is H, F, Cl, Br, I, OH, CN, $NH_2$, or C(=O)$NH_2$, or selected from the group consisting of $C_{1-3}$ alkyl, ($C_{1-3}$ alkyl)-O—, ($C_{1-3}$ alkyl)-S—, ($C_{1-3}$ alkyl)-NH— and N,N'-di($C_{1-3}$ alkyl) amino, each of which is optionally substituted by 1, 2 or 3 R'.

In some embodiments of the present invention, R is H, F, Cl, Br, I, OH, CN, $NH_2$, C(=O)$NH_2$, Me, Et,

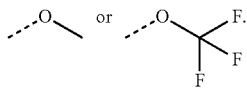

In some embodiments of the present invention, ring A is thienyl, furyl, oxazolyl, isothiazolyl or isoxazolyl.

In some embodiments of the present invention, the moiety

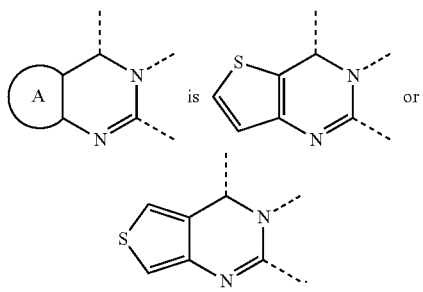

In some embodiments of the present invention, $R_1$ is H, F, Cl, Br or I, or selected from the group consisting of $C_{1-3}$ alkyl, ($C_{1-3}$ alkyl)-O— and ($C_{1-3}$ alkyl)-S—, each of which is optionally substituted by 1, 2 or 3 R.

In some embodiments of the present invention, $R_1$ is H, F, Cl, Br or I, or selected from the group consisting of Me and Et, each of which is optionally substituted by 1, 2 or 3 R.

In some embodiments of the present invention, $R_1$ is H, F, Cl, Br, I, Me or Et.

In some embodiments of the present invention, $R_2$ is H or ($C_{1-3}$ alkyl)-O— which is optionally substituted by 1, 2 or 3 R.

In some embodiments of the present invention, $R_2$ is H or

which is optionally substituted by 1, 2 or 3 R.

In some embodiments of the present invention, $R_2$ is H,

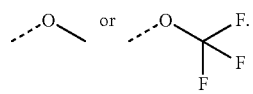

In some embodiments of the present invention, $R_3$ is H, or selected from the group consisting of $C_{1-3}$ alkyl, ($C_{1-3}$ alkyl)-O— and ($C_{1-3}$ alkyl)-S—, each of which is optionally substituted by 1, 2 or 3 R.

In some embodiments of the present invention, $R_3$ is H, or selected from the group consisting of Me, Et and

each of which is optionally substituted by 1, 2 or 3 R.

In some embodiments of the present invention, $R_3$ is H, Me, Et, $CF_3$,

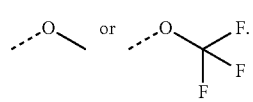

In some embodiments of the present invention, T is N, CH, C(F), C(Cl), C(Br) or C(I).

In some embodiments of the present invention, Ar is selected from the group consisting of phenyl, pyridyl, pyrimidinyl, pyrazinyl and pyridazinyl, each of which is optionally substituted by 1, 2 or 3 R.

In some embodiments of the present invention, Ar is selected from the group consisting of

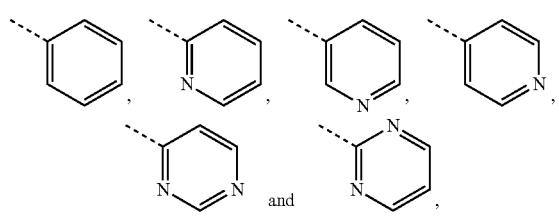

each of which is optionally substituted by 1, 2 or 3 R.

In some embodiments of the present invention, Ar is

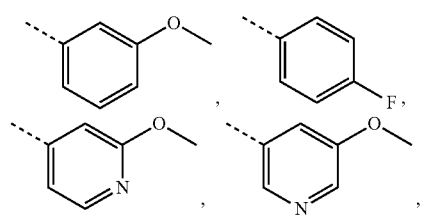

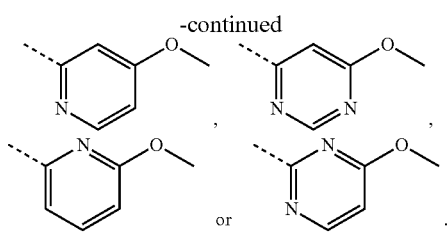

In some embodiments of the present invention, the moiety

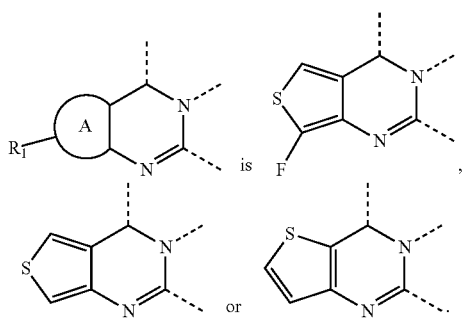

In some embodiments of the present invention, R is H, F, Cl, Br, I, OH, CN, NH$_2$ or C(=O)NH$_2$, or selected from the group consisting of C$_{1-3}$ alkyl, (C$_{1-3}$ alkyl)-O—, (C$_{1-3}$ alkyl)-S—, (C$_{1-3}$ alkyl)-NH— and N,N'-di(C$_{1-3}$ alkyl) amino, each of which is optionally substituted by 1, 2 or 3 R', wherein R' is as defined by the present invention.

In some embodiments of the present invention, R is H, F, Cl, Br, I, OH, CN, NH$_2$, C(=O)NH$_2$, Me, Et,

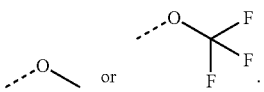

In some embodiments of the present invention, ring A is thienyl, furyl, oxazolyl, isothiazolyl or isoxazolyl.

In some embodiments of the present invention, the moiety

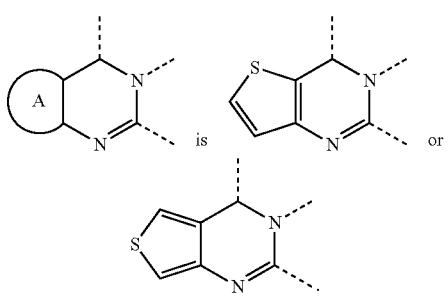

In some embodiments of the present invention, R$_1$ is H, F, Cl, Br or I, or selected from the group consisting of C$_{1-3}$ alkyl, (C$_{1-3}$ alkyl)-O— and (C$_{1-3}$ alkyl)-S—, each of which is optionally substituted by 1, 2 or 3 R, wherein R is as defined by the present invention.

In some embodiments of the present invention, R$_1$ is H, F, Cl, Br or I, or selected from the group consisting of Me and Et, each of which is optionally substituted by 1, 2 or 3 R, wherein R is as defined by the present invention.

In some embodiments of the present invention, R$_1$ is H, F, Cl, Br, I, Me or Et.

In some embodiments of the present invention, R$_2$ is H or (C$_{1-3}$ alkyl)-O— which is optionally substituted by 1, 2 or 3 R, wherein R is as defined by the present invention.

In some embodiments of the present invention, R$_2$ is H or

which is optionally substituted by 1, 2 or 3 R, wherein R is as defined by the present invention.

In some embodiments of the present invention, R$_2$ is H,

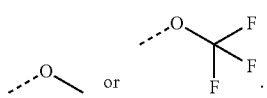

In some embodiments of the present invention, R$_3$ is H or selected from the group consisting of C$_{1-3}$ alkyl, (C$_{1-3}$ alkyl)-O— and (C$_{1-3}$ alkyl)-S—, each of which is optionally substituted by 1, 2 or 3 R, wherein R is as defined by the present invention.

In some embodiments of the present invention, R$_3$ is H, or selected from the group consisting of Me, Et and

each of which is optionally substituted by 1, 2 or 3 R, wherein R is as defined by the present invention.

In some embodiments of the present invention, R$_3$ is H, Me, Et, CF$_3$,

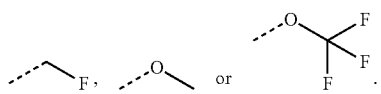

In some embodiments of the present invention, T is N, CH, C(F), C(Cl), C(Br) or C(I).

In some embodiments of the present invention, Ar is selected from the group consisting of phenyl, pyridyl, pyrimidinyl, pyrazinyl and pyridazinyl, each of which is optionally substituted by 1, 2 or 3 R, wherein R is as defined by the present invention.

In some embodiments of the present invention, Ar is selected from the group consisting of

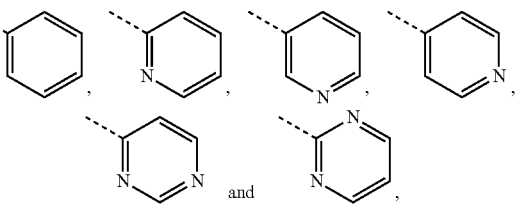

each of which is optionally substituted by 1, 2 or 3 R, wherein R is as defined by the present invention.

In some embodiments of the present invention, Ar is selected from the group consisting of

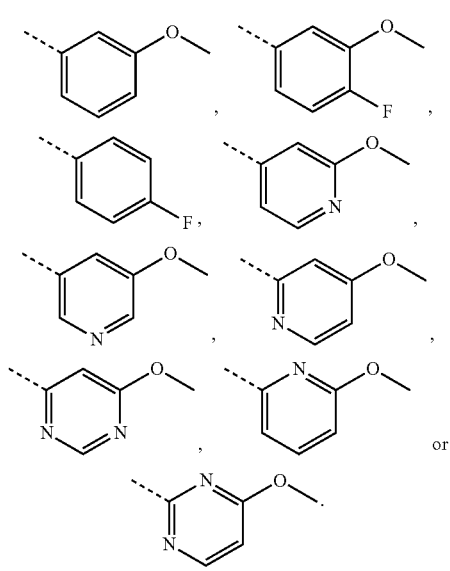

In some embodiments of the present invention, the moiety

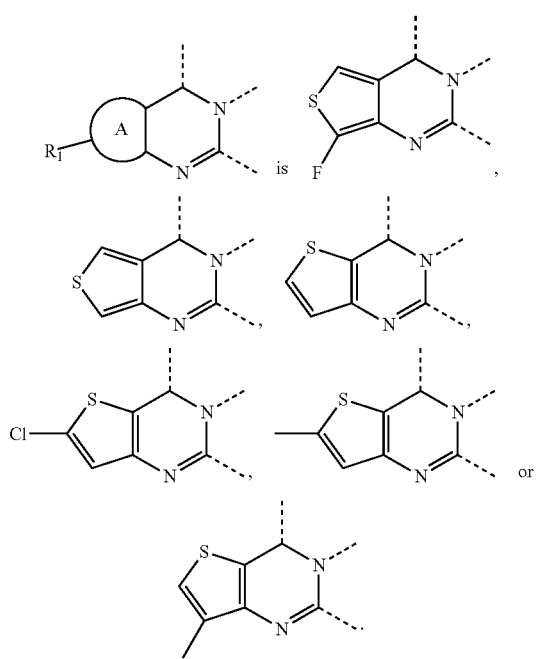

In some embodiments of the present invention, the moiety

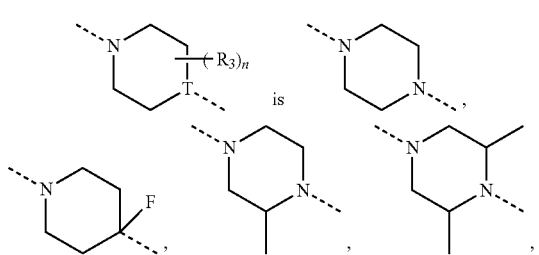

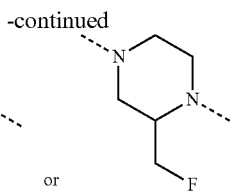

In some embodiments of the present invention, R is H, F, Cl, Br, I, OH, CN, NH$_2$ or C(=O)NH$_2$, or selected from the group consisting of C$_{1-3}$ alkyl, (C$_{1-3}$ alkyl)-O—, (C$_{1-3}$ alkyl)-S—, (C$_{1-3}$ alkyl)-NH— and N,N'-di(C$_{1-3}$ alkyl) amino, each of which is optionally substituted by 1, 2 or 3 R', other variables are as defined above.

In some embodiments of the present invention, R is H, F, Cl, Br, I, OH, CN, NH$_2$, C(=O)NH$_2$, Me, Et,

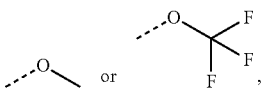

other variables are as defined above.

In some embodiments of the present invention, ring A is thienyl, furyl, oxazolyl, isothiazolyl or isoxazolyl, other variables are as defined above.

In some embodiments of the present invention, the moiety

other variables are as defined above.

In some embodiments of the present invention, R$_1$ is H, F, Cl, Br or I, or selected from the group consisting of C$_{1-3}$ alkyl, (C$_{1-3}$ alkyl)-O— and (C$_{1-3}$ alkyl)-S—, each of which is optionally substituted by 1, 2 or 3 R, other variables are as defined above.

In some embodiments of the present invention, R$_1$ is H, F, Cl, Br or I, or selected from the group consisting of Me and Et, each of which is optionally substituted by 1, 2 or 3 R, other variables are as defined above.

In some embodiments of the present invention, R$_1$ is H, F, Cl, Br, I, Me or Et, other variables are as defined above.

In some embodiments of the present invention, R$_2$ is H, or (C$_{1-3}$ alkyl)-O— which is optionally substituted by 1, 2 or 3 R, other variables are as defined above.

In some embodiments of the present invention, R$_2$ is H, or which is optionally substituted by 1, 2 or 3 R, other variables are as defined above.

In some embodiments of the present invention, $R_2$ is H,

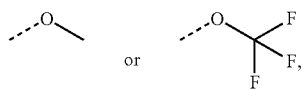

other variables are as defined above.

In some embodiments of the present invention, $R_3$ is H, or selected from the group consisting of $C_{1-3}$ alkyl, $(C_{1-3}$ alkyl)-O— and $(C_{1-3}$ alkyl)-S—, each of which is optionally substituted by 1, 2 or 3 R, other variables are as defined above.

In some embodiments of the present invention, $R_3$ is H, or selected from the group consisting of Me, Et and

each of which is optionally substituted by 1, 2 or 3 R, other variables are as defined above.

In some embodiments of the present invention, $R_3$ is H, Me, Et, $CF_3$,

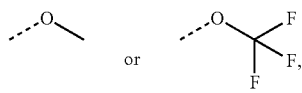

other variables are as defined above.

In some embodiments of the present invention, T is N, CH, C(F), C(Cl), C(Br) or C(I), other variables are as defined above.

In some embodiments of the present invention, Ar is selected from the group consisting of phenyl, pyridyl, pyrimidinyl, pyrazinyl and pyridazinyl, each of which is optionally substituted by 1, 2 or 3 R, other variables are as defined above.

In some embodiments of the present invention, Ar is selected from the group consisting of

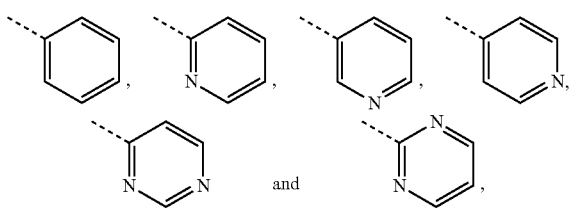

each of which is optionally substituted by 1, 2 or 3 R, other variables are as defined above.

In some embodiments of the present invention, Ar is selected from the group consisting of

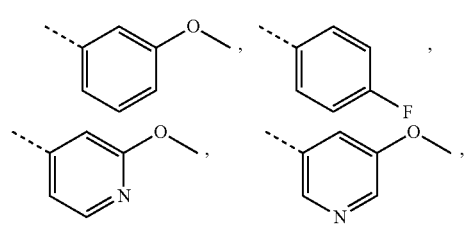

-continued

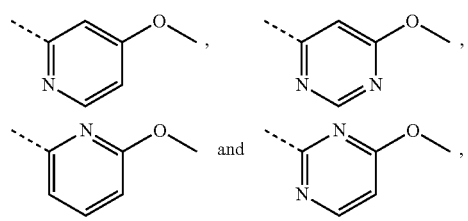

other variables are as defined above.

In some embodiments of the present invention, the moiety

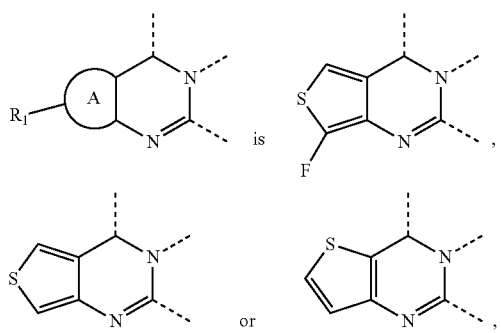

other variables are as defined above.

In some embodiments of the present invention, $R_3$ is H, Me, Et, $CF_3$,

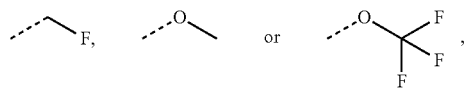

other variables are as defined above.

In some embodiments of the present invention, Ar is

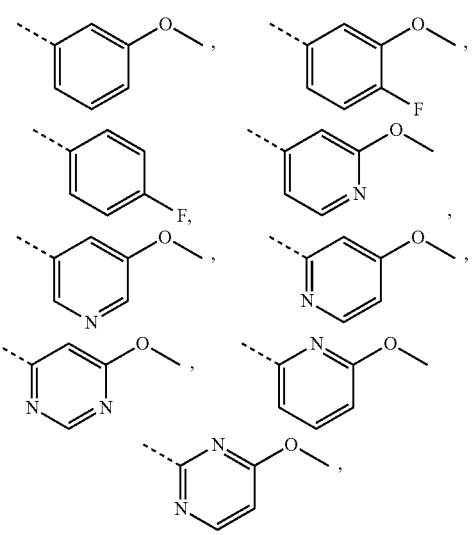

other variables are as defined above.

In some embodiments of the present invention, the moiety

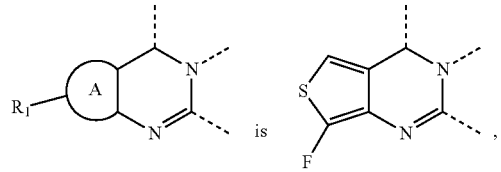

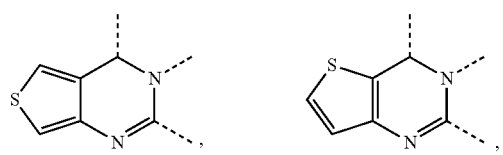

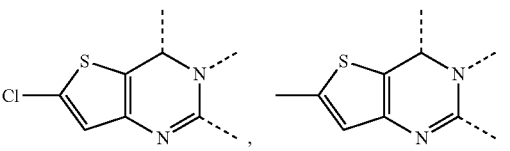

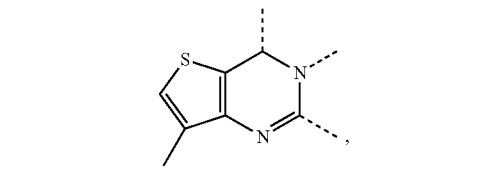

is

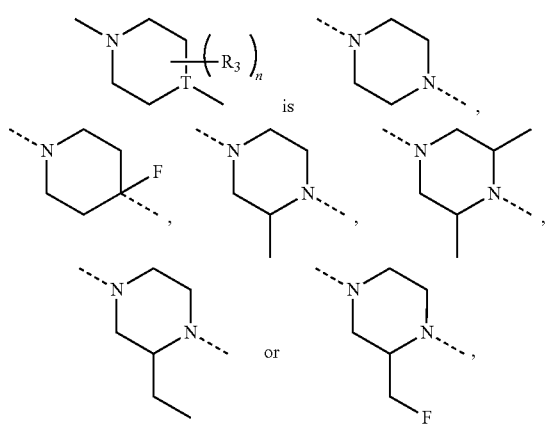

other variables are as defined above.

In some embodiments of the present invention, the moiety

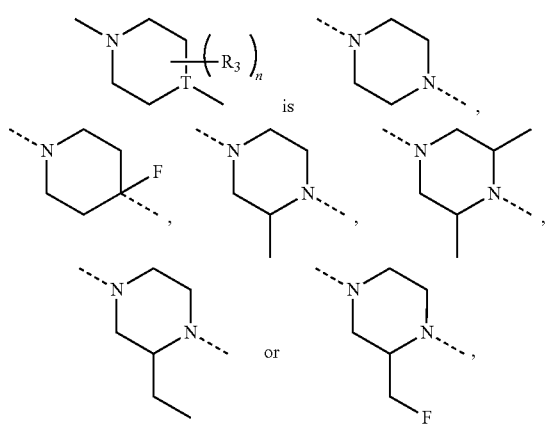

other variables are as defined above.

In some embodiments of the present invention, the compound, the pharmaceutically acceptable salt or the tautomer thereof is selected from the group consisting of

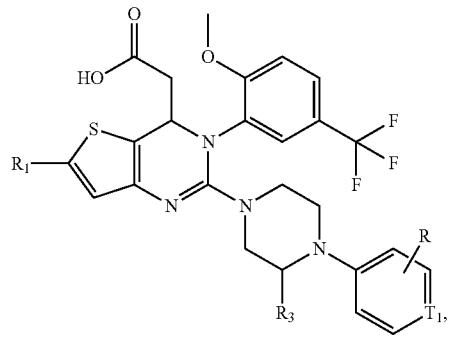
(I-1)

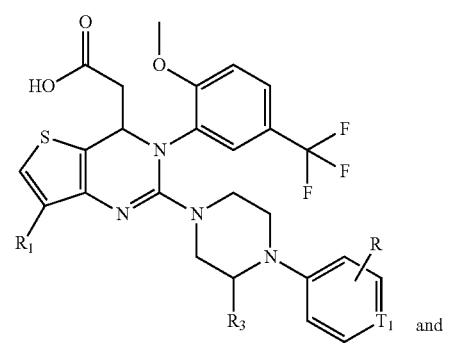
(I-2) and

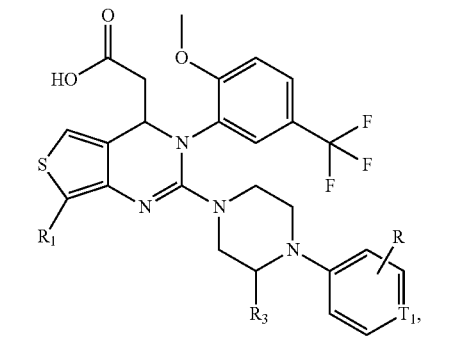
(I-3)

wherein,
$R_1$, $R_3$ and R are as defined above,
$T_1$ is N or CH.

In some embodiments of the present invention, the compound, the pharmaceutically acceptable salt or the tautomer thereof is selected from the group consisting of

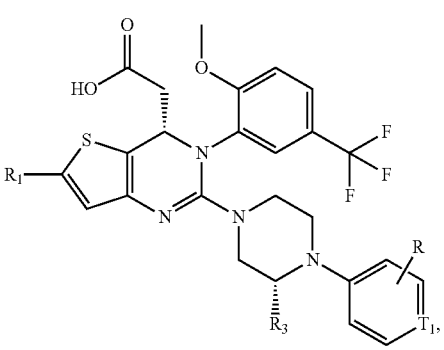
(I-1A)

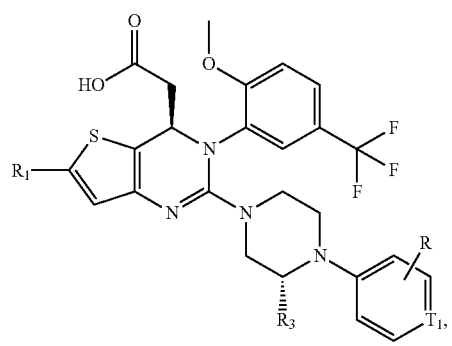 (I-1B)
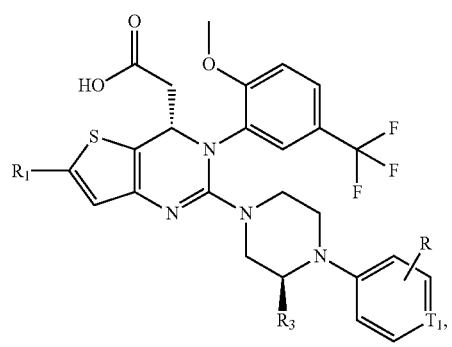 (I-1C)
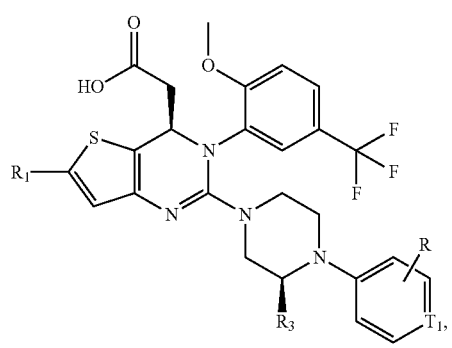 (I-1D)
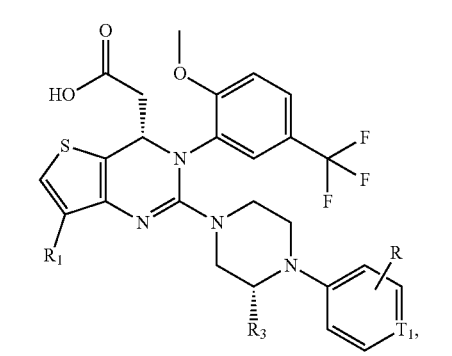 (I-2A)
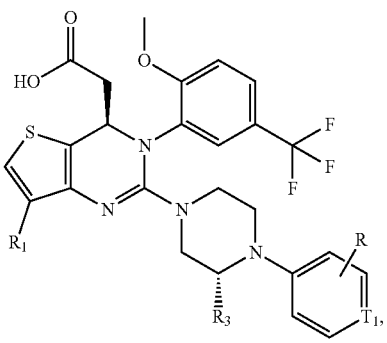 (I-2B)
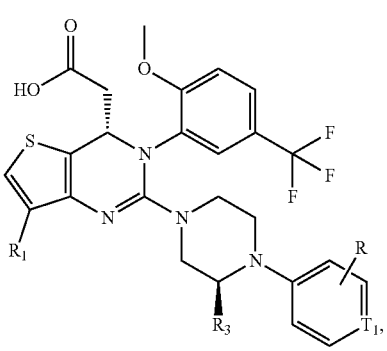 (I-2C)
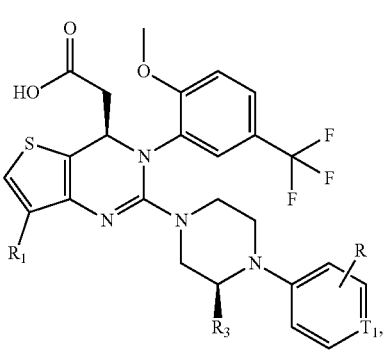 (I-2D)
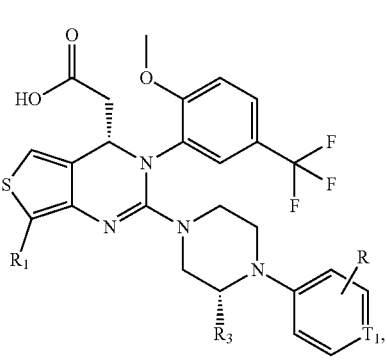 (I-3A)

15
-continued
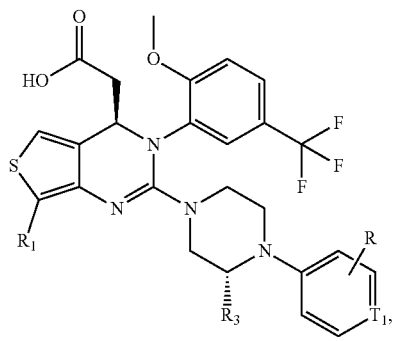
(I-3B)
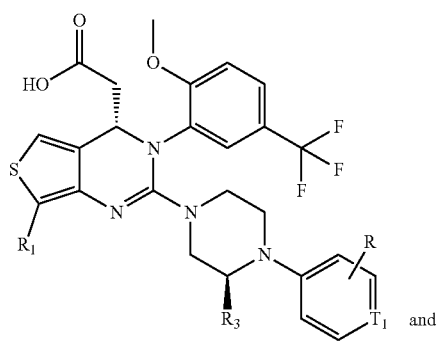
(I-3C) and
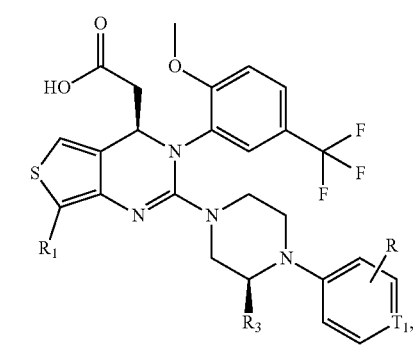
(I-3D)
wherein,
R₁, R₃ and R are as defined above,
T₁ is N or CH.
Other embodiments of the present invention can be obtained by arbitrarily combining the above variables.
The present invention provides a compound, a pharmaceutically acceptable salt or a tautomer thereof, which is selected from the group consisting of:
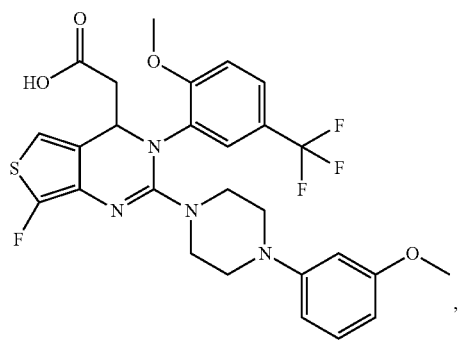
,
16
-continued
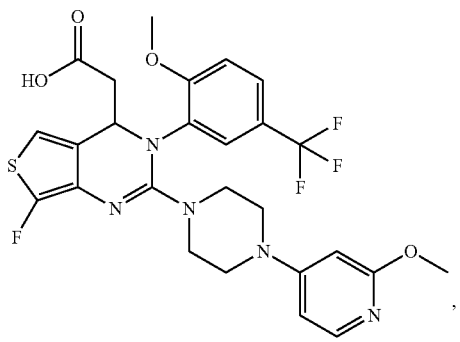
,
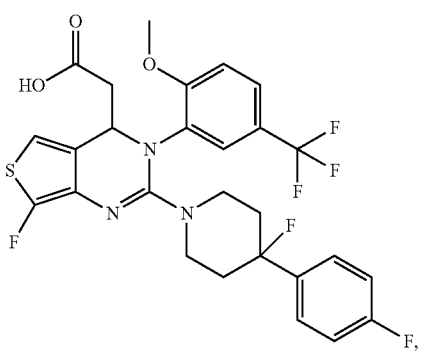
,
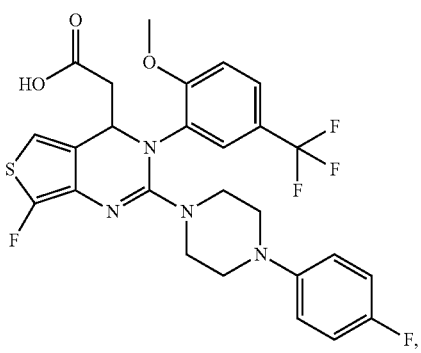
,
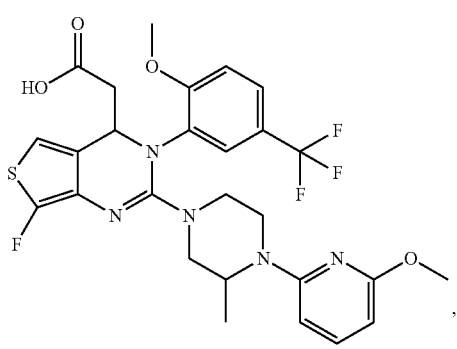
,

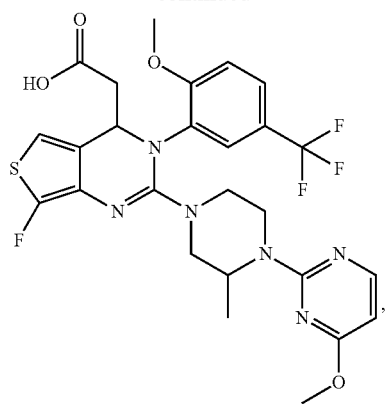
,
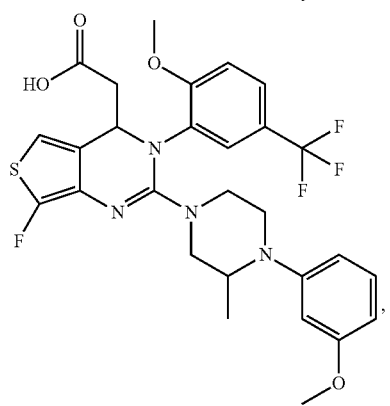
,
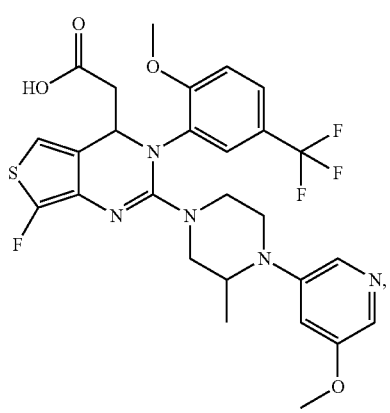
,
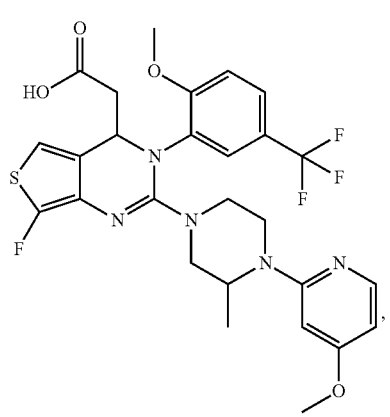
,
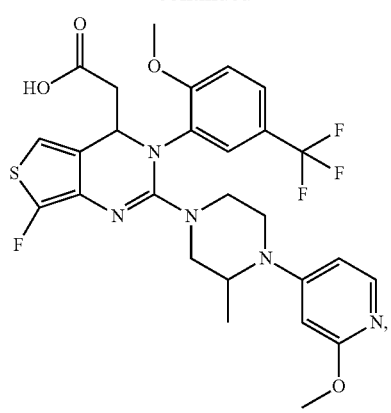
,
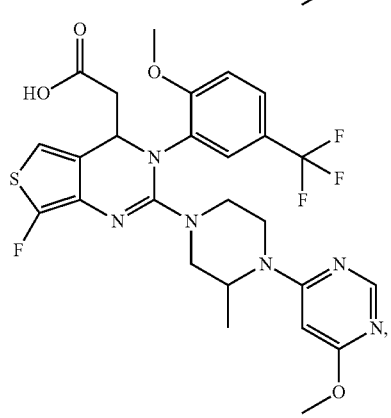
,
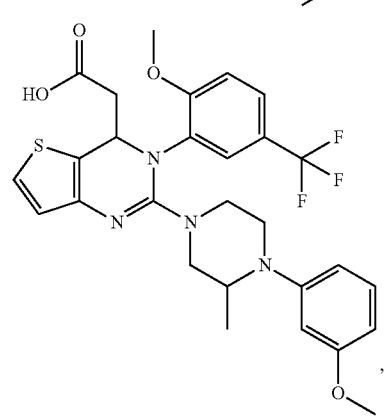
,
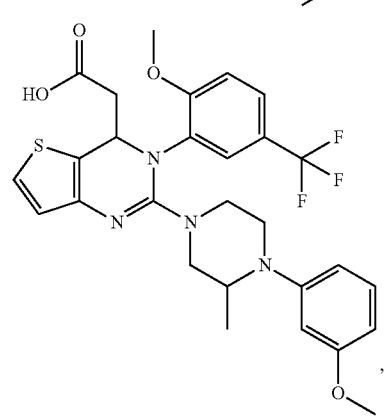
, -continued
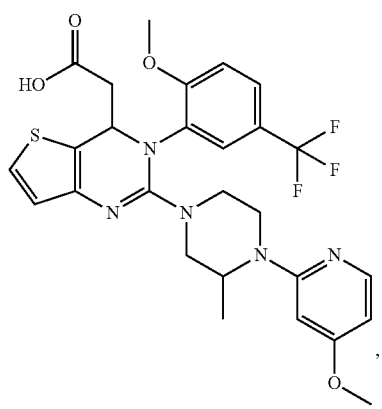
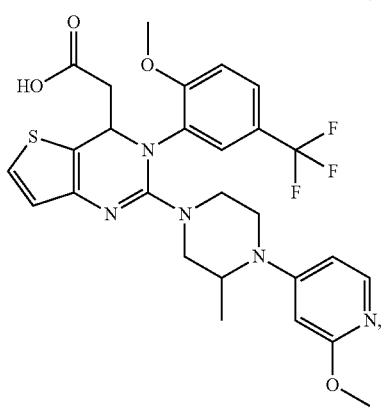
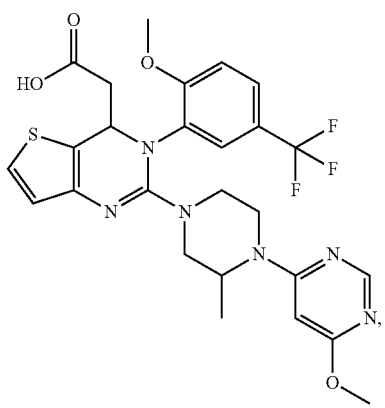
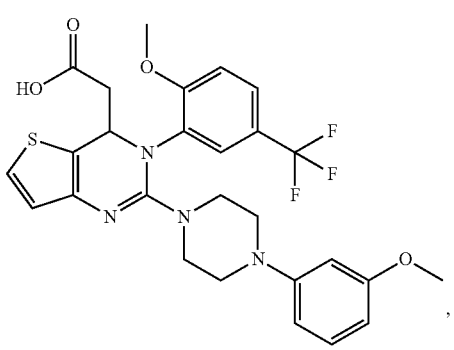
-continued
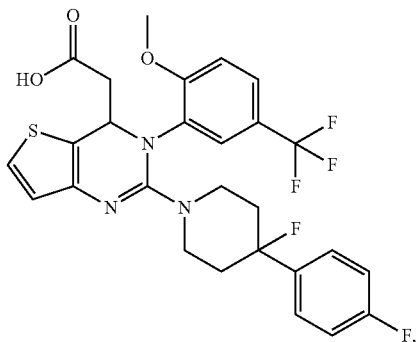
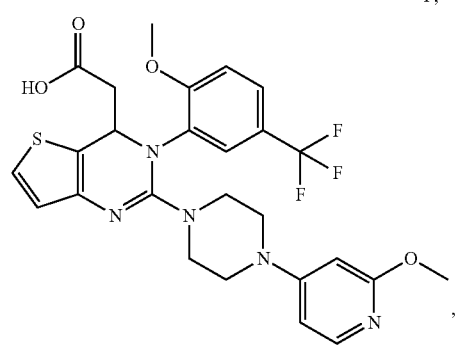
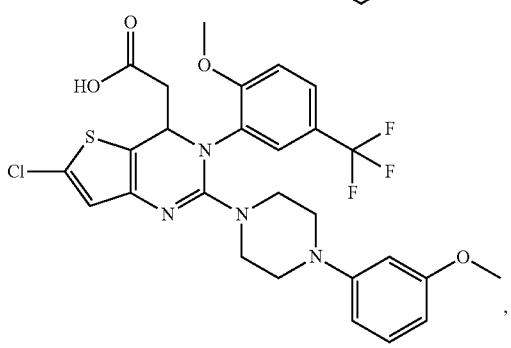
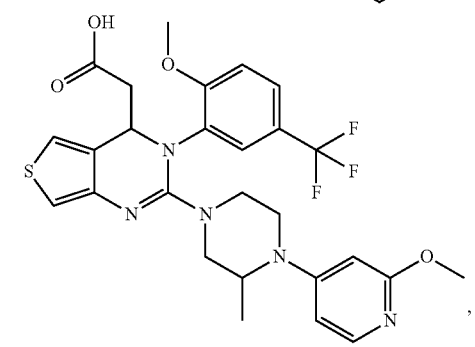
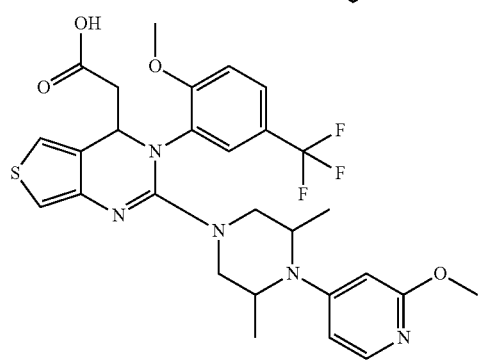

-continued
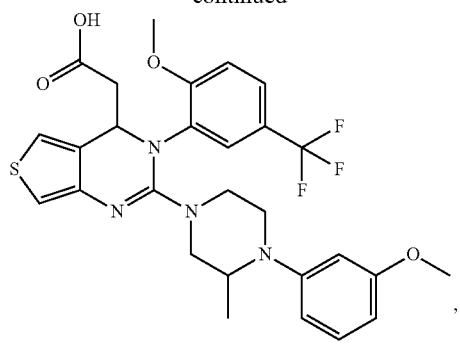
,
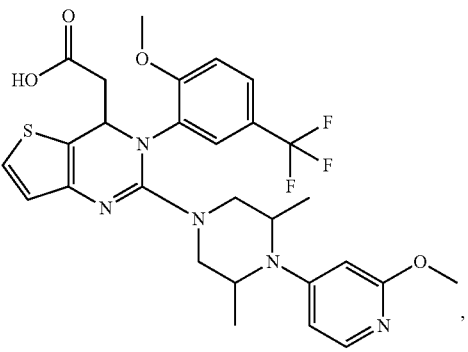
,
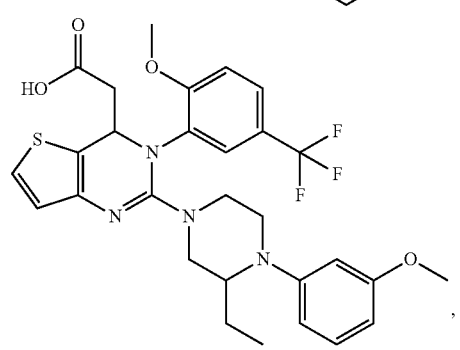
,
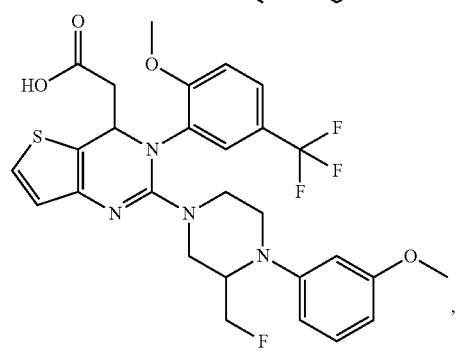
,
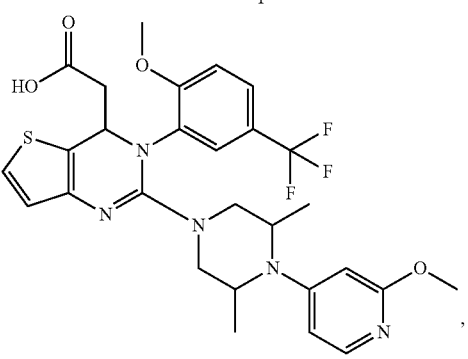
,
-continued
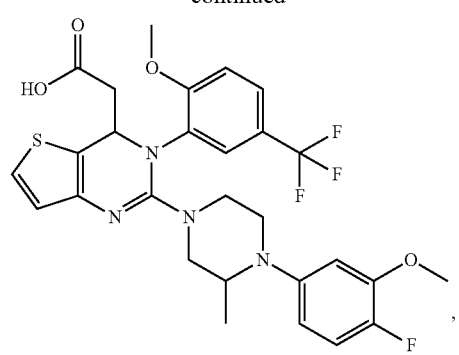
,
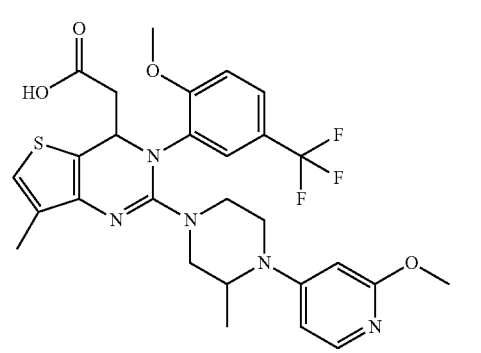
and
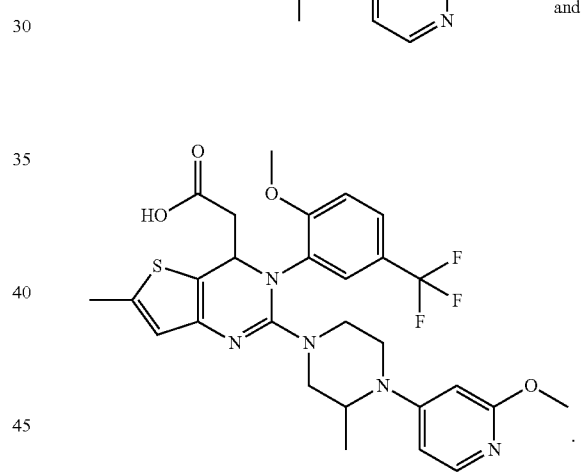
.
In some embodiments of the present invention, the compound, the pharmaceutically acceptable salt or the tautomer thereof is selected from the group consisting of:
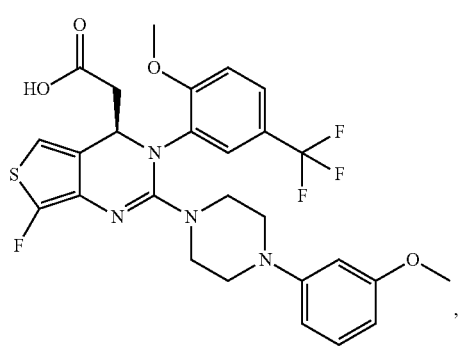
,

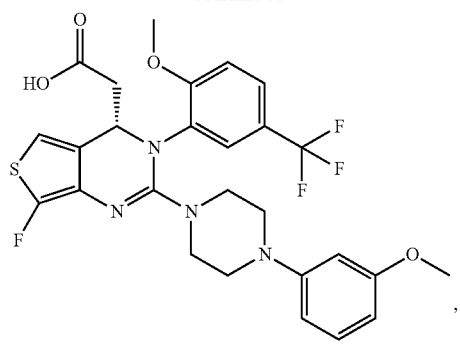
,
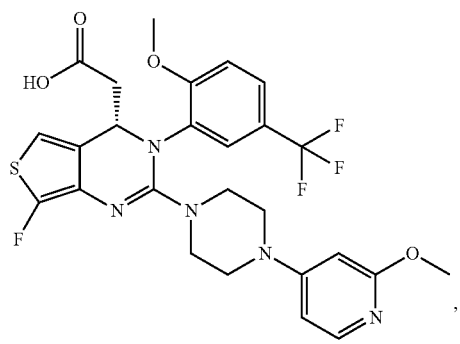
,
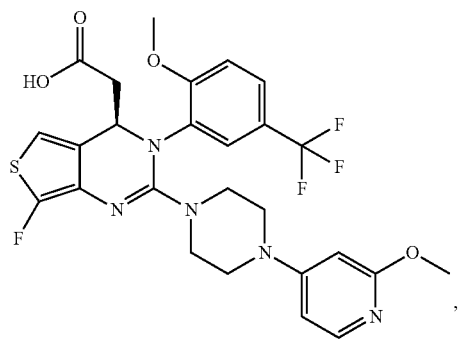
,
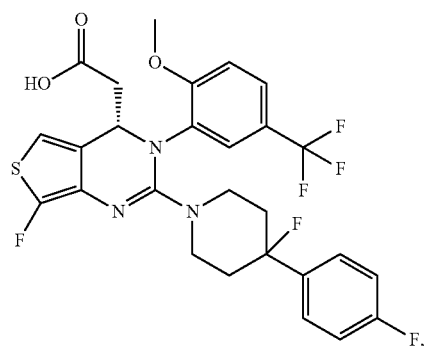
,
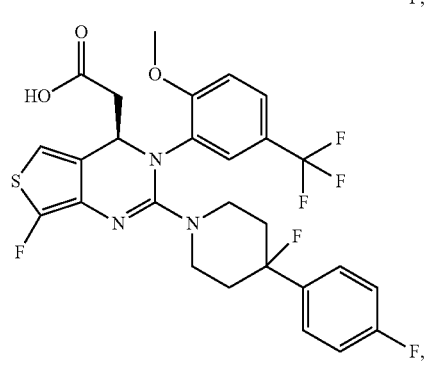
,
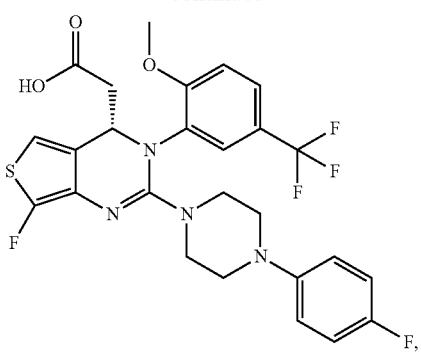
,
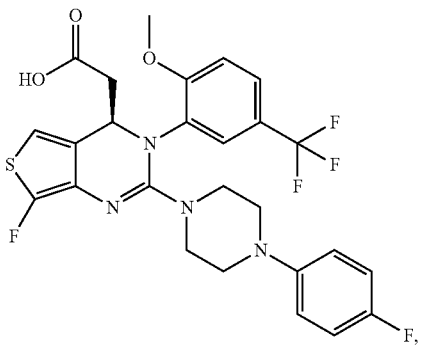
,
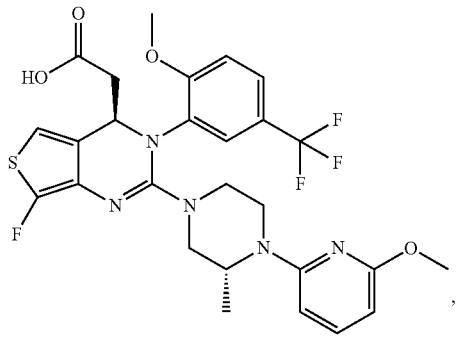
,
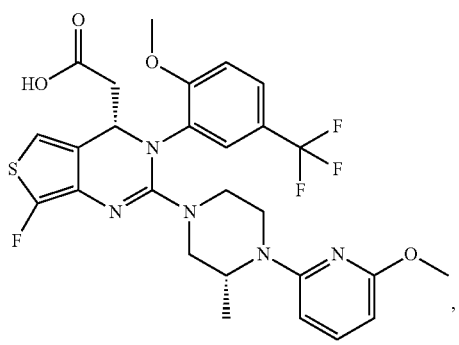
, 25
-continued
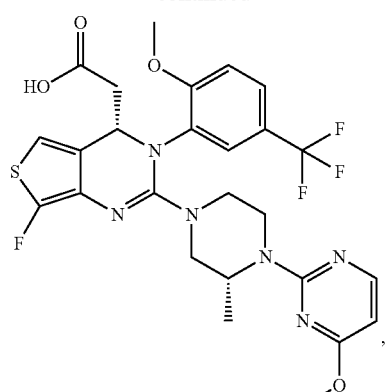
,
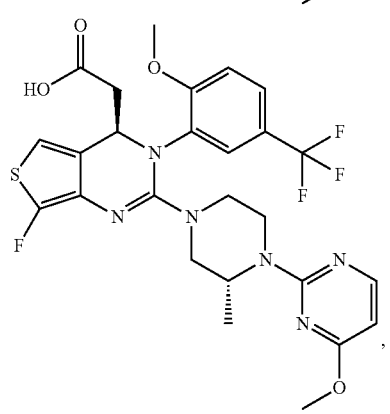
,
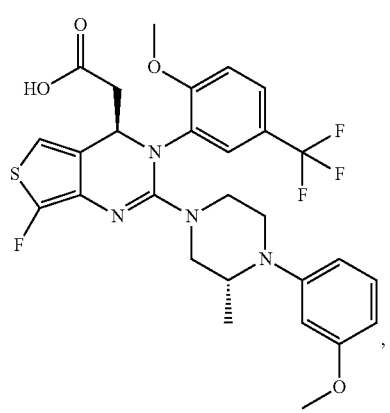
,
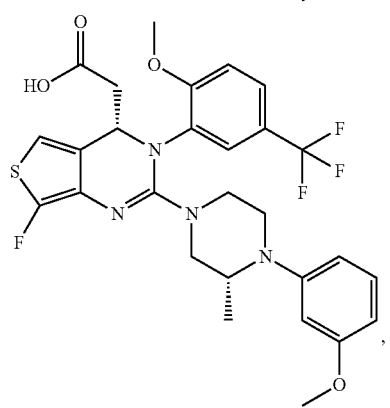
,
26
-continued
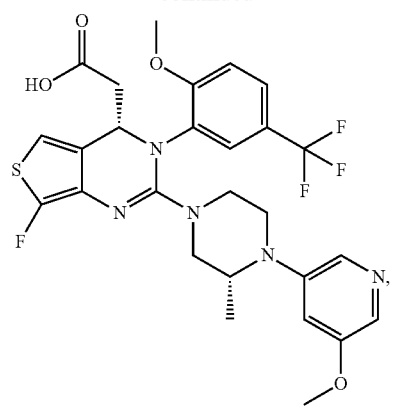
,
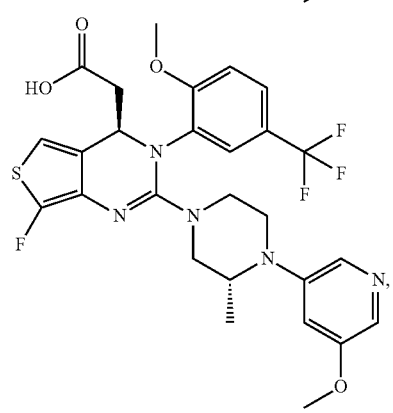
,
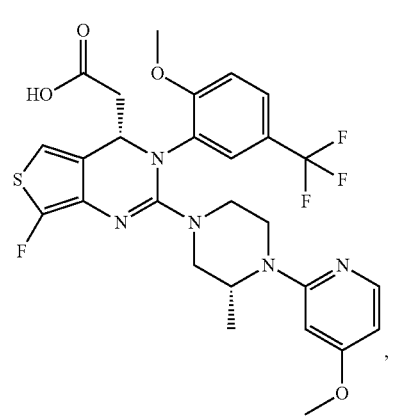
,
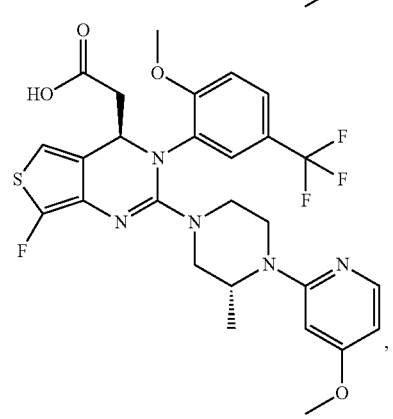
, 27
-continued
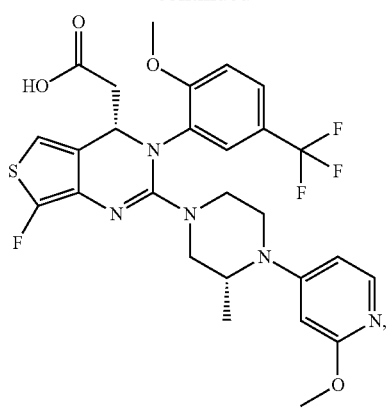
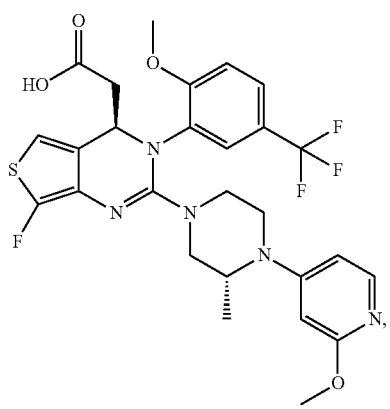
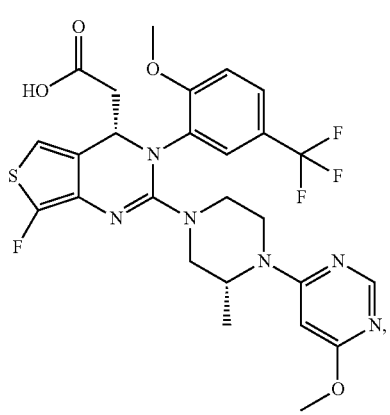
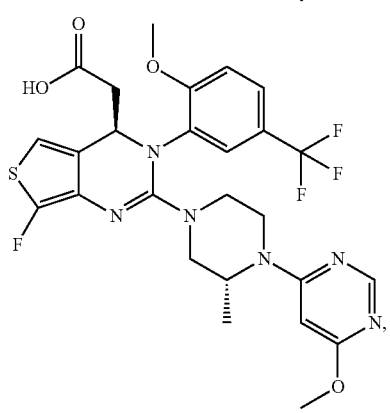
28
-continued
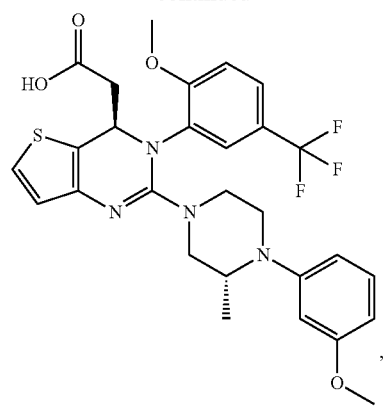
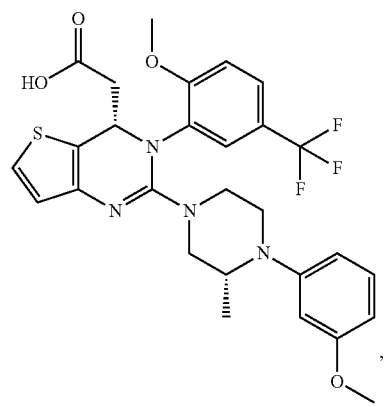
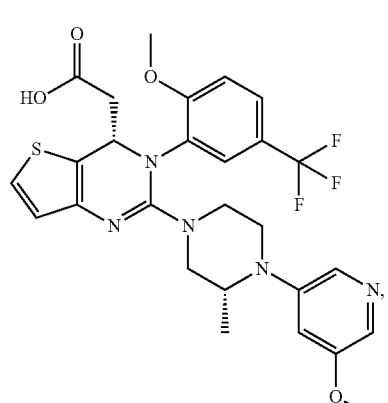
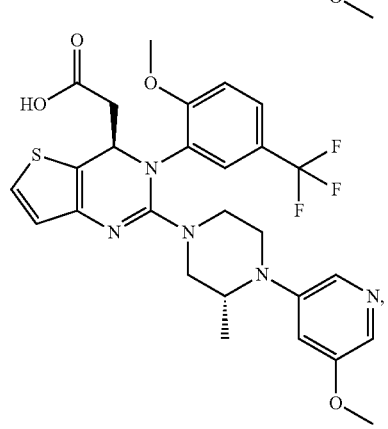

29
-continued
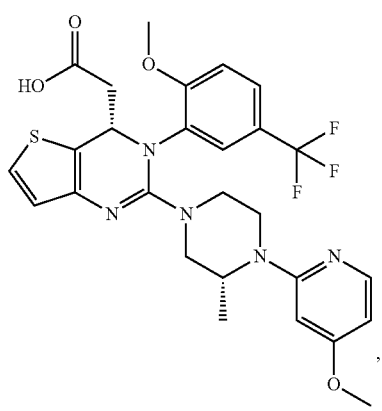
,
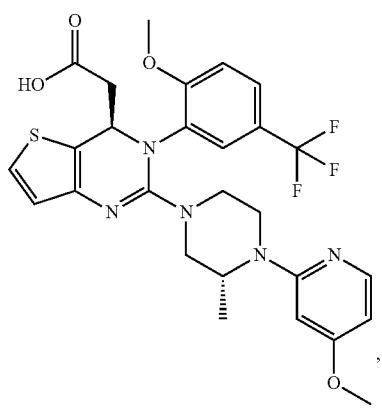
,
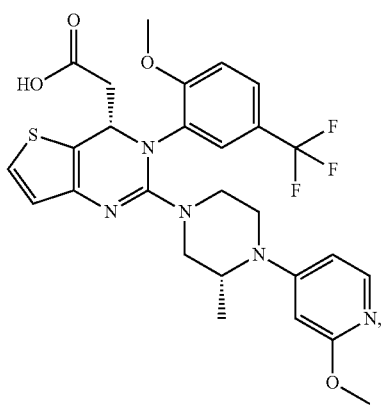
,
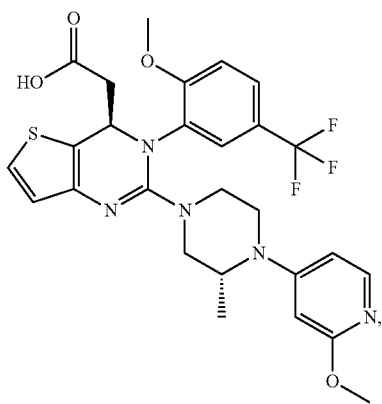
,
30
-continued
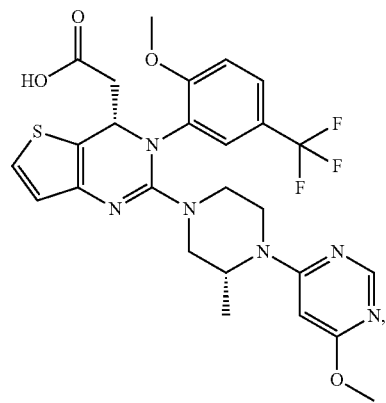
,
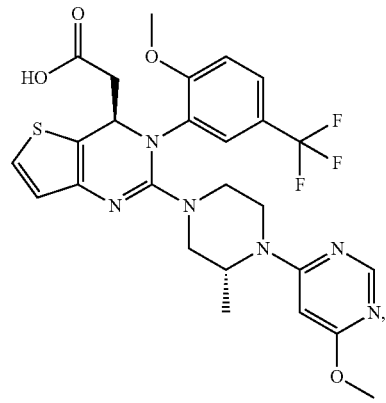
,
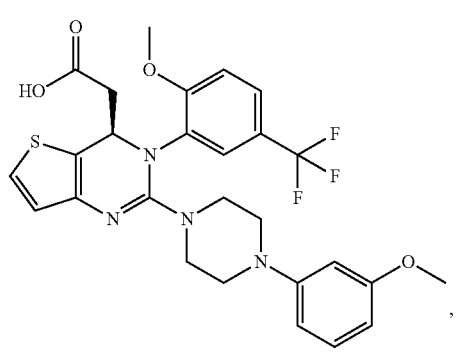
,
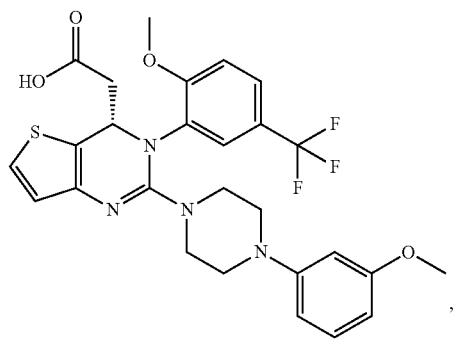
,

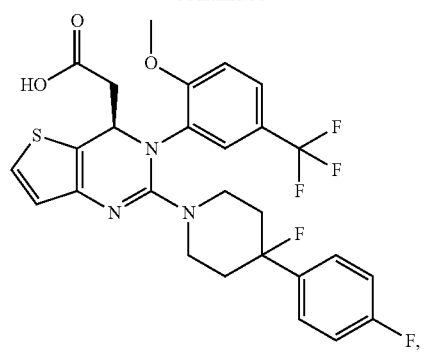
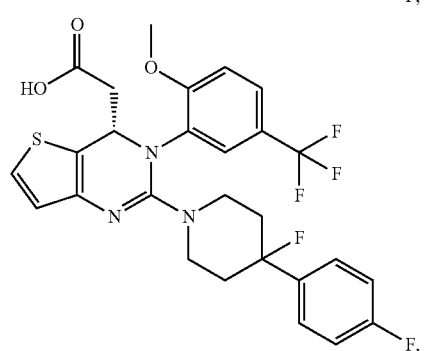
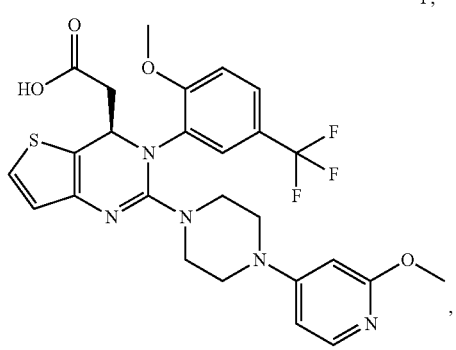
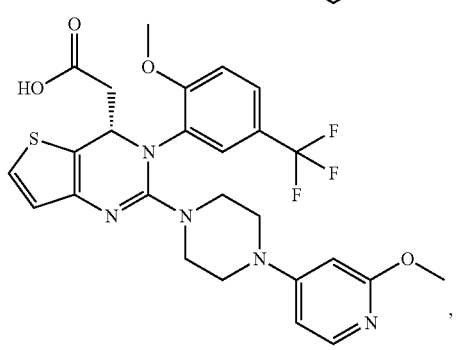
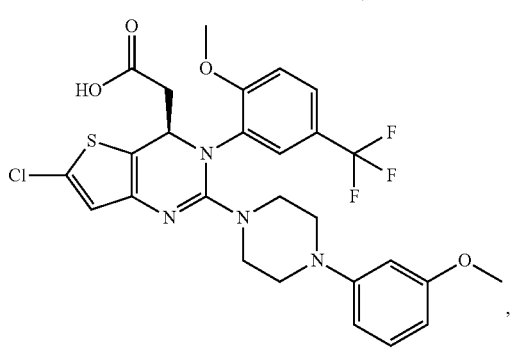
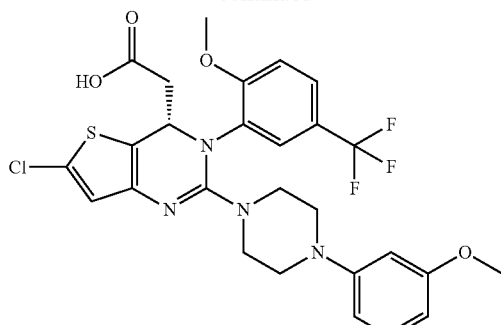
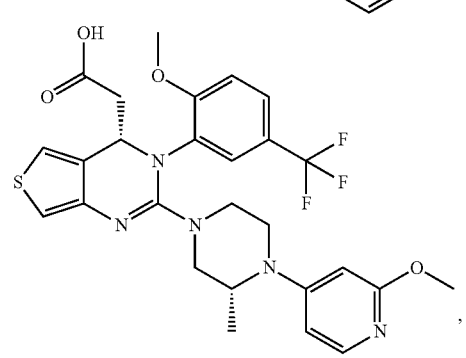
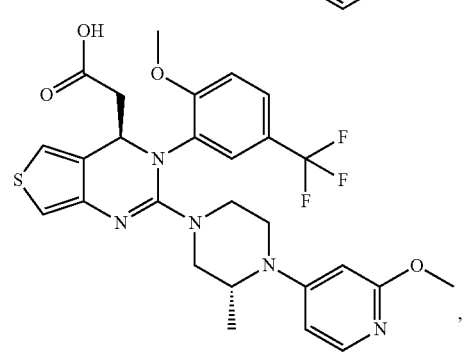
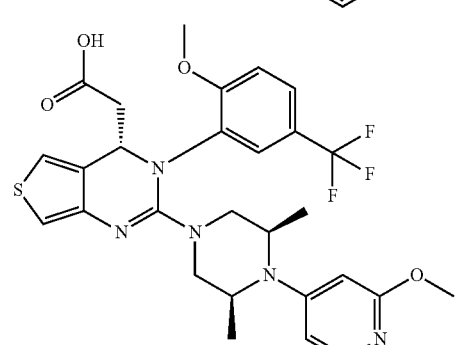
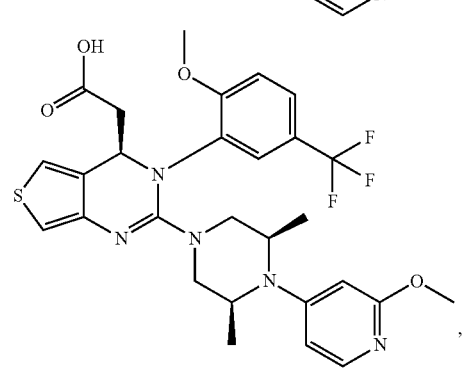

-continued
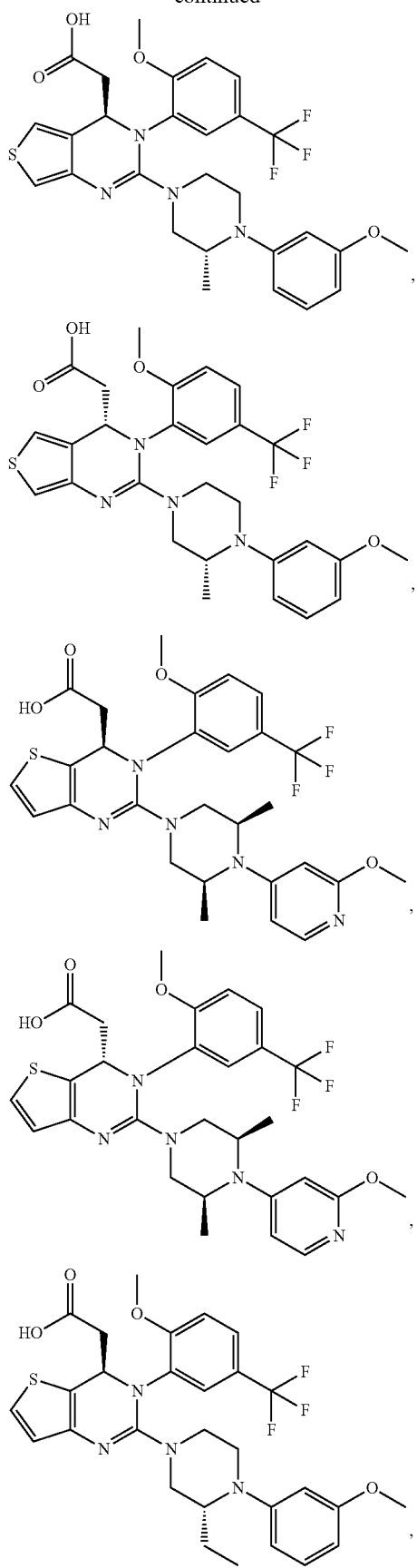
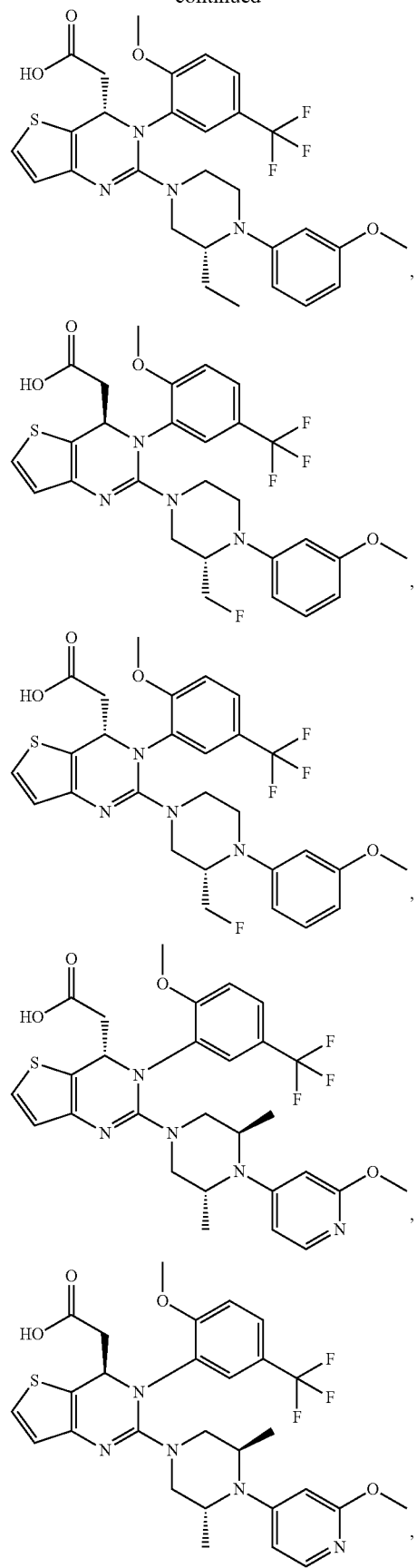

-continued

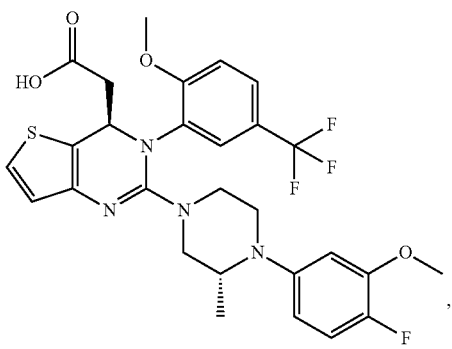

,

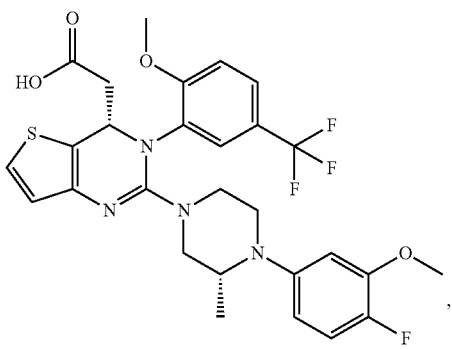

,

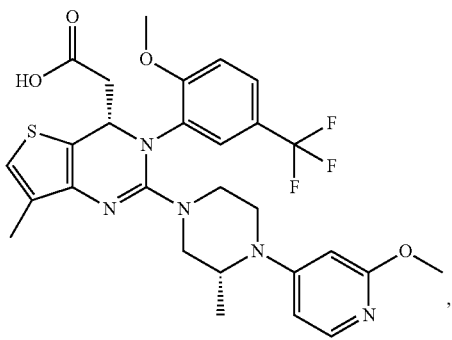

,

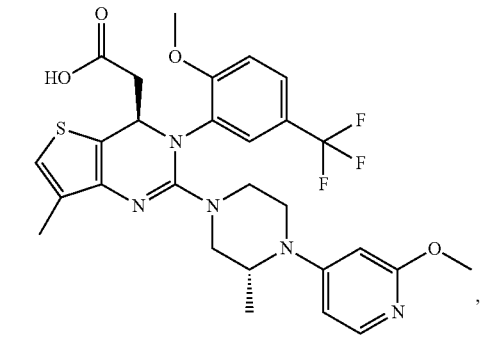

,

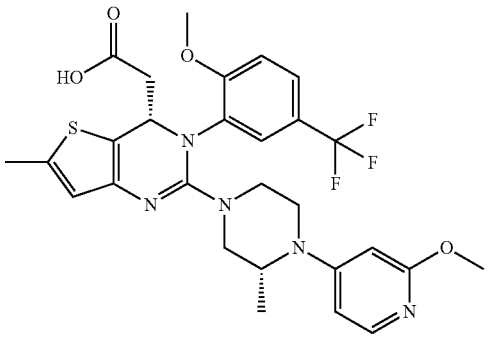

and

-continued

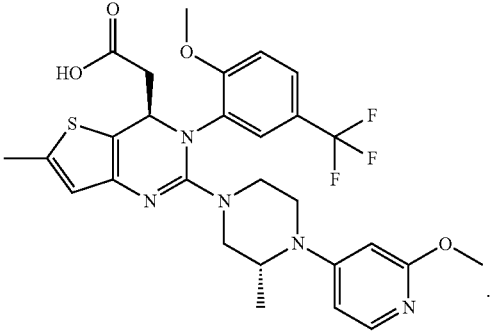

The present invention also provides a use of the compound, the pharmaceutically acceptable salt or the tautomer in manufacturing a medicament against HCMV virus.

Technical Effect:

The medicament is mainly used to prevent human cytomegalovirus infections in patients undergoing allogeneic hematopoietic stem cell transplantation, kidney transplantation, lung transplantation and pancreas transplantation. Compared with current clinical drugs, it has less toxic side effects, better oral bioavailability, and lower risk of drug resistance.

Related Definitions

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including a hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, a wedged bond and a dashed bond ( ) are used to indicate the absolute configuration of a stereogenic center,  and  are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope of the present invention.

The compound of the present invention may present in a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy*, 21*st Ed, Lippincott, Williams & Wilkins* (2005), the disclosure of which is incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

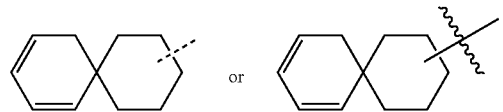

means that it can be substituted at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. The bridged ring is also included in the definition of the heterocycle. A bridged ring is formed when one or more than one atom (i.e. C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentyloxy. Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The present invention employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DBU represents 1,8-diazabicyclo[5.4.0]undec-7-ene; DCM represents dichloromethane; PE represents petroleum ether; DIAD represents diisopropyl azodicarboxylate; DMF represents N,N-dimethylformamide; DPPA represents diphenylphosphoryl azide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; rt represents room temperature; O/N represents overnight; THF represents tetrahydrofuran; MTBE represents methyl tert-butyl ether; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFth represents 1-fluoro-4-hydroxy-1,4-diazabicyclooctane bis(tetrafluoroborate); NCS represents N-chlorosuccinimide; NBS represents N-bromosuccinimide; n-Bu$_4$NF represents tetrabutylammonium fluoride; iPrOH represents 2-propanol; mp represents melting point; LDA represents lithium diisopropylamide.

Compounds are named manually or by ChemDraw® software, the commercially available compounds use their vendor directory names.

DETAILED DESCRIPTION OF THE PREFERRED EMBODIMENT

The following embodiments further illustrate the present invention, but the present invention is not limited thereto.

Reference Embodiment 1: Fragment BB-1, BB-2, BB-3, BB-4, BB-5, BB-6, BB-7, BB-8, BB-9, BB-10, BB-12, BB-13, BB-14, BB-15, BB-16

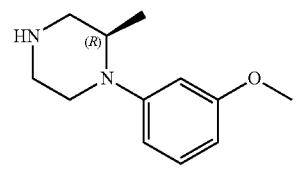

BB-1

Synthetic Route

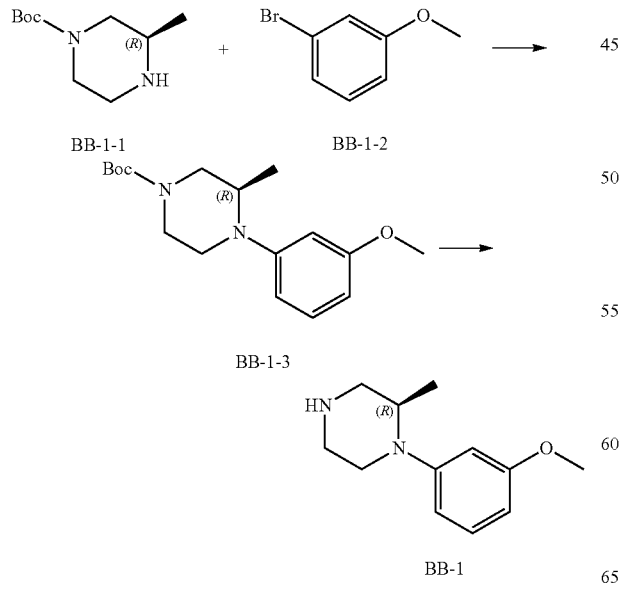

Step 1: Synthesis of Compound BB-1-3

To a solution of compound BB-1-1 (3.50 g, 17.48 mmol, 1.00 eq) and compound BB-1-2 (4.90 g, 26.22 mmol, 3.31 mL, 1.50 eq) in toluene (50.00 mL) was added tri-tert-butylphosphine (1 M in toluene, 174.80 μL, 0.01 eq), Pd$_2$(dba)$_3$ (160.03 mg, 174.80 μmol, 0.01 eq) and potassium tert-butoxide (2.94 g, 26.22 mmol, 1.50 eq) at room temperature. The reaction solution was stirred under nitrogen atmosphere at 100° C. for 12 hours. Then the reaction solution was evaporated to dryness and the residue was purified by silica gel column (PE/EtOAc=2/1) to give BB-1-3 (2.80 g, yield 39.42%).

Step 2: Synthesis of Compound BB-1

Trifluoroacetic acid (1.54 g, 13.51 mmol, 1.00 mL, 10.31 eq) was added to a solution of BB-1-3 (400.00 mg, 1.31 mmol, 1.00 eq) in dichloromethane (5.00 mL). The reaction solution was stirred at 15° C. for 3 hours. The reaction solution was evaporated to dryness to give a crude product of compound BB-1 (400.00 mg, TFA). MS (ESI) m/z: 207.1 [M+1].

Referring to the synthesis method of step 1 and 2 in reference embodiment 1, the reference embodiments in the following table were synthesized.

| No. of reference embodiments | Structure | MS + 1 |
|---|---|---|
| BB-2 | 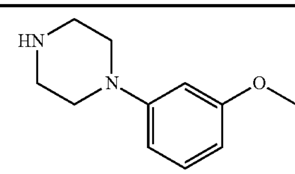 | 193.2 |
| BB-3 | 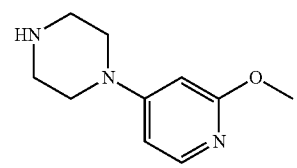 | 194.2 |
| BB-4 | 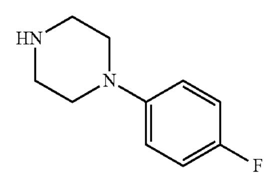 [SMILES: Fc1ccc(N2CCNCC2)cc1] | 181.2 |
| BB-5 | 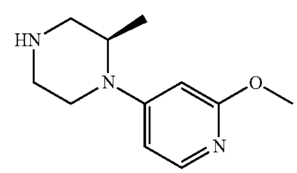 | 208.2 |
| BB-6 | 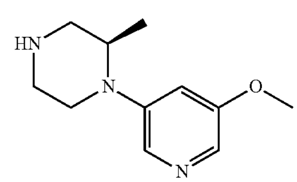 | 208.2 |
| BB-7 | 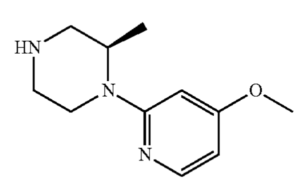 | 208.2 |

-continued

| No. of reference embodiments | Structure | MS + 1 |
|---|---|---|
| BB-8 | 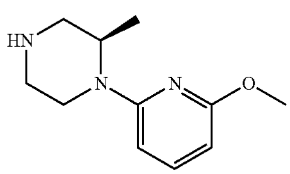 | 208.2 |
| BB-9 | 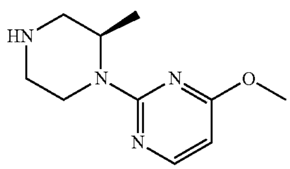 | 209.2 |
| BB-10 | 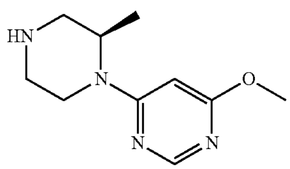 | 209.2 |
| BB-12 | 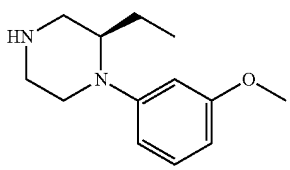 [SMILES: CC[C@@H]1CNCCN1c1cccc(OC)c1] | 221.2 |
| BB-13 | 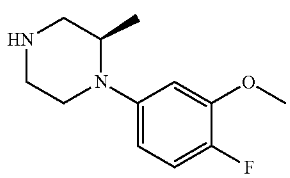 [SMILES: COc1cc(N2CCNC[C@H]2C)ccc1F] | 225.1 |
| BB-14 | 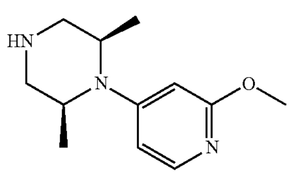 [SMILES: COc1cc(N2[C@H](C)CNC[C@@H]2C)ccn1] | 222.2 |
| BB-15 | 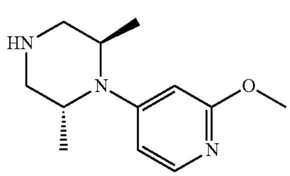 [SMILES: COc1cc(N2[C@H](C)CNC[C@H]2C)ccn1] | 222.2 |
| BB-16 | 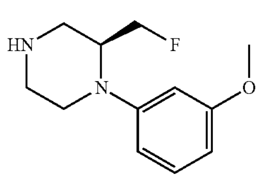 | 225.1 |

Reference Embodiment 2: Fragment BB-11

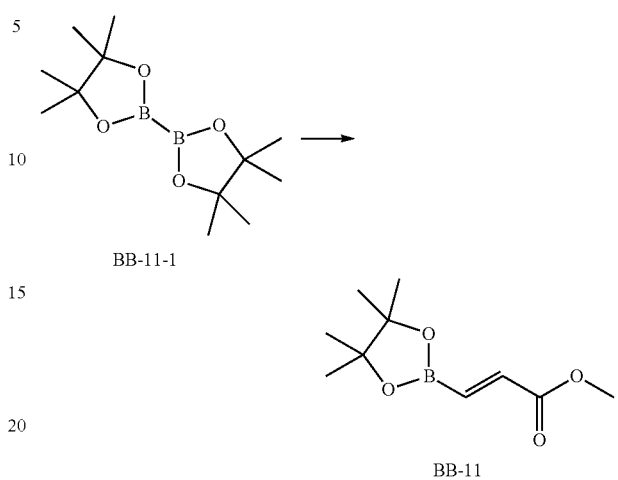

BB-11-1

BB-11

To a solution of cuprous chloride (353.28 mg, 3.57 mmol, 85.33 μL, 0.03 eq) and Xantphos (2.06 g, 3.57 mmol, 0.03 eq) in tetrahydrofuran (150 mL) was added sodium tert-butoxide (685.87 mg, 7.14 mmol, 0.06 eq) at 0° C. And the reaction solution was stirred at 0° C. for one hour, followed by addition of a solution of BB-11-1 (30.21 g, 118.95 mmol, 1.00 eq) in tetrahydrofuran (50 mL). The reaction solution was stirred under nitrogen atmosphere at 20° C. for one hour. Methyl propiolate (10.00 g, 118.95 mmol, 9.90 mL, 1.00 eq) and methanol (7.62 g, 237.90 mmol, 2.00 eq) were added to the above reaction solution. And the reaction solution was stirred at 20° C. for 12 hours. Then the reaction solution was evaporated to dryness, diluted with water (200 mL) and extracted twice with ethyl acetate (150 mL), the organic phase was washed with saturated sodium bicarbonate solution (150 mL) and brine (100 mL), dried over sodium sulfate and evaporated under reduced pressure, the residue was purified by silica gel column (PE/EtOAc=20/1) to give BB-11 (18.00 g, 84.89 mmol, yield 71.36%).

$^1$HNMR (400 MHz, CHLOROFORM-d) δ 6.75-6.86 (m, 1H), 6.62 (d, J=18 Hz, 1H), 3.71-3.79 (m, 3H), 1.28-1.30 (m, 12H).

Embodiment 1

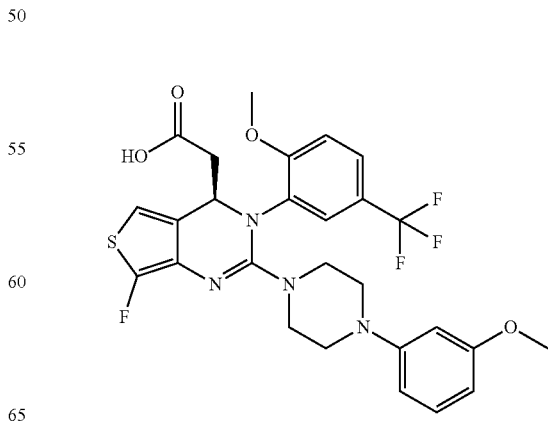

Synthetic Route:
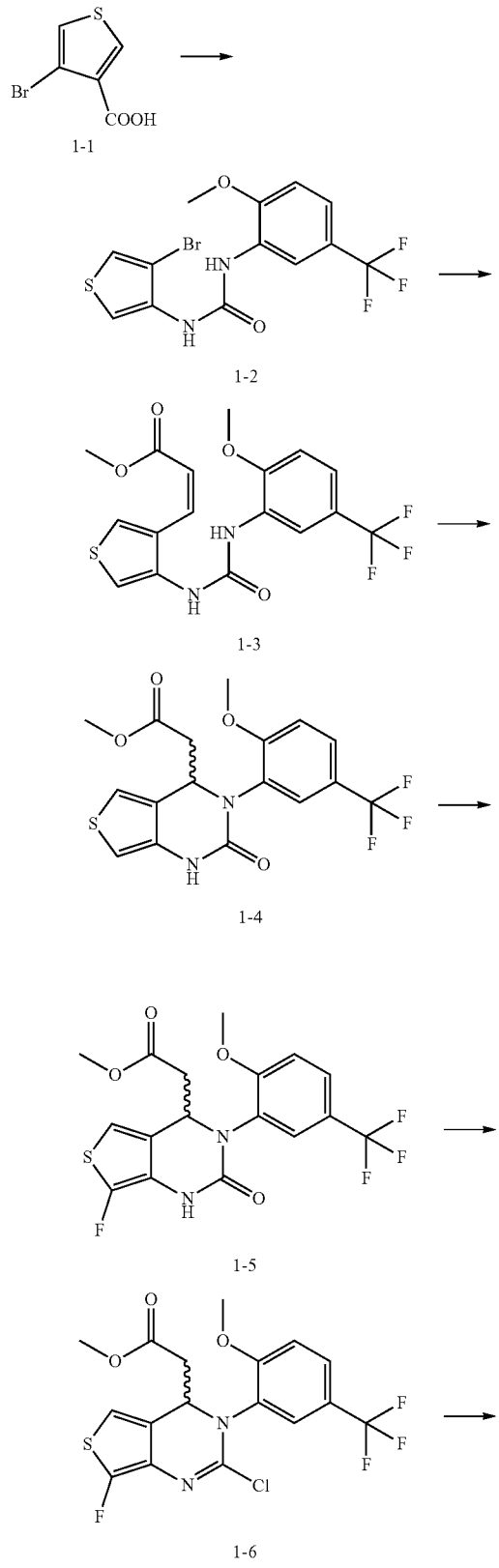
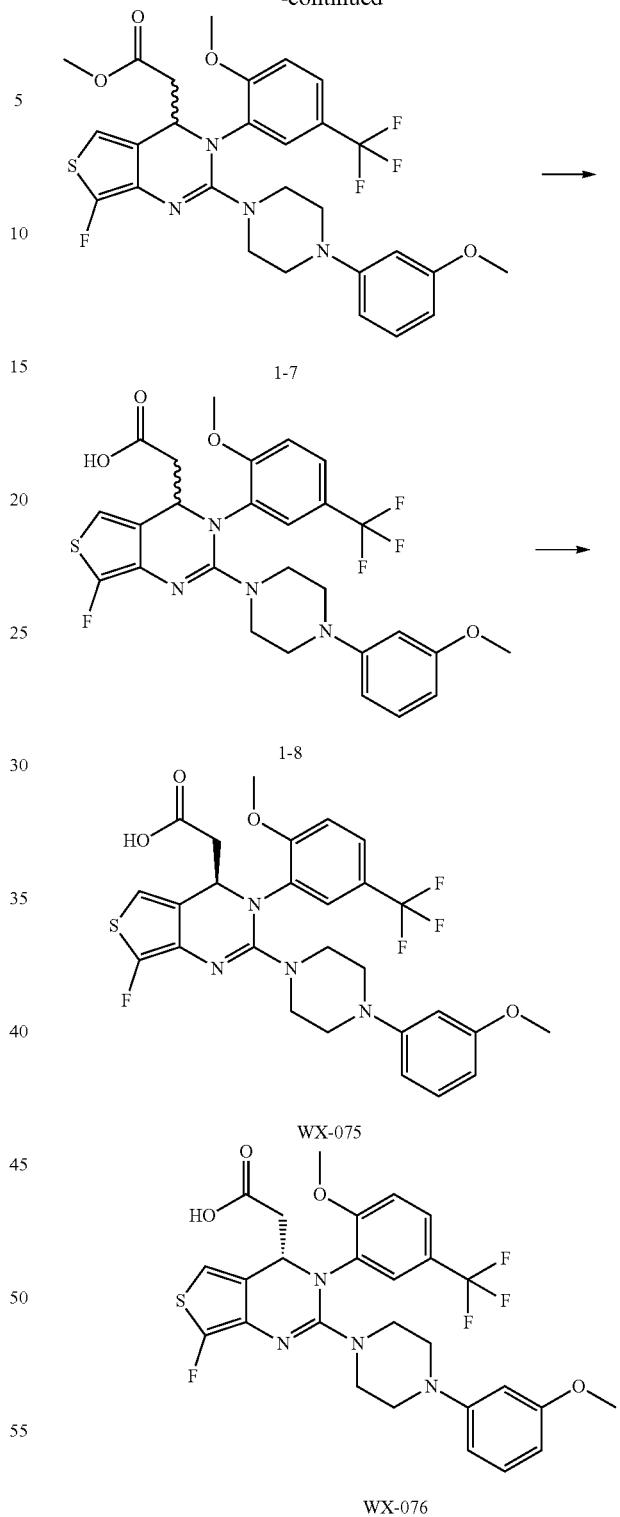
Step 1: Synthesis of Compound 1-2
To a solution of compound 1-1 (10.00 g, 48.30 mmol, 1.00 eq) in toluene (100.00 mL) was added diphenyl azidophosphate (19.94 g, 72.45 mmol, 1.50 eq) in an ice bath, followed by dropwise addition of triethylamine (14.66 g, 144.90 mmol, 3.00 eq). After the mixture was warmed to room temperature and stirred for 1 hour, the mixture was heated to 80° C. and stirred for 1 hour, followed by addition of 2-methoxy-5-trifluoromethylaniline (12.93 g, 67.62 mmol, 1.4 eq), the reaction solution was stirred at 80° C. overnight. Then the reaction solution was cooled to room temperature and evaporated under reduced pressure. The residue was diluted with water (50 mL) and extracted with ethyl acetate (100 mL) for three times, the organic phase was washed with brine, dried over sodium sulfate, filtered and concentrated under reduced pressure to give a crude product, which was recrystallized with a mixed solvent (petroleum ether:ethyl acetate=3:1, 50 mL) to give compound 1-2 (12.00 g, 30.37 mmol, yield 62.87%). $^1$HNMR (400 MHz, DMSO-$d_6$) δ 9.28 (s, 1H), 9.07-9.17 (m, 1H), 8.56 (d, J=2.0 Hz, 1H), 7.63-7.72 (m, 2H), 7.33 (dd, J=1.6, 8.4 Hz, 1H), 7.20 (d, J=8.4 Hz, 1H), 3.97 (s, 3H).

Step 2: Synthesis of Compound 1-3

To a solution of compound 1-2 (5.00 g, 12.65 mmol, 1.00 eq) in N,N-dimethylacetamide (60.00 mL) was added Methyl acrylate (8.71 g, 101.20 mmol, 8.00 eq), bis(acetonitrile)dichloropalladium (164.12 mg, 632.50 µmol, 0.05 eq), tris(o-methylphenyl)phosphine (385.09 mg, 1.27 mmol, 0.10 eq) and triethylamine (6.40 g, 63.25 mmol, 5.00 eq) at room temperature, the reaction solution was purged with nitrogen for three times and stirred at 100° C. for 12 hours. Then the reaction solution was diluted with water (20 mL), extracted three times with ethyl acetate (50 mL), the organic phase was washed with brine, dried over anhydrous sodium sulfate, filtered, and concentrated under reduced pressure to give a crude product, which was purified by silica gel column chromatography (PE:EtOAc=5:1 to 4:1) to give compound 1-3 (4.00 g, 5.99 mmol, yield 47.39%). MS (ESI) m/z: 400.9 [M+1].

Step 3: Synthesis of Compound 1-4

To a solution of compound 1-3 (2.00 g, 5.00 mmol, 1.00 eq) in tetrahydrofuran (10.00 mL) was added a solution of sodium hydroxide (1 M, 500.00 µL, 0.10 eq) at room temperature, the mixture was stirred at 50° C. for 12 hours. Then the reaction solution was concentrated under reduced pressure and the residue was purified by silica gel column chromatography (PE:EtOAc=4:1 to 2:1) to give compound 1-4 (800.00 mg, 2.00 mmol, yield 39.96%). MS (ESI) m/z: 401.1 [M+1].

Step 4: Synthesis of Compound 1-5

To a solution of compound 1-4 (1.00 g, 2.50 mmol, 1.00 eq) in acetonitrile (30.00 mL) was added NFTh (2.41 g, 7.50 mmol, 3.00 eq) and anhydrous sodium carbonate (397.10 mg, 3.75 mmol, 156.96 µL, 1.50 eq) at room temperature, the mixture was stirred at 70° C. for 12 hours. Then the reaction solution was concentrated under reduced pressure and the residue was purified by silica gel column chromatography (PE:EtOAc=10:1 to 5:1) to give compound 1-5 (220.00 mg, 525.86 µmol, yield 21.03%). MS (ESI) m/z: 419.1 [M+1].

Step 5: Synthesis of Compound 1-6

A solution of compound 1-5 (50.00 mg, 119.51 µmol, 1.00 eq) in phosphorus oxychloride (7.16 g, 46.70 mmol, 390.73 eq) was stirred at 100° C. for 12 hours. Then the reaction solution was concentrated under reduced pressure, the residue was quenched with ice water (10 mL) and extracted twice with ethyl acetate (20 mL). The combined organic phases were washed with brine, dried over anhydrous sodium sulfate, filtered and concentrated under reduced pressure to give a crude product of compound 1-6 (52.20 mg), which was directly used in the next step.

Step 6: Synthesis of Compound 1-7

To a solution of compound 1-6 (52.20 mg, 119.50 µmol, 1.00 eq) in acetonitrile (4.00 mL) was added Compound BB-2 (68.93 mg, 358.50 µmol, 3.00 eq) and anhydrous potassium carbonate (330.32 mg, 2.39 mmol, 20.00 eq) at room temperature, the mixture was stirred at 80° C. for 12 hours. Then the reaction solution was concentrated under reduced pressure, diluted with water (10 mL), extracted twice with ethyl acetate (20 mL), the combined organic phases were washed with brine, dried over anhydrous sodium sulfate, filtered and concentrated under reduced pressure to give a crude product, which was purified by silica gel column chromatography (PE:EtOAc=5:1 to 3:1) to give compound 1-7 (50.00 mg, 88.88 µmol, yield 74.37%). MS (ESI) m/z: 593.2 [M+1].

Step 7: Synthesis of Compound 1-8

To a solution of compound 1-7 (50.00 mg, 84.37 µmol, 1.00 eq) in methanol (2.00 mL), tetrahydrofuran (2.00 mL) and water (1.00 mL) was added Sodium hydroxide (16.87 mg, 421.85 µmol, 5.00 eq), the mixture was stirred at 25° C. for 12 hours. Then the reaction solution was concentrated under reduced pressure and the residue was purified by preparative HPLC to give compound 1-8 (20.00 mg, 32.52 µmol, yield 38.54%). MS (ESI) m/z: 579.1 [M+1].

Step 8: Synthesis of Compound WX-075 and WX-076

Compound 1-8 (18.00 mg, 31.11 µmol, 1.00 eq) was purified by Prep-SFC [column: OD (250 mm*30 mm, 5 µm), mobile phase (A: $CO_2$, B: methanol containing 0.1 ammonium hydroxide, gradient: B 40%-40%)] to give compound WX-075 (3.00 mg, 5.03 µmol, yield 16.17%, retention time: first peak) and compound WX-076 (3.00 mg, 5.19 µmol, yield 16.67%, retention time: second peak).

Referring to the synthesis method of steps 1-8 in embodiment 1, the embodiments in the following table were synthesized.

| Compound No. | structure | MS + 1 | $^1$HNMR (analysis) |
|---|---|---|---|
| WX-075 | (structure) | 579.1 | $^1$HNMR (400 MHz, METHANOL-$d_4$): δ 8.24 (s, 1H), 7.75 (d, J = 8.4 Hz, 1H), 7.30 (d, J = 8.4 Hz, 1H), 7.14-7.23 (m, 1H), 6.79 (d, J = 3.2 Hz, 1H), 6.62-6.53 (m, 3H), 5.12-5.25 (m, 1H), 4.14 (s, 1H), 3.82 (s, 3H), 3.76 (s, 3H), 3.50-3.52 (m, 4H), 3.03-3.19 (m, 3H), 2.83-2.97 (m, 2H). SFC method [column: OD (250 mm * 30 mm, 5 µm), mobile phase (A: $CO_2$, B: methanol containing 0.1 ammonium hydroxide, gradient: B 40%-40%)], retention time: first peak |

| Compound No. | structure | MS + 1 | ¹HNMR (analysis) |
|---|---|---|---|
| WX-076 | 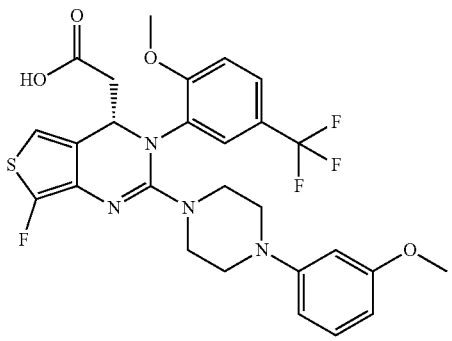 [SMILES: COc1cccc(N2CCN(C3=Nc4c(csc4F)[C@H](CC(=O)O)N3c3cc(C(F)(F)F)ccc3OC)CC2)c1] | 579.1 | ¹HNMR (400 MHz, METHANOL-d₄): δ 8.26 (s, 1H), 7.76 (d, J = 8.4 Hz, 1H), 7.30 (d, J = 8.4 Hz, 1H), 7.17-7.21 (m, 1H), 6.81 (d, J = 3.2 Hz, 1H), 6.52-6.58 (m, 3H), 5.19-5.22 (m, 1H), 4.15 (s, 1H), 3.83 (s, 3H), 3.78 (s, 3H), 3.52-3.68 (m, 4H), 3.05-3.16 (m, 3H), 2.88-2.94 (m, 2H). SFC method [column: (OD (250 mm * 30 mm, 5 µm), mobile phase (A: CO₂, B: methanol containing 0.1 ammonium hydroxide, gradient: B 40%-40%)], retention time: second peak |
| WX-097 | 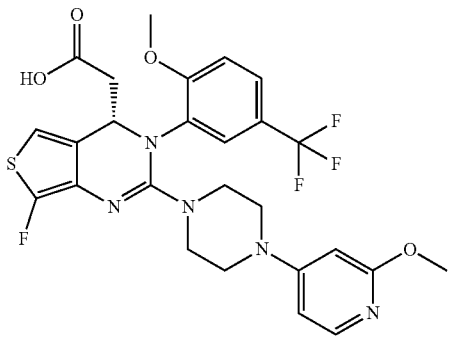 [SMILES: COc1cc(N2CCN(C3=Nc4c(csc4F)[C@H](CC(=O)O)N3c3cc(C(F)(F)F)ccc3OC)CC2)ccn1] | 580.1 | ¹HNMR (400 MHz, METHANOL-d₄) δ 7.74 (d, J = 6.5 Hz, 1H), 7.55 (d, J = 8.8 Hz, 1H), 7.22 (d, J = 8.0 Hz, 1H), 6.54 (dd, J = 2.1, 6.7 Hz, 1H), 6.45 (d, J = 3.5 Hz, 1H), 6.15 (d, J = 2.0 Hz, 1H), 4.85 (br. s., 1H), 3.88 (s, 6H), 3.36-3.58 (m, 4H), 3.16 (br. s., 3H), 2.92 (br. s., 1H), 2.57 (dd, J = 7.4, 14.7 Hz, 1H). SFC method [column: OD (250 mm * 30 mm, 5 µm), mobile phase (A: CO₂, B: isopropanol containing 0.1 ammonium hydroxide, gradient: B 25%-25%)], retention time: first peak |
| WX-098 | 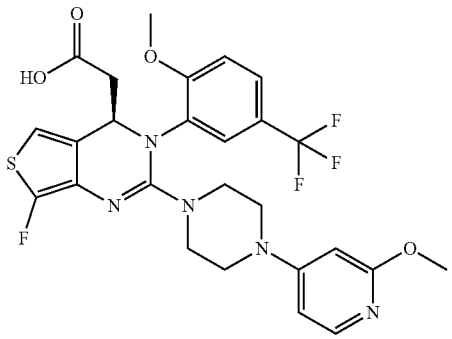 [SMILES: COc1cc(N2CCN(C3=Nc4c(csc4F)[C@@H](CC(=O)O)N3c3cc(C(F)(F)F)ccc3OC)CC2)ccn1] | 580.1 | ¹HNMR (400 MHz, METHANOL-d₄) δ 7.74 (d, J = 6.78 Hz, 1H), 7.56 (d, J = 8.53 Hz, 1H), 7.24 (d, J = 7.53 Hz, 1H), 6.64 (dd, J = 7.03, 2.26 Hz, 1H), 6.48 (d, J = 3.26 Hz, 1H), 6.25 (d, J = 2.26 Hz, 1H), 3.96 (s, 3H), 3.89 (br. s., 3H), 3.56 (br. s., 2H), 3.44 (d, J = 10.29 Hz, 5H), 2.93 (br. s., 1H), 2.60 (dd, J = 14.81, 7.28 Hz, 1H). SFC method [column: OD (250 mm * 30 mm, 5 µm), mobile phase (A: CO₂, B: isopropanol ontaining 0.1 ammonium hydroxide, gradient: B 25%-25%)], retention time: second peak |
| WX-099 | 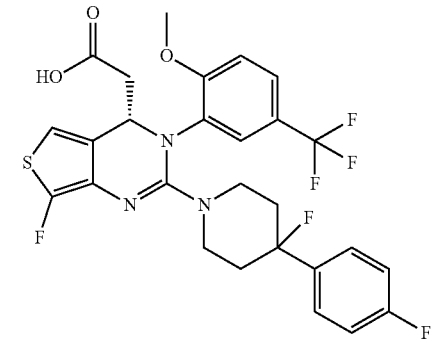 [SMILES: COc1ccc(C(F)(F)F)cc1N1C(N2CCC(F)(c3ccc(F)cc3)CC2)=Nc2c(csc2F)[C@@H]1CC(=O)O] | 584.1 | ¹HNMR (400 MHz, METHANOL-d₄) δ 7.63 (d, J = 8.8 Hz, 1H), 7.17-7.36 (m, 4H), 7.07 (t , J = 8.7 Hz, 2H), 6.53 (d, J = 2.8 Hz, 1H), 4.82-4.86 (m, 1H), 3.91 (br. s., 6H), 2.97 (br. s., 2H), 2.64 (dd, J = 7.5, 15.1 Hz, 1H), 1.50-2.14 (m, 4H). SFC method [column: OD (250 mm * 30 mm, 5 µm), mobile phase (A: CO₂, B: isopropanol containing 0.1 ammonium hydroxide, gradient: B 20%-20%)], retention time: first peak |

-continued

| Compound No. | structure | MS + 1 | ¹HNMR (analysis) |
|---|---|---|---|
| WX-100 | 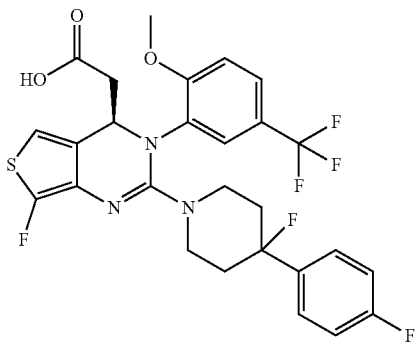 [SMILES: COc1ccc(C(F)(F)F)cc1N1C(N2CCC(F)(c3ccc(F)cc3)CC2)=Nc2c(csc2F)[C@H]1CC(=O)O] | 584.1 | ¹HNMR (400 MHz, METHANOL-$d_4$) δ 7.62 (d, J = 8.5 Hz, 1H), 7.17-7.35 (m, 4H), 7.06 (t, J = 8.8 Hz, 2H), 6.52 (br. s., 1H), 4.79-4.85 (m, 1H), 3.91 (br. s., 6H), 2.87-3.16 (m, 2H), 2.64 (dd, J = 7.5, 14.8 Hz, 1H), 1.58-2.12 (m, 4H). SFC method [column: OD (250 mm * 30 mm, 5 μm), mobile phase (A: $CO_2$, B: isopropanol containing 0.1 ammonium hydroxide, gradient: B 20%-20%)], retention time: second peak |
| WX-112 | 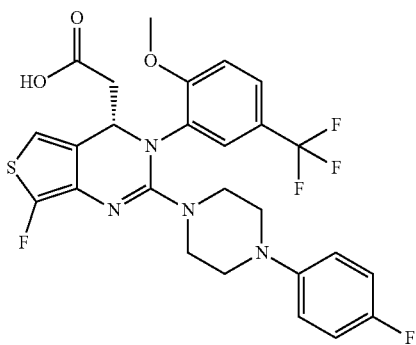 [SMILES: COc1ccc(C(F)(F)F)cc1N1C(N2CCN(c3ccc(F)cc3)CC2)=Nc2c(csc2F)[C@@H]1CC(=O)O] | 567.0 | ¹HNMR (400 MHz, METHANOL-$d_4$) δ 7.54 (d, J = 7.0 Hz, 1H), 7.22 (d, J = 8.8 Hz, 1H), 6.90-6.98 (m, 2H), 6.82-6.89 (m, 2H), 6.44 (d, J = 3.5 Hz, 1H), 4.79-4.84 (m, 1H), 3.84-3.94 (m, 3H), 3.47 (d, J = 18.8 Hz, 4H), 2.94 (d, J = 7.3 Hz, 1H), 2.86 (br. s., 2H), 2.70 (br. s., 1H), 2.56 (dd, J = 8.0, 14.8 Hz, 1H). SFC method [column: OD (250 mm * 30 mm, 5 μm), mobile phase (A: $CO_2$, B: isopropanol containing 0.1 ammonium hydroxide, gradient: B 30%-30%)], retention time: first peak |
| WX-113 | 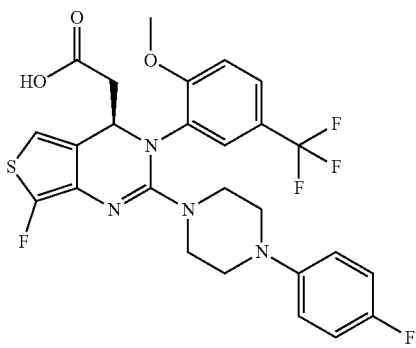 [SMILES: COc1ccc(C(F)(F)F)cc1N1C(N2CCN(c3ccc(F)cc3)CC2)=Nc2c(csc2F)[C@H]1CC(=O)O] | 567.0 | ¹HNMR (400 MHz, METHANOL-$d_4$) δ 7.54 (d, J = 8.8 Hz, 1H), 7.22 (d , J = 9.0 Hz, 1H), 6.89-6.96 (m, 2H), 6.83-6.88 (m, 2H), 6.44 (d, J = 3.3 Hz, 1H), 4.83 (br. s., 1H), 3.88 (br. s., 3H), 3.38-3.56 (m, 4H), 2.93 (br. s., 1H), 2.85 (d, J = 7.0 Hz, 2H), 2.70 (br. s., 1H), 2.56 (dd, J = 7.9, 14.7 Hz, 1H). SFC method [column: OD (250 mm * 30 mm, 5 μm), mobile phase (A: $CO_2$, B: isopropanol containing 0.1 ammonium hydroxide, gradient: B 30%-30%)], retention time: second peak |
| WX-127 | 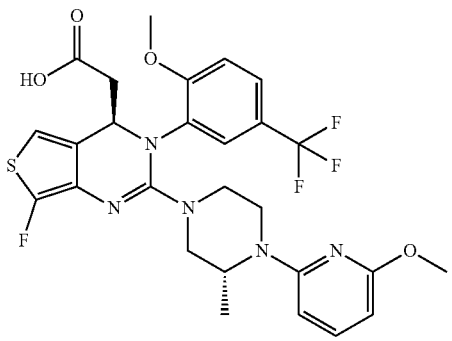 [SMILES: COc1cccc(N2CCN(C3=Nc4c(csc4F)[C@@H](CC(=O)O)N3c3cc(C(F)(F)F)ccc3OC)C[C@H]2C)n1] | 595.1 | ¹HNMR (400 MHz, METHANOL-$d_4$) δ 8.29 (br. s., 1H), 8.05 (d, J = 6.3 Hz, 1H), 7.74 (d, J = 7.8 Hz, 1H), 7.25 (d, J = 8.3 Hz, 1H), 6.79 (d, J = 3.3 Hz, 1H), 6.29 (d, J = 6.3 Hz, 1H), 5.18 (br. s., 1H), 4.60 (br. s., 1H), 4.06-4.34 (m, 2H), 3.97 (s, 3H), 3.45-3.81 (m, 6H), 3.06 (dd, J = 9.7, 16.4 Hz, 1H), 2.83-2.98 (m, 1H), 1.22 (br. s., 3H). SFC method [column: IC (250 mm * 30 mm, 10 μm), mobile phase (A: $CO_2$, B: methanol containing 0.1 ammonium hydroxide, gradient: B 25%-25%)], retention time: first peak |

| Compound No. | structure | MS + 1 | ¹HNMR (analysis) |
|---|---|---|---|
| WX-128 | 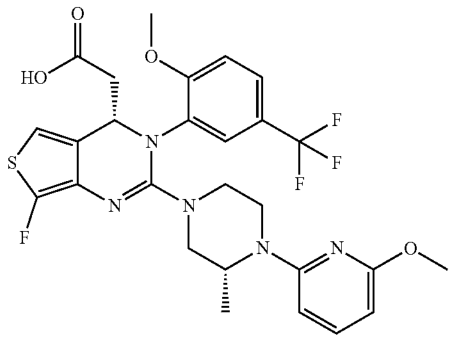 [SMILES: COc1cccc(N2CCN(C3=Nc4c(csc4F)[C@H](CC(=O)O)N3c3cc(C(F)(F)F)ccc3OC)C[C@H]2C)n1] | 595.1 | ¹HNMR (400 MHz, METHANOL-d₄) δ 8.31-8.22 (m, 1H), 8.06 (d, J = 6.5 Hz, 1H), 7.71 (d, J = 8.3 Hz, 1H), 7.25 (d, J = 8.0 Hz, 1H), 6.77 (d, J = 2.8 Hz, 1H), 6.35 (d, J = 6.5 Hz, 1H), 5.17 (br. s., 1H), 4.75 (br. s., 1H), 4.51 (d, J = 10.8 Hz, 1H), 4.05-4.19 (m, 1H), 3.99 (s, 3H), 3.52-3.93 (m, 6H), 3.00-3.16 (m, 1H), 2.81-2.97 (m, 1H), 0.83 (br. s., 3H). SFC method [column: IC (250 mm * 30 mm, 10 μm), mobile phase (A: CO₂, B: methanol containing 0.1 ammonium hydroxide, gradient: B 25%-25%)], retention time: second peak |
| WX-129 | 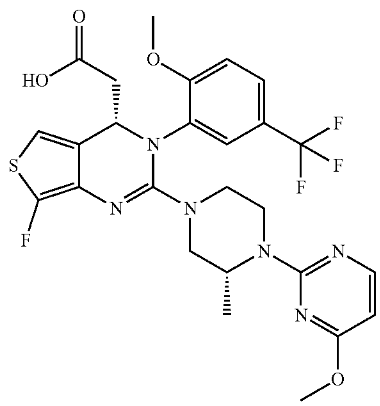 [SMILES: COc1ccnc(N2CCN(C3=Nc4c(csc4F)[C@H](CC(=O)O)N3c3cc(C(F)(F)F)ccc3OC)C[C@H]2C)n1] | 595.2 | ¹HNMR (400 MHz, METHANOL-d₄) δ 7.50 (dd, J = 1.6, 8.7 Hz, 1H), 7.37 (t, J = 7.9 Hz, 1H), 7.19 (br. s., 1H), 6.42 (d, J = 3.0 Hz, 1H), 6.15 (d, J = 8.0 Hz, 1H), 5.99 (d, J = 7.8 Hz, 1H), 4.78 (d, J = 7.8 Hz, 2H), 4.38 (br. s., 1H), 3.84-4.04 (m, 4H), 3.77 (s, 3H), 3.59-3.72 (m, 1H), 3.10 (dd, J = 2.9, 12.7 Hz, 1H), 2.81-2.99 (m, 3H), 2.55 (dd, J = 7.5, 14.6 Hz, 1H), 0.37 (br. s., 3H). SFC method [column: IC (250 mm * 30 mm, 10 μm), mobile phase (A: CO₂, B: methanol containing 0.1 ammonium hydroxide, gradient: B 25%-25%)], retention time: first peak |
| WX-130 | 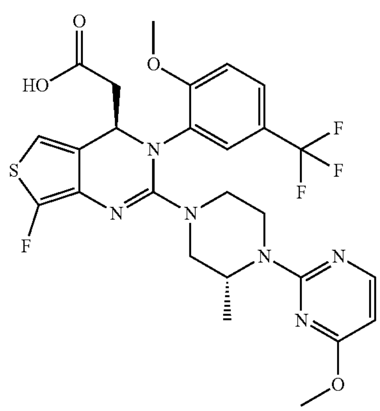 [SMILES: COc1ccnc(N2CCN(C3=Nc4c(csc4F)[C@@H](CC(=O)O)N3c3cc(C(F)(F)F)ccc3OC)C[C@H]2C)n1] | 595.2 | ¹HNMR (400 MHz, METHANOL-d₄) δ 7.58 (d, J = 8.5 Hz, 1H), 7.37 (t, J = 7.9 Hz, 1H), 7.22 (br. s., 1H), 6.47 (br. s., 1H), 6.09 (d, J = 8.3 Hz, 1H), 6.00 (d, J = 7.8 Hz, 1H), 4.75-4.86 (m, 2H), 4.33 (br. s., 1H), 3.63-3.99 (m, 8H), 3.13 (br. s., 2H), 2.97 (br. s., 1H), 2.59 (dd, J = 7.8, 15.1 Hz, 1H), 1.01 (d, J = 5.8 Hz, 3H). SFC method [column: IC (250 mm * 30 mm, 10 μm), mobile phase (A: CO₂, B: methanol containing 0.1 ammonium hydroxide, gradient: B 25%-25%)], retention time: second peak |
| WX-131 | 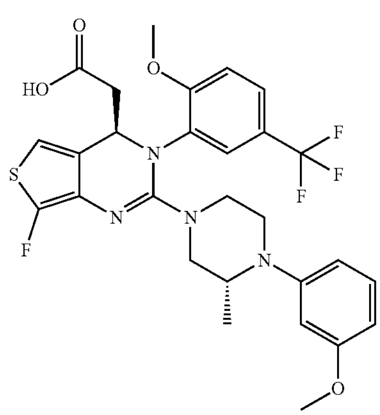 [SMILES: COc1cccc(N2CCN(C3=Nc4c(csc4F)[C@@H](CC(=O)O)N3c3cc(C(F)(F)F)ccc3OC)C[C@H]2C)c1] | 593.1 | ¹HNMR (400 MHz, METHANOL-d₄) δ 7.63 (d, J = 7.8 Hz, 1H), 7.26 (br. s., 1H), 7.11 (t, J = 8.2 Hz, 1H), 6.53 (br. s., 1H), 6.43 (dd, J = 3.0, 8.0 Hz, 2H), 6.35 (s, 1H), 4.80-4.88 (m, 1H), 3.66-4.01 (m, 7H), 3.49 (br. s., 3H), 3.05 (br. s., 2H), 2.64 (dd, J = 7.4, 15.4 Hz, 1H), 0.86 (d, J = 6.5 Hz, 3H). SFC method [column: OD (250 mm * 30 mm, 10 μm), mobile phase (A: CO₂, B: ethanol containing 0.1 ammonium hydroxide, gradient: B 25%-25%)], retention time: first peak |

| Compound No. | structure | MS + 1 | ¹HNMR (analysis) |
|---|---|---|---|
| WX-132 | 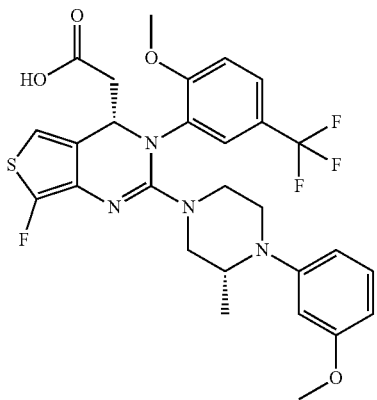 [SMILES: COc1cccc(N2CCN(C3=Nc4c(csc4F)[C@H](CC(=O)O)N3c3cc(C(F)(F)F)ccc3OC)C[C@H]2C)c1] | 593.1 | ¹HNMR (400 MHz, METHANOL-$d_4$) δ 7.49 (d, J = 7.3 Hz, 1H), 7.19 (br. s., 1H), 7.09 (t, J = 8.0 Hz, 1H), 6.46 (d, J = 7.8 Hz, 1H), 6.33-6.44 (m, 4H), 4.78 (br. s., 1H), 3.89 (br. s., 3H), 3.72 (s, 5H), 3.65 (br. s., 1H), 3.41 (br. s., 1H), 3.13 (t, J = 10.0 Hz, 1H), 2.77-3.06 (m, 3H), 2.52 (dd, J = 8.9, 14.9 Hz, 1H), 0.34 (br. s., 3H). SFC method [column: OD (250 mm * 30 mm, 10 μm), mobile phase (A: $CO_2$, B: ETHANOL CONTAINING 0.1 AMMONIUM HYDROXIDE, gradient: B 25%-25%)], retention time: second peak |
| WX-133 | 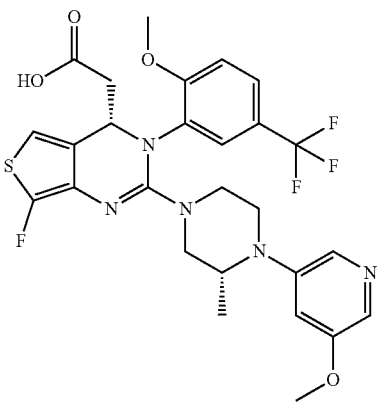 [SMILES: COc1cncc(N2CCN(C3=Nc4c(csc4F)[C@H](CC(=O)O)N3c3cc(C(F)(F)F)ccc3OC)C[C@H]2C)c1] | 594.1 | ¹HNMR (400 MHz, METHANOL-$d_4$) δ 7.75 (d, J = 2.0 Hz, 1H), 7.67 (d, J = 2.0 Hz, 1H), 7.51 (d, J = 8.3 Hz, 1H), 7.22 (br. s., 1H), 6.84 (s, 1H), 6.43 (d, J = 3.0 Hz, 1H), 4.80 (br. s., 1H), 4.61 (br. s., 1H), 3.81-3.98 (m, 9H), 3.55-3.67 (m, 1H), 3.25 (d, J = 9.8 Hz, 1H), 2.86-3.13 (m, 3H), 2.57 (br. s., 1H), 0.37 (br. s., 2H). SFC method [column: IC (250 mm * 30 mm, 10 μm), mobile phase (A: $CO_2$, B: ethanol containing 0.1 ammonium hydroxide, gradient: B 40%-40%)], retention time: first peak |
| WX-134 | 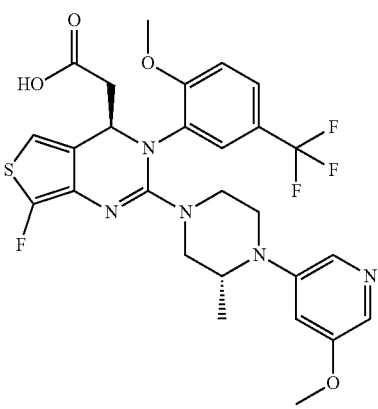 [SMILES: COc1cncc(N2CCN(C3=Nc4c(csc4F)[C@@H](CC(=O)O)N3c3cc(C(F)(F)F)ccc3OC)C[C@H]2C)c1] | 594.1 | ¹HNMR (400 MHz, METHANOL-$d_4$) δ 7.68 (dd, J = 2.1, 17.4 Hz, 2H), 7.56 (d, J = 8.5 Hz, 1H), 7.24 (br. s., 1H), 6.79 (s, 1H), 6.43 (d, J = 3.0 Hz, 1H), 4.80 (br. s., 1H), 4.61 (br. s., 1H), 3.7-4.06 (m, 9H), 3.65 (br. s., 1H), 3.09-3.27 (m, 3H), 2.98 (br. s., 1H), 2.49-2.61 (m, 1H), 0.95 (d, J = 6.3 Hz, 3H). SFC method [column: IC (250 mm * 30 mm, 10 μm), mobile phase (A: $CO_2$, B: ethanol containing 0.1 ammonium hydroxide, gradient: B 40%-40%)], retention time: second peak |

| Compound No. | structure | MS + 1 | ¹HNMR (analysis) |
| --- | --- | --- | --- |
| WX-145 | 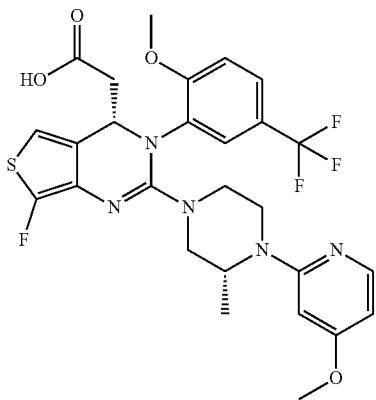 [SMILES: COc1ccnc(N2CCN(C3=Nc4c(csc4F)[C@H](CC(=O)O)N3c3cc(C(F)(F)F)ccc3OC)C[C@H]2C)c1] | 594.1 | ¹HNMR (400 MHz, METHANOL-$d_4$) δ 7.86 (d, J = 6.0 Hz, 1H), 7.49 (d, J = 8.5 Hz, 1H), 7.20 (br. s., 1H), 6.41 (d, J = 3.3 Hz, 1H), 6.32 (dd, J = 2.0, 6.0 Hz, 1H), 6.19 (d, J = 1.8 Hz, 1H), 4.78 (br. s., 1H), 4.30 (br. s., 1H), 3.87 (d, J = 9.3 Hz, 4H), 3.81 (s, 3H), 3.65 (br. s., 1H), 3.10 (dd, J = 3.6, 12.9 Hz, 1H), 2.92 (d, J = 8.3 Hz, 3H), 2.54 (dd, J = 8.2, 14.7 Hz, 1H), 0.36 (br. s., 3H). SFC method [column: IC (250 mm * 30 mm, 10 μm), mobile phase (A: $CO_2$, B: ethanol containing 0.1 ammonium hydroxide, gradient: B 40%-40%)], retention time: first peak |
| WX-146 | 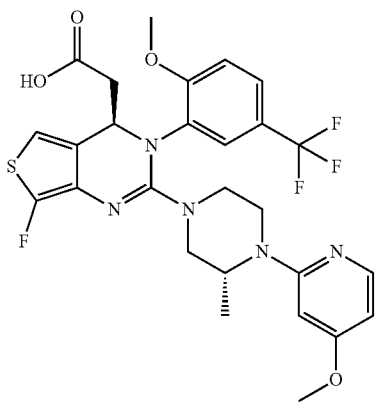 [SMILES: COc1ccnc(N2CCN(C3=Nc4c(csc4F)[C@@H](CC(=O)O)N3c3cc(C(F)(F)F)ccc3OC)C[C@H]2C)c1] | 594.1 | ¹HNMR (400 MHz, METHANOL-$d_4$) δ 7.84 (d, J = 6.3 Hz, 1H), 7.57 (d, J = 8.5 Hz, 1H), 7.23 (br. s., 1H), 6.45 (d, J = 3.5 Hz, 1H), 6.36 (dd, J = 2.1, 6.1 Hz, 1H), 6.19 (d, J = 1.8 Hz, 1H), 4.81 (br. s., 1H), 4.27 (br. s., 1H), 3.83 (s, 9H), 3.12 (d, J = 9.3 Hz, 2H), 2.96 (br. s., 1H), 2.57 (dd, J = 8.0, 15.3 Hz, 1H), 1.04 (d, J = 6.3 Hz, 3H). SFC method [column: IC (250 mm * 30 mm, 10 μm), mobile phase (A: CO2, B: ethanol containing 0.1 ammonium hydroxide, gradient: B 40%-40%)], retention time: second peak |
| WX-147 | 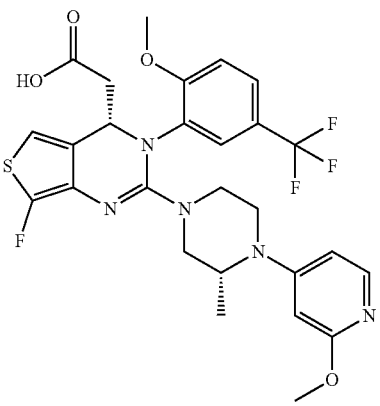 [SMILES: COc1cc(N2CCN(C3=Nc4c(csc4F)[C@H](CC(=O)O)N3c3cc(C(F)(F)F)ccc3OC)C[C@H]2C)ccn1] | 594.1 | ¹HNMR (400 MHz, METHANOL-$d_4$) δ 7.72 (d, J = 6.5 Hz, 1H), 7.49 (d, J = 7.3 Hz, 1H), 7.19 (br. s., 1H), 6.46 (dd, J = 2.1, 6.4 Hz, 1H), 6.40 (d, J = 3.5 Hz, 1H), 6.06 (d, J = 2.3 Hz, 1H), 4.78 (br. s., 1H), 3.78-4.07 (m, 8H), 3.63 (d, J = 8.3 Hz, 2H), 3.08 (dd, J = 3.6, 12.9 Hz, 1H), 2.91 (d, J = 8.5 Hz, 3H), 2.51 (dd, J = 8.3, 14.8 Hz, 1H), 0.36 (br. s., 3H). SFC method [column: IC (250 mm * 30 mm, 10 μm), mobile phase (A: $CO_2$, B: ethanol containing 0.1 ammonium hydroxide, gradient: B 40%-40%)], retention time: first peak |

| Compound No. | structure | MS + 1 | ¹HNMR (analysis) |
|---|---|---|---|
| WX-148 | 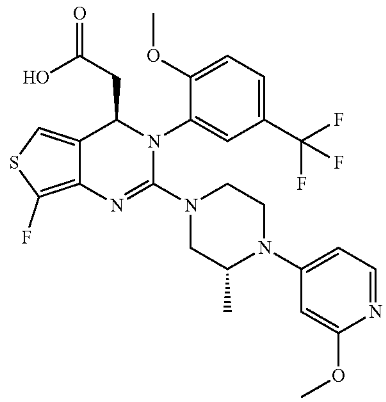 [SMILES: COc1cc(N2CCN(C3=Nc4c(csc4F)[C@@H](CC(=O)O)N3c3cc(C(F)(F)F)ccc3OC)C[C@H]2C)ccn1] | 594.1 | ¹HNMR (400 MHz, METHANOL-d₄) δ 7.74 (d, J = 7.0 Hz, 1H), 7.57 (d, J = 7.5 Hz, 1H), 7.24 (br. s., 1H), 6.60 (dd, J = 2.3, 7.0 Hz, 1H), 6.46 (d, J = 3.5 Hz, 1H), 6.18 (d, J = 2.0 Hz, 1H), 4.77-4.83 (m, 1H), 4.15 (br. s., 1H), 3.63-4.02 (m, 9H), 3.05-3.28 (m, 2H), 2.96 (br. s., 1H), 2.65-2.52 (m, 1H), 1.13 (d, J = 6.3 Hz, 3H). SFC method [column: IC (250 mm * 30 mm, 10 μm), mobile phase (A: $CO_2$, B: ethanol containing 0.1 ammonium hydroxide, gradient: B 40%-40%)], retention time: second peak |
| WX-149 | 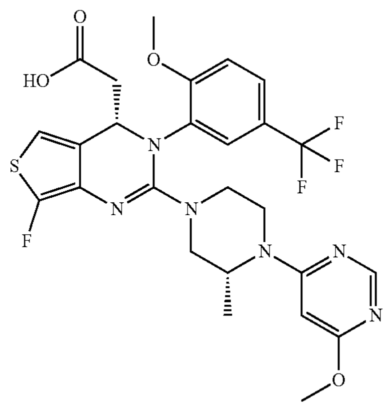 [SMILES: COc1cc(N2CCN(C3=Nc4c(csc4F)[C@H](CC(=O)O)N3c3cc(C(F)(F)F)ccc3OC)C[C@H]2C)ncn1] | 595.1 | ¹HNMR (400 MHz, METHANOL-d₄) δ 8.15 (s, 1H), 7.49 (d, J = 7.0 Hz, 1H), 7.19 (br. s., 1H), 6.40 (d, J = 3.3 Hz, 1H), 5.92 (s, 1H), 4.77 (br. s., 1H), 4.42 (br. s., 1H), 4.15 (d, J = 10.0 Hz, 1H), 3.73-4.01 (m, 7H), 3.63 (d, J = 12.8 Hz, 1H), 3.03 (dd, J = 3.6, 13.2 Hz, 1H), 2.81-2.97 (m, 3H), 2.50 (dd, J = 8.5, 14.8 Hz, 1H), 0.39 (br. s., 3H). SFC method [column: IC (250 mm * 30 mm, 10 μm), mobile phase (A: $CO_2$, B: ethanol containing 0.1 ammonium hydroxide, gradient: B 40%-40%)], retention time: first peak |
| WX-150 | 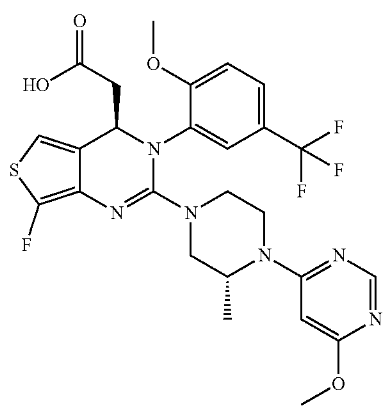 [SMILES: COc1cc(N2CCN(C3=Nc4c(csc4F)[C@@H](CC(=O)O)N3c3cc(C(F)(F)F)ccc3OC)C[C@H]2C)ncn1] | 595.1 | ¹HNMR (400 MHz, METHANOL-d₄) δ 8.17 (s, 1H), 7.60 (d, J = 8.5 Hz, 1H), 7.24 (br. s., 1H), 6.52 (br. s., 1H), 5.88 (s, 1H), 4.35 (br. s., 1H), 3.50-4.11 (m, 10H), 3.18 (d, J = 11.8 Hz, 2H), 2.98 (br. s., 2H), 2.64 (dd, J = 7.4, 15.2 Hz, 1H), 1.07 (d, J = 6.5 Hz, 3H). SFC method [column: IC (250 mm * 30 mm, 10 μm), mobile phase (A: $CO_2$, B: ethanol containing 0.1 ammonium hydroxide, gradient: B 40%-40%)], retention time: second peak |
| WX-151 | 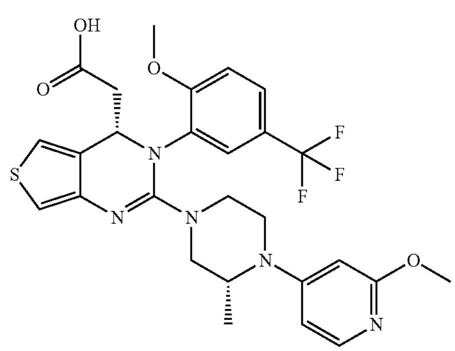 [SMILES: COc1cc(N2CCN(C3=Nc4cscc4[C@H](CC(=O)O)N3c3cc(C(F)(F)F)ccc3OC)C[C@H]2C)ccn1] | 576.2 | ¹HNMR (400 MHz, METHANOL-d₄) δ 7.74 (d, J = 6.27 Hz, 1H), 7.53 (br d, J = 8.53 Hz, 1H), 7.05-7.21 (m, 2H), 6.99 (br s, 1H), 6.47 (dd, J = 2.26, 6.53 Hz, 1H), 6.08 (d, J = 2.01 Hz, 1H), 5.00 (br s, 1H), 4.09 (br s, 1H), 3.61-3.99 (m, 8H), 3.26 (br s, 1H), 2.74-3.06 (m, 3H), 2.53 (dd, J = 7.28, 14.56 Hz, 1H), 0.51 (br s, 3H). SFC method [column: IC (250 mm * 30 mm, 10 μm), mobile phase (A: $CO_2$, B: ethanol containing 0.1 ammonium hydroxide, gradient: B 40%-40%)], retention time: first peak |

Embodiment 2
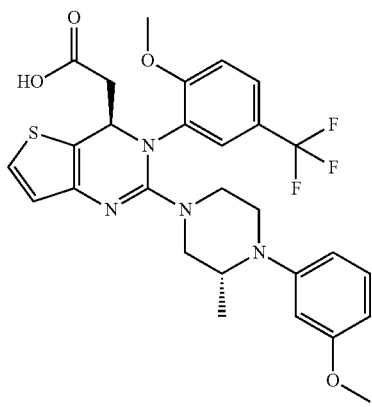
WX-135
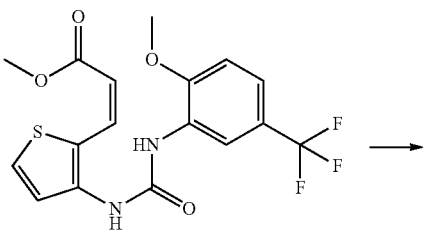
Synthetic Route:
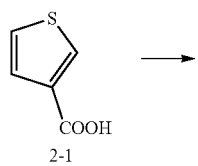
2-1
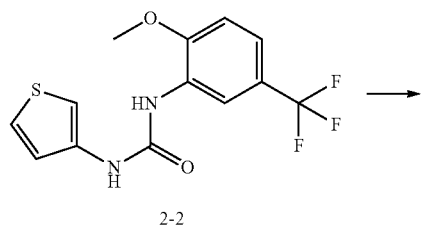
2-2
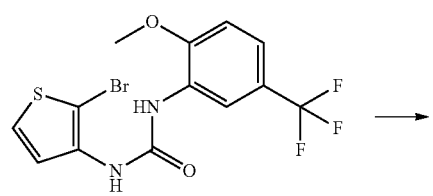
2-3
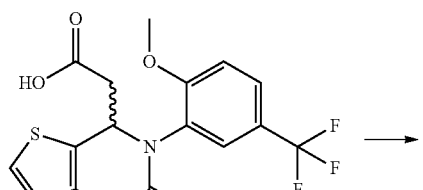
2-4
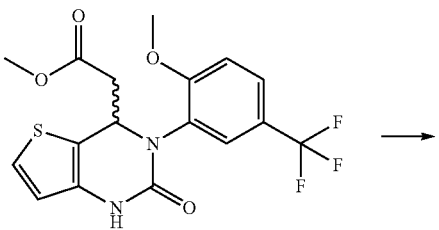
2-5
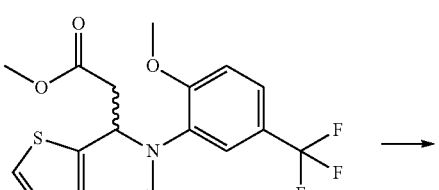
2-6
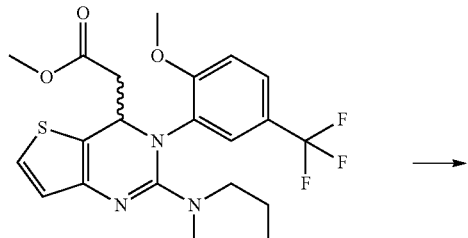
2-7
2-8

-continued

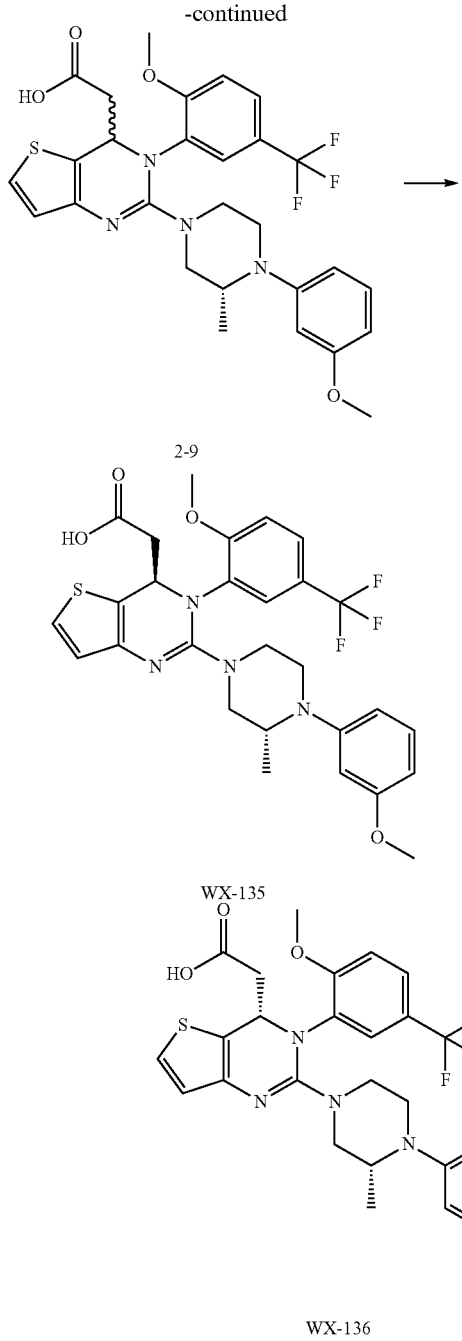

2-9

WX-135

WX-136

Step 1: Synthesis of Compound 2-2

To a solution of compound 2-1 (10.00 g, 78.03 mmol, 1.00 eq) and diphenyl azidophosphate (25.77 g, 93.64 mmol, 20.29 mL, 1.20 eq) in toluene (150.00 mL) was added Triethylamine (23.69 g, 234.09 mmol, 32.45 mL, 3.00 eq) at 15° C. The reaction solution was stirred under nitrogen atmosphere at 15° C. for 1.5 hours, then the reaction solution was heated to 80° C. and stirred for 7 hours, 2-Methoxy-5-trifluoromethyl aniline (15.66 g, 81.93 mmol, 1.05 eq) was added to the reaction solution and the reaction solution was stirred for 12 hours. Then the reaction solution was concentrated under reduced pressure and the residue was poured into HCl (1 N, 300 mL), the mixture was extracted with ethyl acetate (200 mL) twice. The combined organic phases were washed with brine, dried over anhydrous sodium sulfate and concentrated under reduced pressure, the residue was washed with PE:EtOAc (2:1) to give 2-2 (10.00 g, 24.41 mmol, yield 31.28%). $^1$HNMR (400 MHz, DMSO-d$_6$) δ 9.72 (s, 1H), 8.58 (s, 1H), 8.47 (s, 1H), 7.47-7.48 (m, 1H), 7.33-7.35 (m, 2H), 7.20 (d, J=8.4 Hz, 2H), 7.02 (d, J=5.2 Hz, 1H), 3.92 (s, 3H).

Step 2: Synthesis of Compound 2-3

To a solution of compound 2-2 (10.00 g, 31.62 mmol, 1.00 eq) in dichloromethane (150.00 mL) was added NBS (5.63 g, 31.62 mmol, 1.00 eq) at 0° C., the mixture was stirred at 0° C. for 2 hours. Then the reaction solution was filtered and the filter cake was dried to give 2-3 (6.80 g, 14.80 mmol, yield 46.80%). MS (ESI) m/z: 397.0 [M+1].

Step 3: Synthesis of Compound 2-4

To a solution of compound 2-3 (6.80 g, 17.21 mmol, 1.00 eq) and BB-11 (7.30 g, 34.42 mmol, 2.00 eq) in tetrahydrofuran (80.00 mL) and water (10.00 mL) was added Pd(dppf)Cl$_2$ (1.26 g, 1.72 mmol, 0.10 eq) and potassium carbonate (7.14 g, 51.63 mmol, 3.00 eq) at room temperature, the mixture was stirred under nitrogen atmosphere at 55° C. for 12 hours. Then the reaction solution was evaporated to dryness and the residue was purified by column chromatography (PE/EtOAc=5/1) to give 2-4 (2.60 g, 4.68 mmol, yield 27.17%). MS (ESI) m/z: 401.1 [M+1].

Step 4: Synthesis of Compound 2-5

To a solution of compound 2-4 (2.65 g, 6.62 mmol, 1.00 eq) in tetrahydrofuran (15.00 mL) was added aqueous solution of lithium hydroxide (1 M, 6.62 mL, 1.00 eq) at room temperature. Then the mixture was stirred at 40° C. for 12 hours. The reaction solution was evaporated to dryness to give a crude product of 2-5 (2.80 g).

Step 5: Synthesis of Compound 2-6

To a solution of compound 2-5 (6.80 g, 17.21 mmol, 1.00 eq) in methanol (60.00 mL) was added thionyl chloride (2.40 g, 20.19 mmol, 1.46 mL, 3.00 eq) at 0° C., the mixture was stirred under nitrogen atmosphere at 70° C. for 3 hours. Then the reaction solution was evaporated to dryness and the residue was purified by column chromatography (PE/EtOAc=3/1 to 3/2) to give compound 2-6 (800.00 mg, 1.58 mmol, yield 23.54%). $^1$HNMR: (400 MHz, CHLOROFORM-d) δ 7.59 (d, J=7.2 Hz, 1H), 7.16 (d, J=5.2 Hz, 1H), 7.05 (d, J=8.8 Hz, 1H), 6.57 (d, J=5.2 Hz, 1H), 5.40-5.43 (m, 1H), 3.89 (s, 3H), 3.57 (s, 3H), 2.75-2.81 (m, 2H).

Step 6: Synthesis of Compound 2-7

To a solution of compound 2-6 (6.80 g, 17.21 mmol, 1.00 eq) in phosphorus oxychloride (15.70 g, 102.39 mmol, 9.57 mL, 136.65 eq) was added N,N-Diisopropylethylamine (484.20 mg, 3.75 mmol, 654.33 μL, 5.00 eq) slowly at room temperature, the mixture was stirred under nitrogen atmosphere at 110° C. for 12 hours. Phosphorus pentachloride (468.11 mg, 2.25 mmol, 3.00 eq) was added to the reaction solution. The reaction solution was stirred under nitrogen atmosphere at 110° C. for 2 hours. Then the reaction solution was concentrated under reduced pressure, the residue was diluted with water, adjusted to neutral with sodium bicarbonate, extracted three times with ethyl acetate (100 mL), the combined organic phases was washed with brine, dried over anhydrous sodium sulfate, filtered and concentrated under reduced pressure to give a crude product of compound 2-7 (250.00 mg). MS (ESI) m/z: 419.1 [M+1].

Step 7: Synthesis of Compound 2-8

To a solution of compound 2-7 (200.00 mg, 477.53 μmol, 1.00 eq) and BB-1 (98.51 mg, 477.53 μmol, 1.00 eq) in acetonitrile (5.00 mL) was added potassium carbonate (659.99 mg, 4.78 mmol, 10.00 eq) at room temperature, the mixture was stirred at 80° C. for 12 hours. Then the reaction solution was filtered and the filter cake was dried to give a crude product of compound 2-8 (300.00 mg). MS (ESI) m/z: 589.2 [M+1].

Step 8: Synthesis of Compound 2-9

To a solution of compound 2-8 (300.00 mg, 509.65 μmol, 1.00 eq) in methanol (5.00 mL), tetrahydrofuran (5.00 mL) and water (3.00 mL) was added sodium hydroxide (61.16 mg, 1.53 mmol, 3.00 eq) at room temperature, the mixture was stirred for 12 hours. Then the reaction solution was evaporated to dryness, and the residue was purified by preparative HPLC to give compound 2-9 (50.00 mg, 66.85 μmol, yield 13.12%). MS (ESI) m/z: 575.2 [M+1].

Step 9: Synthesis of Compound WX-135 and WX-136

Compound 2-9 (50.00 mg, 81.82 μmol, 1.00 eq) was purified by preparative SFC [column: OD (250 mm*30 mm, 10 μm), mobile phase (A: $CO_2$, B: methanol containing 0.1 ammonium hydroxide, gradient: B 40%-40%)] to give compound WX-135 (11.00 mg, yield 21.76%, retention time: first peak) and compound WX-136 (6.00 mg, yield 12.76%, retention time: second peak).

Referring to the synthesis method of steps 1-9 in embodiment 2, the embodiments in the following table were synthesized.

| compound No. | Structure | MS + 1 | $^1$HNMR (analysis) |
|---|---|---|---|
| WX-135 | 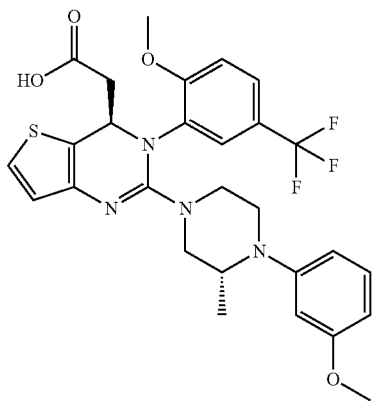 [SMILES: COc1cccc(N2CCN(C3=Nc4ccsc4[C@@H](CC(=O)O)N3c3cc(C(F)(F)F)ccc3OC)C[C@H]2C)c1] | 575.2 | $^1$HNMR (400 MHz, METHANOL-$d_4$) δ 8.19-8.36 (m, 1H), 7.99 (d, J = 8.0 Hz, 1H), 7.61 (d, J = 8.5 Hz, 1H), 7.26 (d, J = 5.0 Hz, 2H), 7.12 (t, J = 8.2 Hz, 1H), 6.95 (d, J = 5.3 Hz, 1H), 6.50-6.30 (m, 3H), 5.40-5.55 (m, 1H), 4.65 (br. s., 3H), 3.66-3.94 (m, 6H), 3.92-2.12 (m, 2H), 2.60 (dd, J = 8.8, 14.8 Hz, 1H), 1.32 (t, J = 7.3 Hz, 2H), 0.77-0.95 (m, 3H). SFC method [column: OD (250 mm * 30 mm, 10 μm), mobile phase (A: $CO_2$, B: methanol containing 0.1 ammonium hydroxide, gradient: B 40%-40%)], retention time: first peak |
| WX-136 | 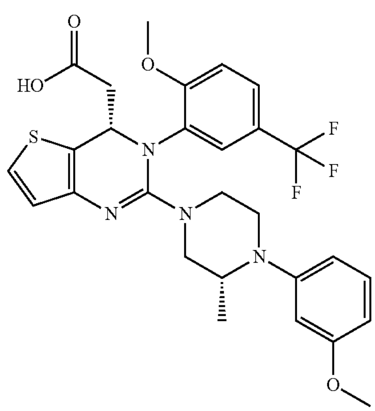 [SMILES: COc1cccc(N2CCN(C3=Nc4ccsc4[C@H](CC(=O)O)N3c3cc(C(F)(F)F)ccc3OC)C[C@H]2C)c1] | 575.2 | $^1$HNMR (400 MHz, METHANOL-$d_4$) δ 7.52 (d, J = 7.0 Hz, 1H), 7.21 (d, J = 5.3 Hz, 2H), 7.05-7.15 (m, 1H), 6.94 (d, J = 5.3 Hz, 1H), 6.36-6.54 (m, 3H), 4.65 (br. s., 2H), 3.79-4.05 (m, 3H), 3.64-3.77 (m, 5H), 3.43-3.54 (m, 1H), 3.03-3.19 (m, 2H), 2.82-2.91 (m, 1H), 2.59 (dd, J = 9.3,14.6 Hz, 1H), 1.24-1.41 (m, 3H), 0.39 (br. s., 2H). SFC method [column: OD (250 mm * 30 mm, 10 μm), mobile phase (A: $CO_2$, B: methanol containing 0.1 ammonium hydroxide, gradient: B 40%-40%)], retention time: second peak |
| WX-137 | 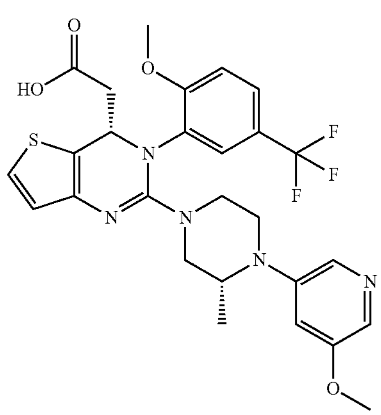 [SMILES: COc1cncc(N2CCN(C3=Nc4ccsc4[C@H](CC(=O)O)N3c3cc(C(F)(F)F)ccc3OC)C[C@H]2C)c1] | 576.2 | $^1$HNMR (400 MHz, METHANOL-$d_4$) δ 7.78 (d, J = 2.0 Hz, 1H), 7.71 (d, J = 2.0 Hz, 1H), 7.59 (d, J = 8.3 Hz, 1H), 7.16-7.42 (m, 2H), 7.01 (d, J = 5.3 Hz, 1H), 6.88 (t, J = 2.1 Hz, 1H), 5.10 (br. s., 1H), 3.75-4.02 (m, 7H), 3.63 (d, J = 12.8 Hz, 1H), 3.44 (br. s., 1H), 2.97-3.18 (m, 2H), 2.61-2.74 (m, 1H), 1.27-1.36 (m, 1H), 0.53 (br. s., 2H). SFC method [column: C2 (250 mm * 30 mm, 10 μm), mobile phase (A: $CO_2$, B: methanol containing 0.1 ammonium hydroxide, gradient: B 45%-45%)], retention time: first peak |

-continued

| compound No. | Structure | MS + 1 | ¹HNMR (analysis) |
|---|---|---|---|
| WX-138 | 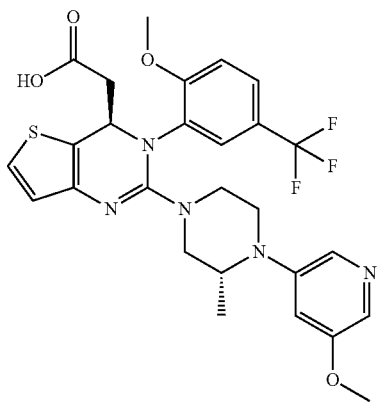 [SMILES: COc1cncc(N2CCN(C3=Nc4ccsc4[C@@H](CC(=O)O)N3c3cc(C(F)(F)F)ccc3OC)C[C@H]2C)c1] | 576.2 | ¹HNMR (400 MHz, METHANOL-$d_4$) δ 7.55-7.79 (m, 1H), 7.28 (d, J = 4.5 Hz, 1H), 6.96 (d, J = 5.3 Hz, 1H), 6.80 (s, 1H), 5.05 (br. s., 1H), 3.50-4.04 (m, 9H), 3.28 (br. s., 2H), 2.57-3.11 (m, 3H), 1.27-1.39 (m, 1H), 0.87-1.07 (m, 3H). SFC method [column: C2 (250 mm * 30 mm, 10 μm), mobile phase (A: $CO_2$, B: methanol containing 0.1 ammonium hydroxide, gradient: B 45%-45%)], retention time: second peak |
| WX-139 | 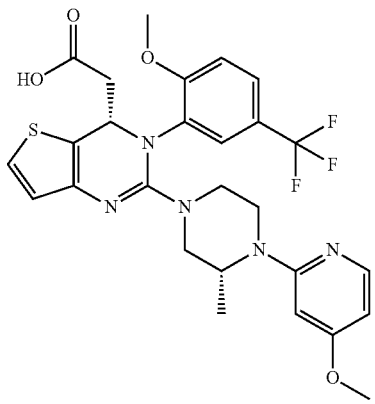 [SMILES: COc1ccnc(N2CCN(C3=Nc4ccsc4[C@H](CC(=O)O)N3c3cc(C(F)(F)F)ccc3OC)C[C@H]2C)c1] | 576.2 | ¹HNMR (400 MHz, METHANOL-$d_4$) δ 7.89 (d, J = 6.0 Hz, 1H), 7.57 (d, J = 7.5 Hz, 1H), 7.10-7.41 (m, 2H), 7.00 (d, J = 5.3 Hz, 1H), 6.34 (dd, J = 2.0, 6.0 Hz, 1H), 6.22 (d, J = 2.0 Hz, 1H), 5.08 (br. s., 1H), 4.39 (br. s., 1H), 4.04-3.65 (m, 9H), 3.00 (d, J = 9.8 Hz, 2H), 2.63 (dd, J = 7.7, 14.7 Hz, 1H), 0.53 (br. s., 3H). SFC method [column: AS (250 mm * 30 mm, 10 μm), mobile phase (A: $CO_2$, B: methanol containing 0.1 ammonium hydroxide, gradient: B 25%-25%)], retention time: first peak |
| WX-140 | 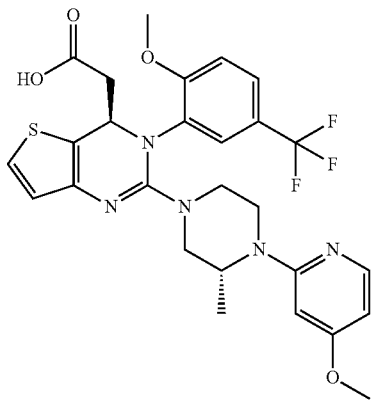 [SMILES: COc1ccnc(N2CCN(C3=Nc4ccsc4[C@@H](CC(=O)O)N3c3cc(C(F)(F)F)ccc3OC)C[C@H]2C)c1] | 576.2 | ¹HNMR (400 MHz, METHANOL-$d_4$) δ 7.82-7.94 (m, 1H), 7.57-7.72 (m, 1H), 7.42-7.08 (m, 2H), 6.90-7.05 (m, 1H), 6.28-6.42 (m, 1H), 6.04-6.18 (m, 1H), 5.01-5.18 (m, 1H), 3.51-3.99 (m, 9H), 2.96 (br. s., 2H), 2.63 (dd, J = 7.9, 14.7 Hz, 1H), 1.04 (d, J = 6.5 Hz, 3H). SFC method [column: AS (250 mm * 30 mm, 10 μm), mobile phase (A: $CO_2$, B: methanol containing 0.1 ammonium hydroxide, gradient: B 25%-25%)], retention time: second peak |

| compound No. | Structure | MS + 1 | ¹HNMR (analysis) |
|---|---|---|---|
| WX-141 | 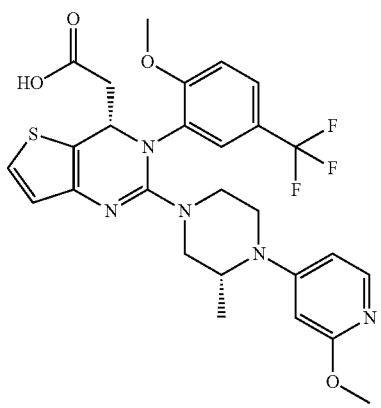 [SMILES: COc1cc(N2CCN(C3=Nc4ccsc4[C@H](CC(=O)O)N3c3cc(C(F)(F)F)ccc3OC)C[C@H]2C)ccn1] | 576.2 | ¹HNMR (400 MHz, METHANOL-$d_4$) δ 7.75 (br. s., 1H), 7.55 (d, J = 8.0 Hz, 1H), 7.12-7.38 (m, 2H), 6.98 (d, J = 5.0 Hz, 1H), 6.51 (br. s., 1H), 6.10 (br. s., 1H), 4.10 (br. s., 1H), 3.84 (s, 6H), 3.63-3.72 (m, 2H), 3.14-3.29 (m, 1H), 2.78-3.11 (m, 3H), 2.52-2.72 (m, 1H), 0.50 (br. s., 3H). SFC method [column: IC (250 mm * 30 mm, 10 μm), mobile phase (A: $CO_2$, B: methanol containing 0.1 ammonium hydroxide, gradient: B 40%-40%)], retention time: first peak |
| WX-142 | 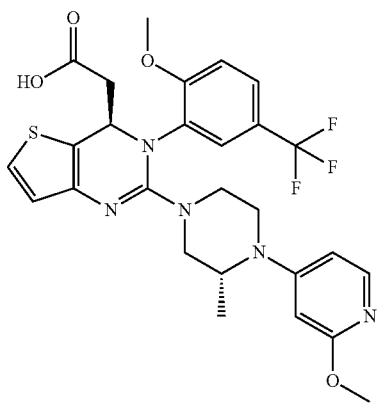 [SMILES: COc1cc(N2CCN(C3=Nc4ccsc4[C@@H](CC(=O)O)N3c3cc(C(F)(F)F)ccc3OC)C[C@H]2C)ccn1] | 576.2 | ¹HNMR (400 MHz, METHANOL-$d_4$) δ 7.76 (d, J = 5.8 Hz, 1H), 7.62 (d, J = 8.5 Hz, 1H), 7.14-7.41 (m, 2H), 6.98 (d, J = 5.3 Hz, 1H), 6.43 (d, J = 5.3 Hz, 1H), 6.01 (br. s., 1H), 3.96 (br. s., 1H), 3.63-3.87 (m, 6H), 3.54 (br. s., 1H), 2.82-3.12 (m, 2H), 2.63 (dd, J = 7.3, 14.6 Hz, 1H), 1.00-1.12 (m, 3H). SFC method [column: IC (250 mm * 30 mm, 10 μm), mobile phase (A: $CO_2$, B: methanol containing 0.1 ammonium hydroxide, gradient: B 40%-40%)], retention time: second peak |
| WX-143 | 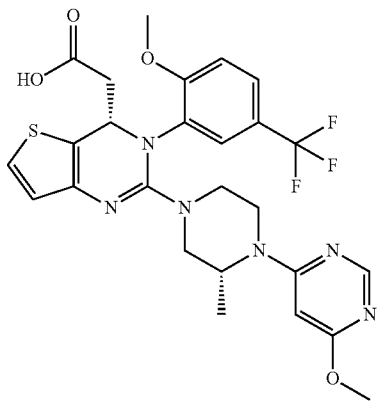 [SMILES: COc1cc(N2CCN(C3=Nc4ccsc4[C@H](CC(=O)O)N3c3cc(C(F)(F)F)ccc3OC)C[C@H]2C)ncn1] | 577.2 | ¹HNMR (400 MHz, METHANOL-$d_4$) δ 8.18 (s, 1H), 7.53 (d, J = 7.5 Hz, 1H), 7.24 (d, J = 5.0 Hz, 2H), 6.95 (d, J = 5.3 Hz, 1H), 5.96 (s, 1H), 4.63 (br. s., 1H), 4.47 (br. s., 1H), 4.20 (d, J = 12.0 Hz, 1H), 3.83-3.95 (m, 6H), 3.67 (d, J = 14.6 Hz, 1H), 3.13 (d, J = 15.6 Hz, 1H), 2.80-3.03 (m, 3H), 2.58 (dd, J = 8.7, 14.7 Hz, 1H), 0.48 (br. s., 3H). SFC method [column: IC (250 mm * 30 mm, 10 μm), mobile phase (A: $CO_2$, B: methanol containing 0.1 ammonium hydroxide, gradient: B 40%-40%)], retention time: first peak |

| compound No. | Structure | MS + 1 | ¹HNMR (analysis) |
|---|---|---|---|
| WX-144 | 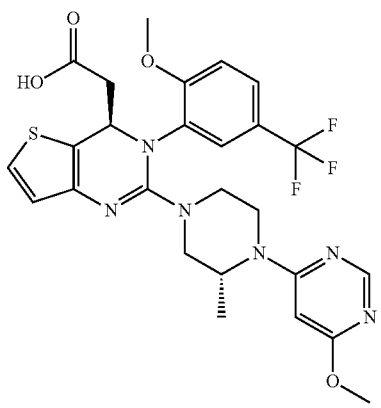 [SMILES: COc1cc(N2CCN(C3=Nc4ccsc4[C@@H](CC(=O)O)N3c3cc(C(F)(F)F)ccc3OC)C[C@H]2C)ncn1] | 577.2 | ¹HNMR (400 MHz, METHANOL-$d_4$) δ 8.18 (s, 1H), 7.59 (d, J = 9.0 Hz, 1H), 7.25 (br. s., 3H), 6.95 (d, J = 5.3 Hz, 1H), 5.88 (s, 1H), 4.63 (s, 1H), 4.36 (br. s., 1H), 3.88 (s, 7H), 3.70 (br. s., 1H), 2.87-3.23 (m, 4H), 2.60 (dd, J = 8.5, 14.6 Hz, 1H), 1.07-1.11 (m, 3H). SFC method [column: IC (250 mm * 30 mm, 10 μm), mobile phase (A: $CO_2$, B: methanol containing 0.1 ammonium hydroxide, gradient: B 40%-40%)], retention time: second peak |
| WX-087 | 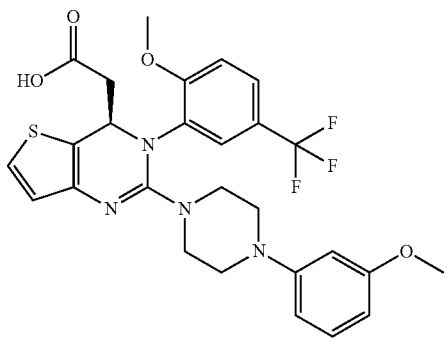 [SMILES: COc1cccc(N2CCN(C3=Nc4ccsc4[C@@H](CC(=O)O)N3c3cc(C(F)(F)F)ccc3OC)CC2)c1] | 561.2 | ¹HNMR (400 MHz, DMSO-$d_6$) δ 7.63 (s, 1H), 7.28-7.40 (m, 4H), 7.15-7.99 (m, 1H), 6.35-6.45 (m, 3H), 3.86 (s, 1H), 3.69 (s, 3H), 3.44 (s, 2H), 3.44 (s, 2H), 2.65 (d, J = 7.6 Hz, 2H). SFC method [column: AD (250 mm * 30 mm, 10 μm), mobile phase (A: $CO_2$, B: ethanol containing 0.1 ammonium hydroxide, gradient: B 40%-40%)], retention time: first peak |
| WX-088 | 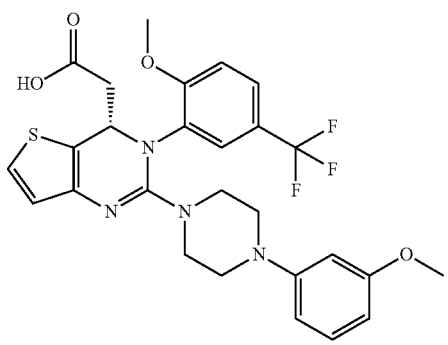 [SMILES: COc1cccc(N2CCN(C3=Nc4ccsc4[C@H](CC(=O)O)N3c3cc(C(F)(F)F)ccc3OC)CC2)c1] | 561.2 | ¹HNMR (400 MHz, DMSO-$d_6$) δ 7.54 (d, J = 8.8 Hz, 1H), 7.25 (d, J = 5.2 Hz, 2H), 7.08 (d, J = 8.0 Hz, 1H), 6.86 (d, J = 5.2 Hz, 1H), 6.43 (d, J = 9.2 Hz, 1H), 6.36 (d, J = 8.0 Hz, 1H), 3.89 (s, 2H), 3.69 (s, 3H), 2.0 (s, 3H). SFC method [column: AD (250 mm * 30 mm, 10 μm), mobile phase (A: $CO_2$, B: ethanol containing 0.1 ammonium hydroxide, gradient: B 40%-40%)], retention time: first peak |
| WX-089 | 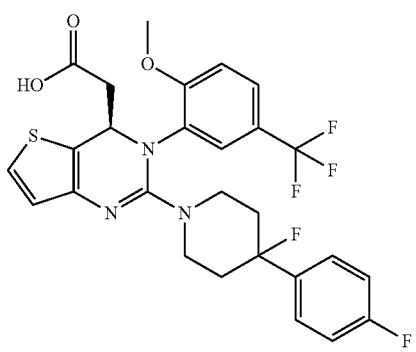 [SMILES: COc1ccc(C(F)(F)F)cc1N1C(N2CCC(F)(c3ccc(F)cc3)CC2)=Nc2ccsc2[C@H]1CC(=O)O] | 566.1 | ¹HNMR (400 MHz, METHANOL-$d_4$) δ 7.68 (d, J = 8.8 Hz, 1H), 7.29-7.38 (m, 4H), 7.00-7.12 (m, 3H), 5.14 (s, 3H), 4.63 (s, 2H), 3.95 (s, 2H), 3.05-3.15 (m, 2H), 2.64-2.71 (m, 1H), 1.97 (d, J = 19.2 Hz, 2H), 1.81 (s, 1H). SFC method [column: AD (250 mm * 30 mm, 10 μm), mobile phase (A: $CO_2$, B: ethanol containing 0.1 ammonium hydroxide, gradient: B 15%-15%)], retention time: first peak |

-continued

| compound No. | Structure | MS + 1 | ¹HNMR (analysis) |
|---|---|---|---|
| WX-090 | 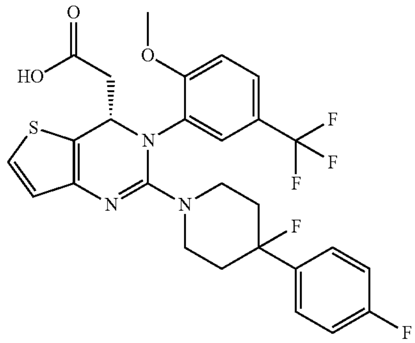 [SMILES: COc1ccc(C(F)(F)F)cc1N1C(N2CCC(F)(c3ccc(F)cc3)CC2)=Nc2ccsc2[C@@H]1CC(=O)O] | 566.1 | ¹HNMR (400 MHz, METHANOL-$d_4$) δ 7.67 (d, J = 8.4 Hz, 1H), 7.20-7.37 (m, 4H), 6.51 (t, J = 8.8 Hz, 2H), 6.99 (d, J = 4.8 Hz, 1H), 5.14 (s, 1H), 4.64 (s, 1H), 3.95 (s, 5H), 2.92-3.09 (m, 2H), 2.62-2.68 (m, 1H), 1.99 (t, J = 15.4 Hz, 2H), 1.82 (s, 1H). SFC method [column: AD (250 mm * 30 mm, 10 μm), mobile phase (A: $CO_2$, B: ethanol containing 0.1 ammonium hydroxide, gradient: B 15%-15%)], retention time: second peak |
| WX-108 | 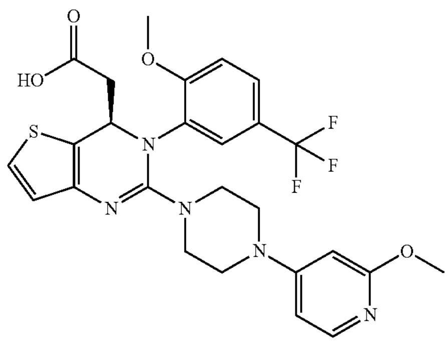 [SMILES: COc1cc(N2CCN(C3=Nc4ccsc4[C@@H](CC(=O)O)N3c3cc(C(F)(F)F)ccc3OC)CC2)ccn1] | 562.2 | ¹HNMR (400 MHz, METHANOL-$d_4$) δ 7.84-8.06 (m, 1H), 7.87 (d, J = 6.4 Hz, 1H), 7.65 (d, J = 8.4 Hz, 1H), 7.40 (d, J = 4.8 Hz, 1H), 7.01-7.12 (m, 1H), 6.51 (t, J = 4.0 Hz, 2H), 6.13 (d, J = 2.0 Hz, 1H), 5.18 (s, 6H), 3.86 (s, 6H), 3.59 (s, 6H), 3.49 (s, 4H), 3.22 (s, 2H), 2.90 (d, J = 3.6 Hz, 1H), 2.66-2.72 (m, 1H). SFC method [column: AD (250 mm * 30 mm, 10 μm), mobile phase (A: $CO_2$, B: ethanol containing 0.1 ammonium hydroxide, gradient: B 40%-40%)], retention time: first peak |
| WX-109 | 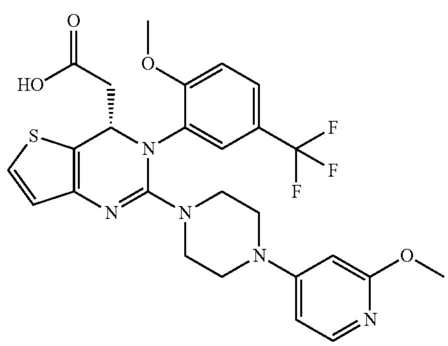 [SMILES: COc1cc(N2CCN(C3=Nc4ccsc4[C@H](CC(=O)O)N3c3cc(C(F)(F)F)ccc3OC)CC2)ccn1] | 562.2 | ¹HNMR (400 MHz, METHANOL-$d_4$) δ 7.78 (d, J = 6.4 Hz, 1H), 7.66 (d, J = 8.0 Hz, 1H), 7.42 (d, J = 4.8 Hz, 1H), 7.27 (s, 1H), 7.03 (d, J = 5.2 Hz, 1H), 6.54 (dd, J = 4.2 Hz, 1H), 6.14 (s, 1H), 5.20 (s, 1H), 3.94 (s, 6H), 3.50-3.63 (m, 5H), 3.38 (t, J = 8.6 Hz, 2H), 3.25 (s, 2H), 2.92 (d, J = 9.2 Hz, 1H). SFC method [column: AD (250 mm * 30 mm, 10 μm), mobile phase (A: $CO_2$, B: ethanol containing 0.1 ammonium hydroxide, gradient: B 40%-40%)], retention time: second peak |

Embodiment 3

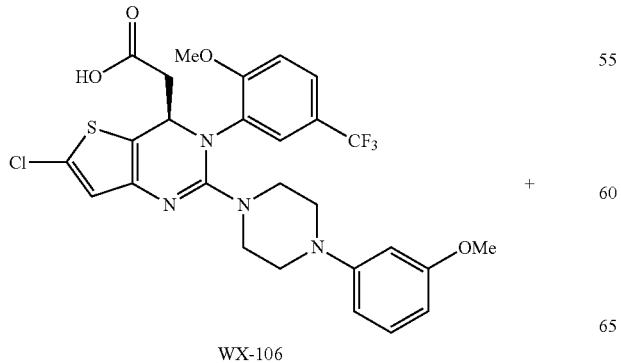

WX-106

+

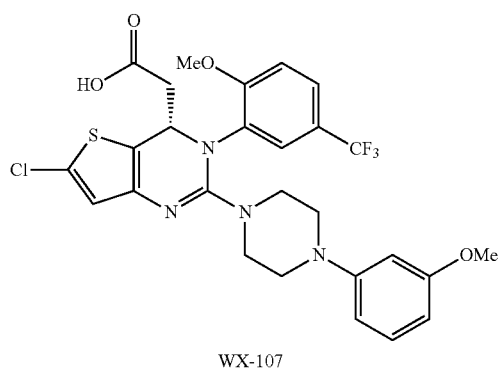

WX-107

Synthetic Route:

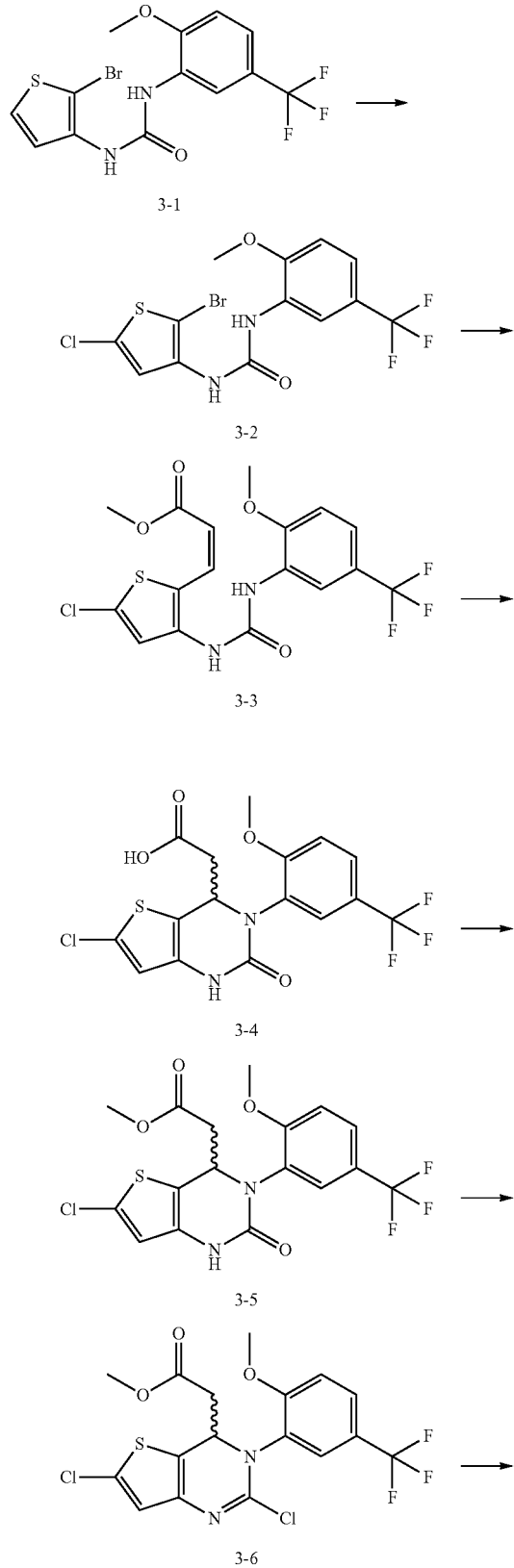

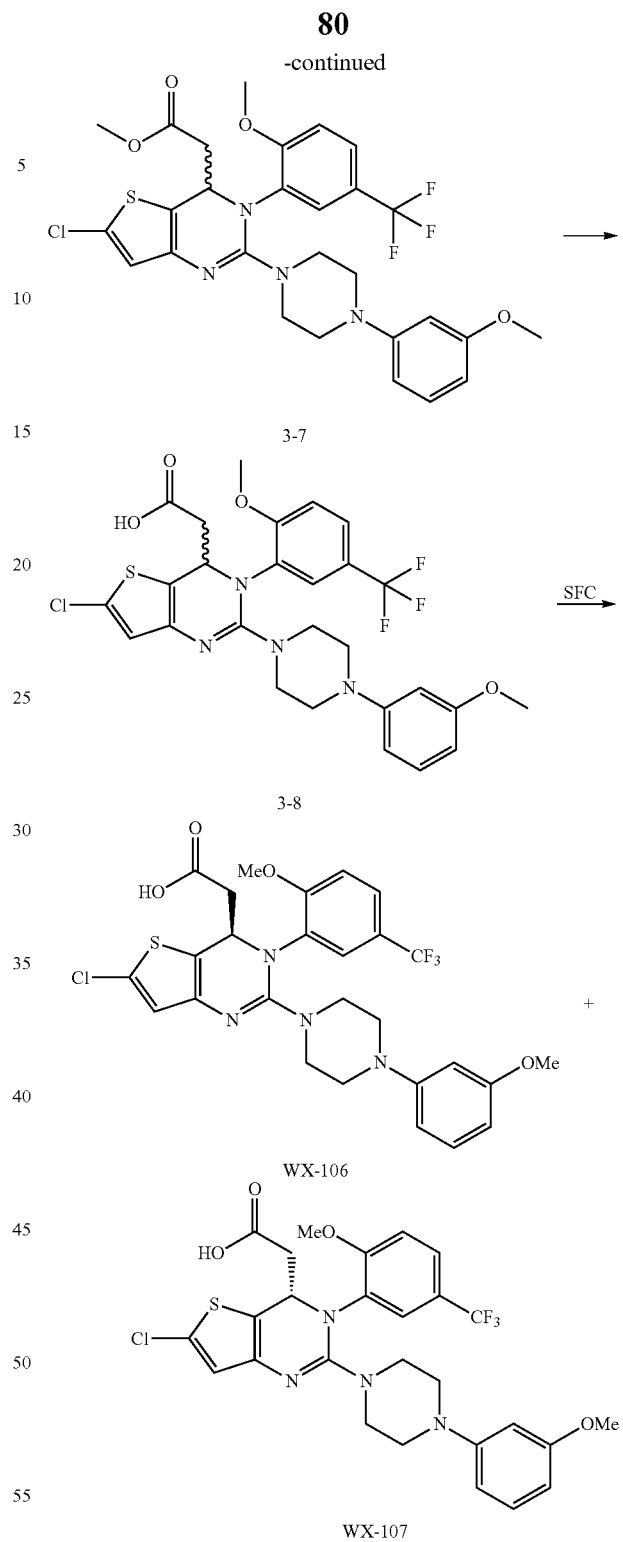

Step 1: Synthesis of Compound 3-2

To a solution of compound 3-1 (2.00 g, 5.06 mmol, 1.00 eq) in tetrahydrofuran (30.00 mL) was added NCS (1.01 g, 7.59 mmol, 1.50 eq) at 0° C., the reaction solution was evaporated to dryness, diluted with water (50 mL), extracted with ethyl acetate (50 mL) three times. The combined organic phases were washed with brine, dried over anhydrous sodium sulfate and filtered, the filtrate was evaporated to dryness to give 3-2 (2.00 g, 4.66 mmol, yield 92.00%).

¹HNMR: (400 MHz, DMSO-d₆) δ 9.02-9.40 (m, 2H), 8.49 (t, J=10.2 Hz, 1H), 7.58-7.66 (m, 1H), 7.31-7.34 (m, 2H), 7.19 (d, J=8.8 Hz, 1H), 3.89-4.00 (m, 3H).

Step 2: Synthesis of Compound 3-3

To a solution of compound 3-2 (1.00 g, 2.33 mmol, 1.00 eq) and BB-11 (988.15 mg, 4.66 mmol, 2.00 eq) in tetrahydrofuran (15.00 mL) and water (5.00 mL) was added Tripotassium phosphate trihydrate (1.86 g, 6.99 mmol, 3.00 eq) and Pd(dppf)Cl₂ (170.49 mg, 233.00 μmol, 0.10 eq) at room temperature, the mixture was stirred under nitrogen atmosphere at 55° C. for 12 hours. Then the reaction solution was evaporated under reduced pressure and the residue was purified by column chromatography (PE/EtOAc=5/1) to give compound 3-3 (300.00 mg, yield 17.47%). MS (ESI) m/z: 435.0 [M+1].

Step 3: Synthesis of Compound 3-4

To a solution of compound 3-3 (800.00 mg, 1.84 mmol, 1.00 eq) in tetrahydrofuran (10.00 mL) was added a solution of lithium hydroxide monohydrate (1 M, 1.29 mL, 0.70 eq) at room temperature, the mixture was stirred at 40° C. for 12 hours, and lithium hydroxide monohydrate (1 M, 5.52 mL, 3.00 eq) was added, the reaction solution was stirred at 40° C. for 4 hours, and then was evaporated to dryness to give a crude product of compound 3-4 (800.00 mg). MS (ESI) m/z: 421.0 [M+1].

Step 4: Synthesis of Compound 3-5

To a solution of compound 3-4 (800.00 mg, 1.90 mmol, 1.00 eq) in methanol (10.00 mL) was added thionyl chloride (678.55 mg, 5.70 mmol, 3.00 eq) at 0° C., the mixture was stirred under nitrogen atmosphere at 60° C. for 3 hours. Then the reaction solution was concentrated under reduced pressure and the residue was purified by preparative HPLC to give compound 3-5 (100.00 mg, yield 11.62%). MS (ESI) m/z: 435.0 [M+1].

Step 5: Synthesis of Compound 3-6

Compound 3-5 (50.00 mg, 114.99 μmol, 1.00 eq) was added to phosphorus oxychloride (12.46 g, 81.26 mmol, 706.69 eq) in batches at room temperature, followed by N,N-diisopropylethylamine (44.58 mg, 344.97 μmol, 3.00 eq) slowly at room temperature, the mixture was stirred at 100° C. under nitrogen atmosphere for 12 hours. Then the reaction solution was evaporated to give a crude product, which was added into water (40 mL) and adjusted to neutral with saturated sodium bicarbonate. The mixture was extracted twice with ethyl acetate (40 mL). The combined organic phases were washed with brine, dried over anhydrous sodium sulfate and concentrated under reduced pressure to give a crude product of compound 3-6 (50.00 mg). MS (ESI) m/z: 453.0 [M+1].

Step 5: Synthesis of Compound 3-7

To a solution of compound 3-6 (50.00 mg, 110.31 μmol, 1.00 eq) and BB-2 (63.63 mg, 330.94 μmol, 3.00 eq) in acetonitrile (3.00 mL) was added potassium carbonate (152.46 mg, 1.10 mmol, 10.00 eq) at room temperature, the mixture was stirred at 80° C. for 12 hours. Then the reaction solution was concentrated under reduced pressure to give a crude compound of compound 3-7 (150.00 mg), which was directly used in the next step. MS (ESI) m/z: 609.1[M+1].

Step 6: Synthesis of Compound 3-8

To a solution of compound 3-7 (100.00 mg, 164.19 μmol, 1.00 eq) in methanol (2.00 mL), tetrahydrofuran (2.00 mL) and water (1.00 mL) was added sodium hydroxide (19.70 mg, 492.57 μmol, 3.00 eq) at room temperature, the mixture was stirred at 10° C. for 2 hours. Then the reaction solution was evaporated and the residue was purified by preparative HPLC to give compound 3-8 (10.00 mg, yield 10.24%). MS (ESI) m/z: 595.1[M+1].

Step 7: Synthesis of Compound WX-106 and WX-107

Compound 3-8 (40.00 mg, 67.22 μmol, 1.00 eq) was purified by preparative SFC [column: IC (250 mm*30 mm, 10 μm), mobile phase (A: CO₂, B: ethanol containing 0.1 ammonium hydroxide, gradient: B 40%-40%)] to give compound WX-106 (13.00 mg, yield 28.34%) and WX-107 (10.00 mg, yield 21.48%).

| compound No. | Structure | MS + 1 | ¹HNMR (analysis) |
|---|---|---|---|
| WX-106 | 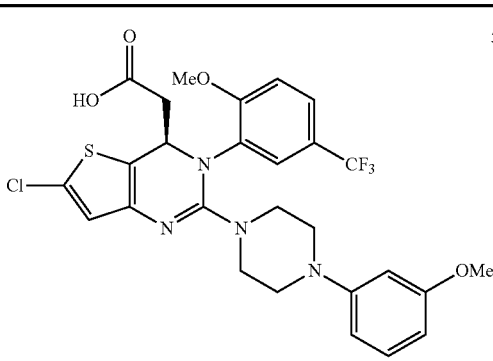 | 595.1 | ¹HNMR (400 MHz, METHANOL-d₄) δ 7.62 (d, J = 8.4 Hz, 1H), 7.28 (s, 1H), 7.75 (t, J = 8.4 Hz, 1H), 6.89 (s, 1H), 6.40-6.48 (m, 2H), 4.64 (s, 2H), 3.92 (s, 3H), 3.75 (s, 3H), 3.50 (d, J = 20 Hz, 4H), 2.97 (d, J = 7.6 Hz, 3H), 2.81 (s, 1H), 3.40 (t, J = 3.8 Hz, 1H). SFC method [column: IC (250 mm * 30 mm, 10 μm). mobile phase (A: CO₂, B: ethanol containing 0.1 ammonium hydroxide, gradient: B 40%-40%)], retention time: first peak |

-continued
| compound No. | Structure | MS + 1 | ¹HNMR (analysis) |
|---|---|---|---|
| WX-107 | 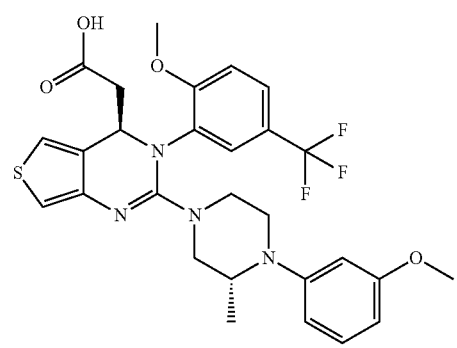 | 595.1 | ¹HNMR (400 MHz, METHANOL-d₄) δ 7.57 (d, J = 8.8 Hz, 1H), 7.26 (s, 1H), 7.11 (t, J = 8.0 Hz, 1H), 6.84 (s, 1H), 6.40-6.47 (m, 3H), 4.63 (s, 3H), 3.91 (s, 3H), 3.74 (s, 3H), 3.47 (d, J = 20.4 Hz, 3H), 2.94 (d, J = 7.6 Hz, 3H), 2.79 (s, 4H). SFC method [column: IC (250 mm * 30 mm, 10 μm), mobile phase (A: CO₂, B: ethanol containing 0.1 ammonium hydroxide, gradient: B 40%-40%)], retention time: second peak |
Embodiment 4
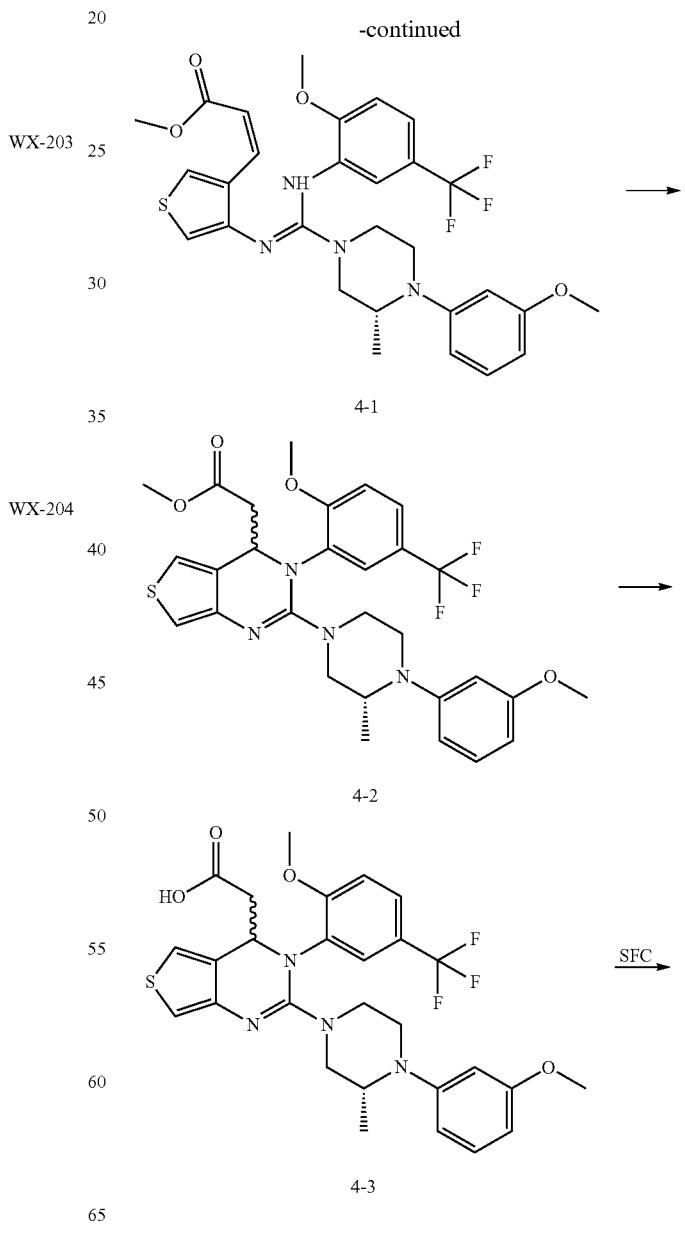
WX-203
WX-204
4-1
4-2
4-3
Synthetic Route:
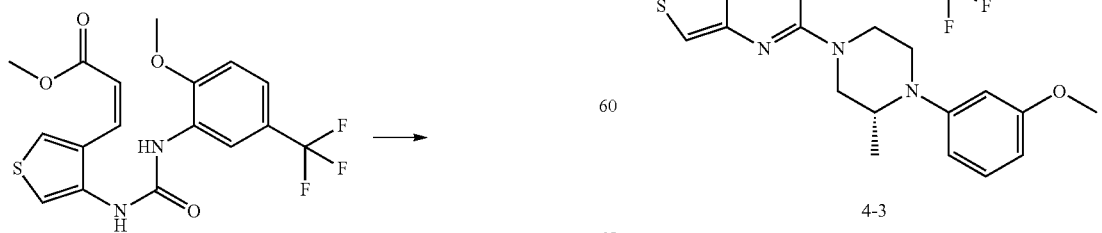
1-3

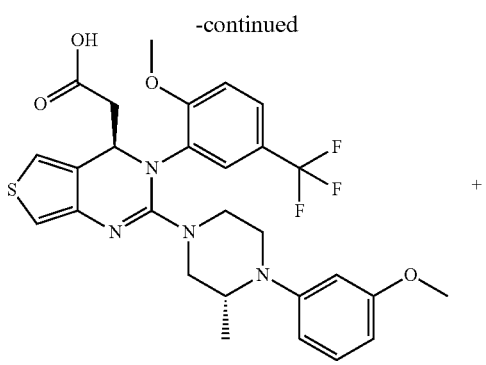

WX-203

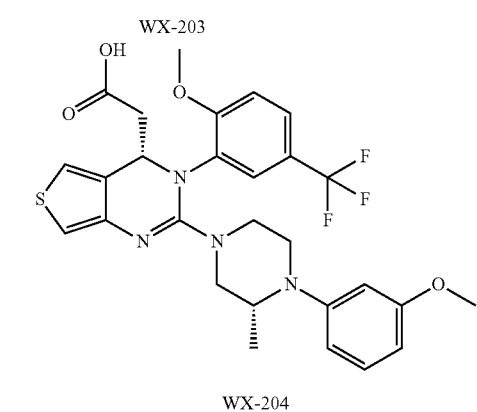

WX-204

Step 1: Synthesis of Compound 4-1 to a solution of compound 1-3 (5 g, 12.49 mmol, 1 eq) and 2,6-lutidine (8.03 g, 74.93 mmol, 8.73 mL, 6 eq) in toluene (150 mL) was added phosphorus pentachloride (7.80 g, 37.47 mmol, 3 eq) in batches under nitrogen atmosphere at 20° C., the mixture was heated to 50° C. and stirred for 2 hours. Then the reaction solution was cooled to 0° C., and adjusted to neutral with 2 M potassium hydroxide solution. The mixture was partitioned and the organic phase was washed with 1 M citric acid solution (100 mL) and brine (100 mL) respectively. Then compound BB-1 (3.35 g, 13.81 mmol, 1.1 eq, HCl), disodium phosphate (9.80 g, 69.05 mmol, 9.80 mL, 5.5 eq), triethylamine (3.49 g, 34.52 mmol, 4.81 mL, 2.75 eq) and water (50 mL) were added to the above organic phase respectively, the reaction solution was heated to 50° C. and stirred for 2 hours. Then the reaction solution was poured into water (150 mL) and partitioned. The aqueous phase was extracted with toluene (100 mL). The combined organic phases was washed with brine (200 mL), dried over anhydrous sodium sulfate to give a solution of compound 4-1 in toluene (about 250 mL), which was directly used in the next step.

MS (ESI) m/z: 589.2 [M+1].

Step 2: Synthesis of Compound 4-2

To the solution of compound 4-1 in toluene (about 250 mL) obtained in step 1 was added DBU (11.42 g, 74.99 mmol, 11.30 mL, 6.0 eq) at room temperature, the mixture was stirred at 110° C. for 12 hours. Then the reaction solution was purified by silica gel column chromatography (PE/EtOAc=10/1 to 2/1) to give compound 4-2 (4.7 g, 7.98 mmol, yield 69.42% for steps 1-2).

MS (ESI) m/z: 589.2 [M+1].

Step 3: Synthesis of Compound 4-3

To a solution of compound 4-2 (4.7 g, 7.98 mmol, 1 eq) in MeOH (100 mL) and water (20 mL) was added sodium hydroxide (3.19 g, 79.85 mmol, 10 eq), the reaction solution was stirred at 70° C. for 3 hours. Then the reaction solution was concentrated to remove most of the methanol, then water (20 mL) was added. The mixture was extracted twice with MTBE (30 mL). The aqueous phase was adjusted pH 6 with 1 M hydrochloric acid and then extracted with ethyl acetate (30 mL) twice. The organic phases were combined, washed with brine (50 mL), dried over anhydrous sodium sulfate, filtered and concentrated to give compound 4-3 (2 g, 3.20 mmol, yield 40.10%, purity 92%). MS (ESI) m/z: 575.2 [M+1].

Step 4: Synthesis of Compound WX-203 and WX-204

Compound 4-3 (2 g, 3.20 mmol, 1.00 eq) was purified by preparative SFC [column: IC-H (250 mm*30 mm, 5 μm), mobile phase (A: $CO_2$, B: methanol containing 0.1 ammonium hydroxide, gradient: B 30%-30%)] to give compound WX-203 (600 mg, yield 29.40%, retention time: first peak) and WX-204 (900 mg, yield 44.10%, second peak). MS (ESI) m/z: 575.2[M+1].

Referring to the synthesis method of steps 1-4 in embodiment 4, compound WX-198 and WX-199 in the following table were synthesized.

| compound No. | Structure | MS + 1 | $^1$HNMR (analysis) |
|---|---|---|---|
| WX-198 | 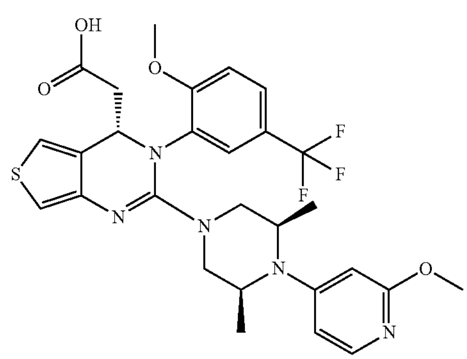 [SMILES: COc1cc(N2[C@H](C)CN(C3=Nc4cscc4[C@H](CC(=O)O)N3c3cc(C(F)(F)F)ccc3OC)C[C@@H]2C)ccn1] | 590.2 | $^1$HNMR (400 MHz, CHLOROFORM-d) δ 7.89-7.85 (m, 1H), 7.42 (br s, 1H), 7.04-6.92 (m, 2H), 6.79 (br s, 1H), 6.22 (br d, J = 4.0 Hz, 1H), 5.88 (br s, 1H), 4.92 (br s, 1H), 3.99-3.87 (m, 6H), 3.74-3.60 (m, 5H), 3.06 (br s, 3H), 2.72 (br s, 1H), 1.04 (br s, 3H), 0.36 (br s, 3H). SFC method [column: IC-H (250 mm * 30 mm, 5 μm), mobile phase (A: $CO_2$, B: methanol containing 0.1 ammonium hydroxide, gradient: B 30%-30%)], retention time: first peak |

| compound No. | Structure | MS + 1 | ¹HNMR (analysis) |
|---|---|---|---|
| WX-199 | 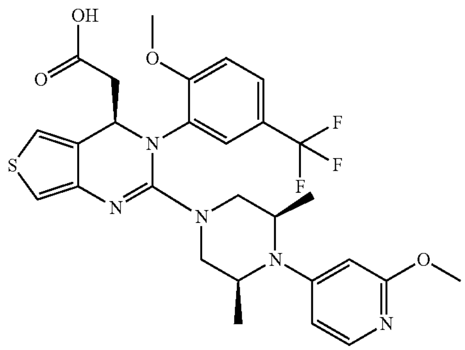 [SMILES: COc1cc(N2[C@H](C)CN(C3=Nc4cscc4[C@@H](CC(=O)O)N3c3cc(C(F)(F)F)ccc3OC)C[C@@H]2C)ccn1] | 590.2 | ¹HNMR (400 MHz, CHLOROFORM-d) δ 7.87 (d, J = 6.4 Hz, 1H), 7.34 (d, J = 6.4 Hz, 1H), 7.05-6.92 (m, 3H), 6.76 (d, J = 2.4 Hz, 1H), 6.22 (br d, J = 4.4 Hz, 1H), 5.89 (s, 1H), 4.94 (br s, 1H), 4.02-3.88 (m, 6H), 3.74 (br s, 2H), 3.67 (s, 1H), 3.56 (s, 2H). 3.08-3.05 (m, 2H), 2.75-2.72 (m, 1H), 1.04 (br s, 3H), 0.35 (br s, 3H). SFC method [column: IC-H (250 mm * 30 mm, 5 μm), mobile phase (A: CO₂, B: ethanol containing 0.1 ammonium hydroxide, gradient: B 30%-30%)], retention time: second peak |
| WX-203 | 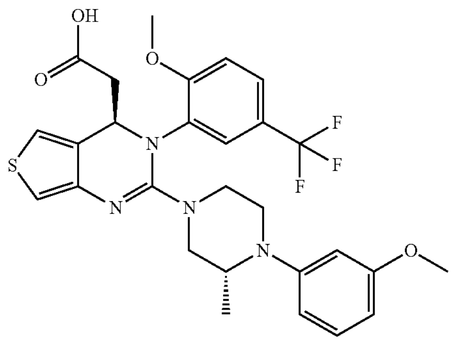 [SMILES: COc1cccc(N2CCN(C3=Nc4cscc4[C@@H](CC(=O)O)N3c3cc(C(F)(F)F)ccc3OC)C[C@H]2C)c1] | 575.2 | ¹HNMR (400 MHz, CHLOROFORM-d) δ 7.49 (br d, J = 8.4 Hz, 1H), 7.17-7.15 (m, 2H), 6.96 (s, 1H), 7.03 (s, 1H), 6.65 (d, J = 2.8 Hz, 1H), 6.42-6.36 (m, J = 8.4 Hz, 2H), 6.29 (br s, 1H), 5.03-4.99 (m, 1H), 3.94-3.76 (m, 7H), 3.58-3.50 (m, 2H), 3.20-3.04 (m, 4H), 2.72-2.66 (m, 2H), 0.88 (br d, J = 6.4 Hz, 3H). SFC method [column: OD-H (250 mm * 30 mm, 5 μm), mobile phase (A: CO₂, B: methanol containing 0.1 ammonium hydroxide, gradient: B 42%-42%)], retention time: first peak |
| WX-204 | 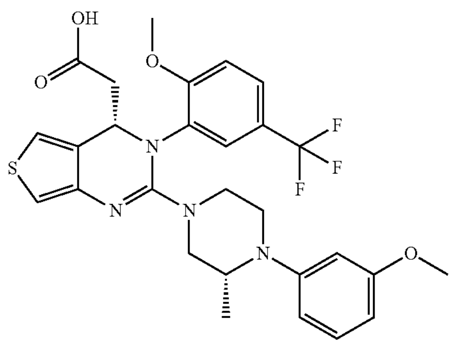 [SMILES: COc1cccc(N2CCN(C3=Nc4cscc4[C@H](CC(=O)O)N3c3cc(C(F)(F)F)ccc3OC)C[C@H]2C)c1] | 575.2 | ¹HNMR (400 MHz, CHLOROFORM-d) δ 7.64 (br s, 1H), 7.43 (br d, J = 8.4 Hz, 1H), 7.15-7.11 (m, 1H), 6.99-6.93 (m, 2H), 6.92 (s, 1H), 6.43 (br d, J = 8 Hz, 2H), 6.35 (s, 1H), 4.98 (br s, 1H), 3.90-3.75 (m, 7H), 3.59 (br s, 1H), 3.39 (br s, 2H), 3.18-3.02 (m, 3H), 2.89-2.84 (m, 1H), 2.73-2.68 (m, 1H), 0.39 (br s, 3H). SFC method [column: OD-H (250 mm * 30 mm, 5 μm), mobile phase (A: CO₂, B: methanol containing 0.1 ammonium hydroxide, gradient: B 42%-42%)], retention time: second peak |

Embodiment 5

WX-200

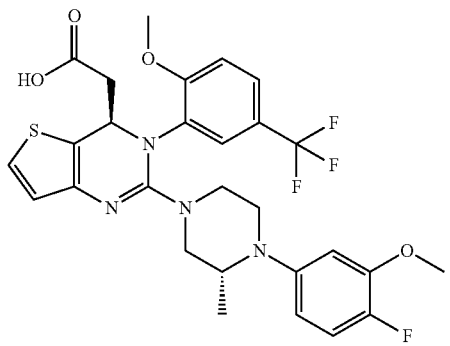

WX-201

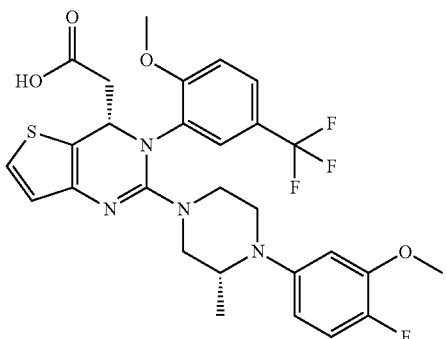

Synthetic Route:

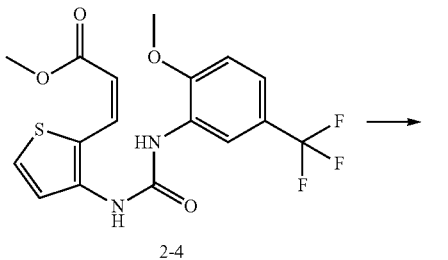

2-4

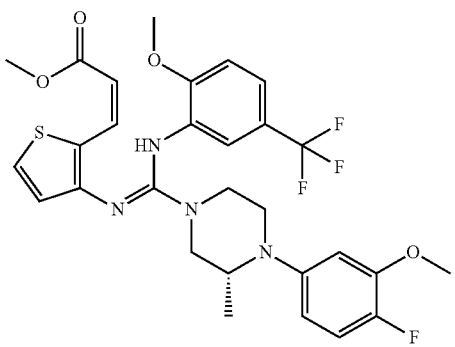

5-1

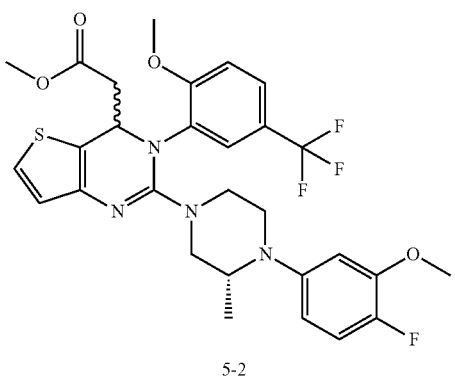

5-2

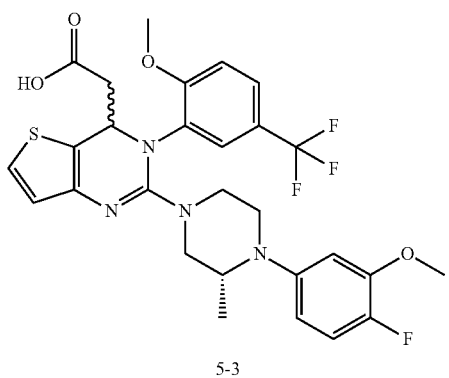

5-3

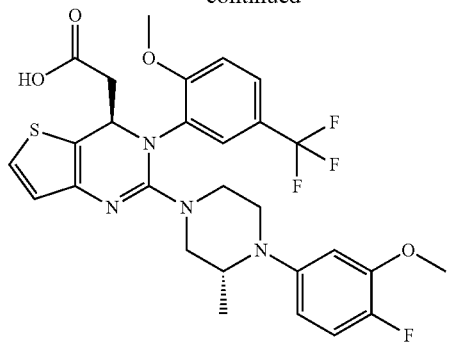

WX-200

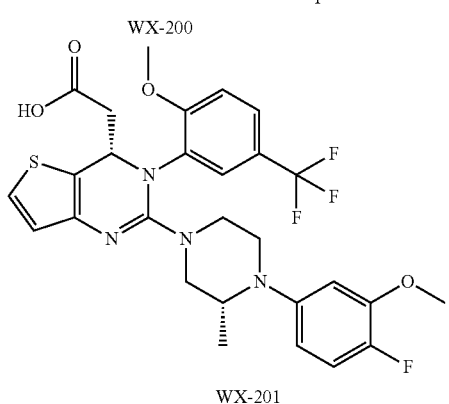

WX-201

Step 1: Synthesis of Compound 5-1

To a solution of compound 2-4 (1 g, 2.50 mmol, 1 eq) and 2,6-lutidine (1.61 g, 14.99 mmol, 1.75 mL, 6 eq) in toluene (20 mL) was added phosphorus pentachloride (1.56 g, 7.49 mmol, 3 eq) in batches under nitrogen atmosphere at 20° C., the mixture was heated to 50° C. and stirred for 1 hour. Then the reaction solution was cooled to 0° C., and adjusted to neutral with 2 M potassium hydroxide solution. The mixture was partitioned and the aqueous phase was extracted twice with toluene (5 mL), the combined organic phases were washed with citric acid solution (1 M, 30 mL) and brine (30 mL) respectively. Then Compound BB-13 (749.61 mg, 2.88 mmol, 1.15 eq, HCl), disodium phosphate (2.13 g, 15.00 mmol, 2.13 mL, 6 eq), triethylamine (758.93 mg, 7.50 mmol, 1.04 mL, 3 eq) and water (5 mL) were added to the above solution respectively at room temperature, the reaction solution was heated to 50° C. and stirred for 1 hour. Then the reaction solution was poured into water (20 mL) and partitioned, the aqueous phase was extracted with toluene (5 mL) twice. The combined organic phases were washed with brine (5 mL), dried over anhydrous sodium sulfate to give a solution of compound 5-1 in toluene (about 40 mL), which was directly used in the next step. MS (ESI) m/z: 607.2 [M+1].

Step 2: Synthesis of Compound 5-2

DBU (2.28 g, 15.00 mmol, 2.26 mL, 6 eq) was added to the solution of compound 5-1 in toluene (about 40 mL) obtained in step 1 at 20° C., the mixture was stirred at 110° C. for 2 hours. Then the reaction solution was concentrated and the residue was purified by silica gel column (PE: EtOAc=10:1 to 2:1) to give compound 5-2 (0.6 g, 865.44 μmol, purity 87.5%, yield 34.62% for steps 1-2).

MS (ESI) m/z: 607.3 [M+1].

Step 3: Synthesis of Compound 5-3

To a solution of compound 5-2 (0.6 g, 865.44 μmol, 1 eq) in MeOH (12 mL) and water (4 mL) was added sodium hydroxide (395.63 mg, 9.89 mmol, 11 eq) at room temperature, the mixture was stirred at 70° C. for 2 hours. Then the reaction solution was concentrated to remove most of the methanol, then water (20 mL) was added. The mixture was extracted with ethyl acetate (20 mL). The aqueous phase was adjusted pH 7 with 1 M hydrochloric acid and then extracted twice with ethyl acetate (30 mL), the combined organic phases were washed with brine (50 mL), dried over anhydrous sodium sulfate, filtered and concentrated to give compound 5-3 (0.5 g, 0.75 mmol, yield 86.8%, purity 89%). $^1$HNMR (400 MHz, METHANOL-$d_4$) δ ppm 7.55-7.47 (m, 1H), 7.18-7.30 (m, 2H), 6.86-6.91 (m, 2H), 6.54-6.60 (m, 1H), 6.31-6.48 (m, 1H), 4.91-4.95 (m, 1H), 3.90 (br s, 3H), 3.80 (s, 3H), 3.71 (d, J=4.0 Hz, 3H), 3.58 (br s, 1H), 3.46 (br s, 1H), 2.99-3.11 (m, 1H), 2.63-2.94 (m, 3H), 0.76 (d, J=6.4 Hz, 1H), 0.45 (br s, 1H). MS (ESI) m/z: 593.3 [M+1].

Step 4: Synthesis of Compound WX-200 and WX-201

Compound 5-3 (0.5 g, 0.75 mmol, 1.00 eq) was purified by preparative SFC [column: AS-H (250 mm*30 mm, 5 μm), mobile phase (A: $CO_2$, B: methanol containing 0.1 ammonium hydroxide, gradient: B 25%-25%)] to give compound WX-200 (130 mg, yield 26.00%, retention time: first peak) and WX-201 (129 mg, yield 25.00%, retention time: second peak). MS (ESI) m/z: 593.2 [M+1].

Referring to the synthesis method of steps 1-4 in embodiment 5, the embodiments in the following table were synthesized.

| compound No. | Structure | MS + 1 | $^1$HNMR (analysis) |
|---|---|---|---|
| WX-160 | 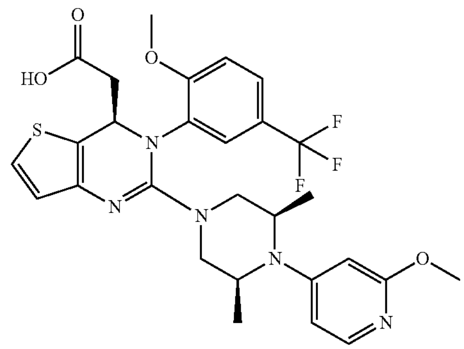 [SMILES: COc1cc(N2[C@H](C)CN(C3=Nc4ccsc4[C@@H](CC(=O)O)N3c3cc(C(F)(F)F)ccc3OC)C[C@@H]2C)ccn1] | 590.2 | $^1$HNMR (400 MHz, METHANOL-$d_4$) δ 7.74-7.72 (d, J = 6.40 Hz, 1 H), 7.54-7.52 (br d, J = 8.00 Hz, 1 H), 7.26-7.25 (br d, J = 5.60 Hz, 2 H), 6.97-6.96 (d, J = 5.20 Hz 1 H), 6.43-6.41 (dd, J = 6.40 Hz, 2.00 Hz, 1 H), 6.01 (s, 1 H), 5.05 (br s, 1 H), 4.06-3.88 (m, 3 H), 3.83-3.68 (m, 7 H), 3.42-2.91 (m, 2 H), 2.63-2.57 (m, 1 H), 1.07-1.05 (d, J = 6.00, 3 H), 0.46 (br s, 3 H). SFC method [column: AS-H (250 mm * 30 mm, 5 μm), mobile phase (A: $CO_2$, B: methanol containing 0.1 ammonium hydroxide, gradient: B 25%-25%)], retention time: first peak |
| WX-161 | 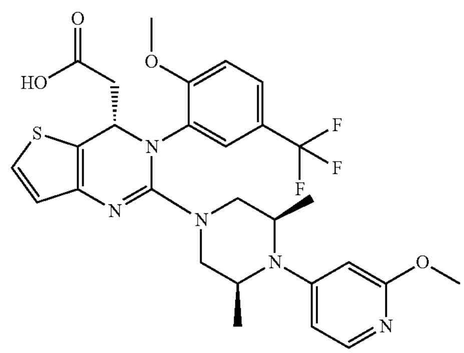 [SMILES: COc1cc(N2[C@H](C)CN(C3=Nc4ccsc4[C@H](CC(=O)O)N3c3cc(C(F)(F)F)ccc3OC)C[C@@H]2C)ccn1] | 590.2 | $^1$HNMR (400 MHz, METHANOL-$d_4$) δ 7.74-7.73 (d, J = 5.60 Hz, 1H), 7.56-7.54 (br d, J = 7.20 Hz, 1H), 7.28-7.26 (br d, J = 4.40 Hz, 2H), 6.98-6.97 (d, J = 4.80 Hz 1H), 6.45-6.44 (dd, J = 4.80 Hz, 2.00 Hz, 1H), 6.04 (s, 1 H), 5.10 (br s, 1H), 4.07-3.98 (m, 3H), 3.84-3.69 (m, 7H), 3.19-3.01 (m, 2H), 2.65-2.59 (m, 1H), 1.08-1.06 (d, J = 6.40, 3H), 0.48 (br s, 3H). SFC method [column: AS-H (250 mm * 30 mm, 5 μm), mobile phase (A: $CO_2$, B: methanol containing 0.1 ammonium hydroxide, gradient: B 25%-25%)], retention time: second peak |
| WX-169 | 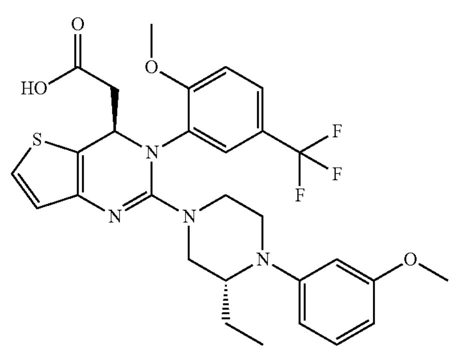 [SMILES: CC[C@@H]1CN(C2=Nc3ccsc3[C@@H](CC(=O)O)N2c2cc(C(F)(F)F)ccc2OC)CCN1c1cccc(OC)c1] | 589.2 | $^1$HNMR (400 MHz, CHLOROFORM-d) δ 7.49 (br d, J = 7.6 Hz, 1H), 7.15-6.99 (m, 4H), 6.87 (br s, 1H), 6.38-3.33 (m, 2H), 6.25 (br s, 1H), 5.01 (br s, 1H), 3.89-3.58 (m, 9H), 3.29 (br s, 2H), 3.11-3.01 (m, 3H), 2.81-2.79 (m, 1H), 1.32-1.21 (m, 2H), 0.82-0.79 (m, 3H). SFC method [column: AD-H (250 mm * 30 mm, 5 μm), mobile phase (A: $CO_2$, B: methanol containing 0.1 ammonium hydroxide, gradient: B 30%-30%)], retention time: first peak |

| compound No. | Structure | MS + 1 | ¹HNMR (analysis) |
|---|---|---|---|
| WX-170 | 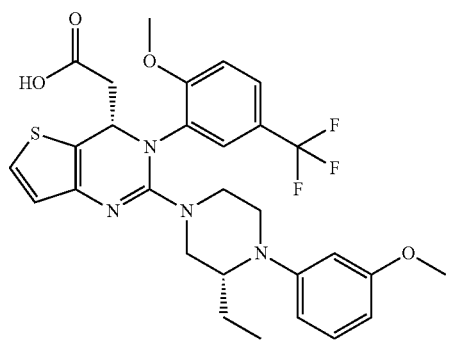 [SMILES: CC[C@@H]1CN(C2=Nc3ccsc3[C@H](CC(=O)O)N2c2cc(C(F)(F)F)ccc2OC)CCN1c1cccc(OC)c1] | 589.2 | ¹HNMR (400 MHz, CHLOROFORM-d) δ 7.42 (br d, J = 8.8 Hz, 1H), 7.13 (t, J = 8.4 Hz, 1H), 7.01 (br s, 3H), 6.88 (br s, 1H), 6.40 (br t, J = 9.2 Hz, 2H), 6.33 (br s, 1H), 5.02 (br s, 1H), 3.92 (br s, 3H), 3.77 (s, 5H), 3.53 (br s, 2H), 3.36-3.27 (m, 3H), 2.93-2.88 (m, 1H), 2.82-2.76 (m, 1H), 1.27-1.12 (m, 2H), 0.44 (br s, 3H). SFC method [column: AD-H (250 mm * 30 mm, 5 μm), mobile phase (A: $CO_2$, B: methanol containing 0.1 ammonium hydroxide, gradient: B 30%-30%)], retention time: second peak |
| WX-171 | 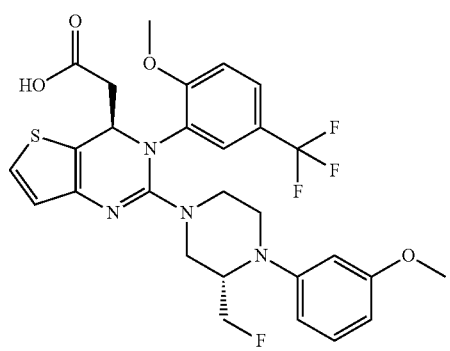 [SMILES: COc1cccc(N2CCN(C3=Nc4ccsc4[C@@H](CC(=O)O)N3c3cc(C(F)(F)F)ccc3OC)C[C@H]2CF)c1] | 593.2 | ¹HNMR (400 MHz, DMSO-$d_6$) δ 7.68-7.66 (d, J = 8 Hz, 1H), 7.38-7.12 (m, 3H), 7.02-7.01 (d, J = 4 Hz, 1H), 6.46-6.37 (m, 3H), 5.12 (m, 1H), 4.35-4.17 (m, 2H), 3.87-3.76 (m, 7H), 3.49 (s, 1H), 3.23 (m, 4H), 3.00 (s, 2H), 2.71-2.65 (m, 1H). SFC method [column: OD-H (250 mm * 30 mm, 5 μm), mobile phase (A: $CO_2$, B: methanol containing 0.1 ammonium hydroxide, gradient: B 30%-30%)], retention time: first peak |
| WX-172 | 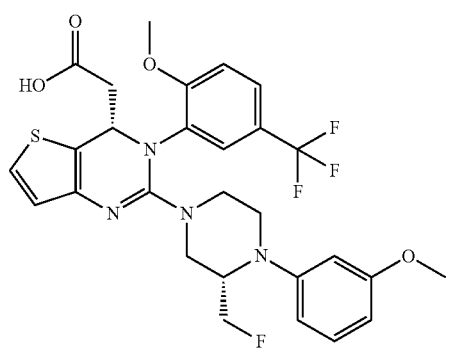 [SMILES: COc1cccc(N2CCN(C3=Nc4ccsc4[C@H](CC(=O)O)N3c3cc(C(F)(F)F)ccc3OC)C[C@H]2CF)c1] | 593.2 | ¹HNMR (400 MHz, DMSO-$d_6$) δ 7.56-7.54 (d, J = 8 Hz, 1H), 7.30-7.10 (m, 3H), 6.98 (s, 1H), 6.50-6.43 (m, 3H), 5.05 (m, 1H), 4.09-3.72 (m, 11H), 3.46 (s, 1H), 3.49 (s, 1H), 3.19 (s, 4H), 2.93 (m, 2H), 2.64 (m, 1H). SFC method [column: OD-H (250 mm * 30 mm, 5 μm), mobile phase (A: $CO_2$, B: methanol containing 0.1 ammonium hydroxide, gradient: B 40%-40%)], retention time: second peak |
| WX-196 | 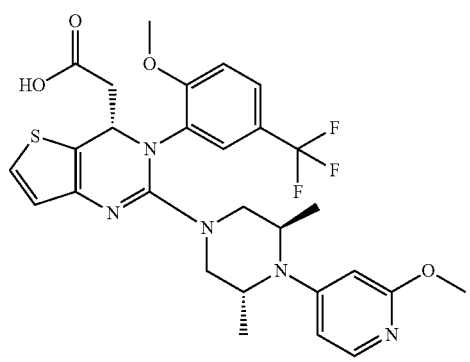 [SMILES: COc1cc(N2[C@H](C)CN(C3=Nc4ccsc4[C@H](CC(=O)O)N3c3cc(C(F)(F)F)ccc3OC)C[C@H]2C)ccn1] | 590.2 | ¹HNMR (400 MHz, DMSO-$d_6$) δ 7.80-7.78 (d, J = 8 Hz, 1H), 7.63-7.61 (d, J = 8 Hz, 1H), 7.34 (s, 2H), 7.02-7.01 (d, J = 4 Hz, 1H), 6.52-6.51 (d, J = 4 Hz, 1H), 6.09 (s, 1H), 5.27 (s, 1H), 4.03-3.93 (m, 7H), 2.93 (s, 1H), 2.70-2.65 (m, 1H), 1.03-1.01 (d, J = 8 Hz, 6H). SFC method [column: IC-H (250 mm * 30 mm, 5 μm), mobile phase (A: $CO_2$, B: methanol containing 0.1 ammonium hydroxide, gradient: B 42%-42%)], retention time: first peak |

| compound No. | Structure | MS + 1 | ¹HNMR (analysis) |
|---|---|---|---|
| WX-197 | 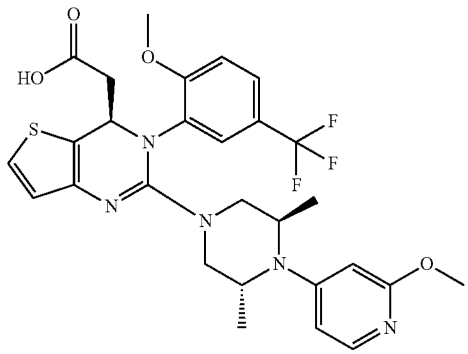 [SMILES: COc1cc(N2[C@H](C)CN(C3=Nc4ccsc4[C@@H](CC(=O)O)N3c3cc(C(F)(F)F)ccc3OC)C[C@H]2C)ccn1] | 590.2 | ¹HNMR (400 MHz, DMSO-$d_6$) δ 7.77-7.75 (d, J = 8 Hz, 1H), 7.62 (s, 1H), 7.39-7.29 (m, 2H), 7.03 (s, 1H), 6.41-6.40 (d, J = 4 Hz, 1H), 5.98-5.97 (d, J = 4 Hz, 1H), 5.21 (s, 1H), 3.89-3.75 (m, 8H), 2.92(m, 2H), 2.73-2.68 (m, 2H), 1.31(m, 6H). SFC method [column: IC-H (250 mm * 30 mm, 5 μm), mobile phase (A: $CO_2$, B: methanol containing 0.1 ammonium hydroxide, gradient: B 42%-42%)], retention time: second peak |
| WX-200 | 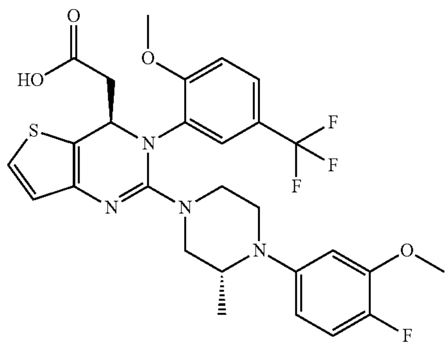 [SMILES: COc1cc(N2CCN(C3=Nc4ccsc4[C@@H](CC(=O)O)N3c3cc(C(F)(F)F)ccc3OC)C[C@H]2C)ccc1F] | 593.2 | ¹HNMR (400 MHz, METHANOL-$d_4$) δ 7.59-7.61 (d, J = 7.20 Hz, 1H), 7.26-7.25 (br d, J = 5.20 Hz, 2H), 6.96-6.90 (m, 2H), 6.62-6.61 (dd, J = 7.60 Hz, 2.80 Hz, 1H), 6.60-6.39 (m, 1H), 5.05 (br s, 1 H), 3.89-3.82 (m, 6H), 3.60 (br s, 1 H), 3.40 (br s, 3H), 2.94-2.91 (m, 2H), 2.79 (br s, 1H), 2.61-2.55 (dd, J = 14.40, 8.40 Hz, 1H), 0.82-0.80 (d, J = 6.40 Hz, 3H). SFC method [column: AD-H (250 mm * 30 mm, 5 μm), mobile phase (A: $CO_2$, B: methanol containing 0.1 ammonium hydroxide, gradient: B 30%-30%)], retention time: first peak |
| WX-201 | 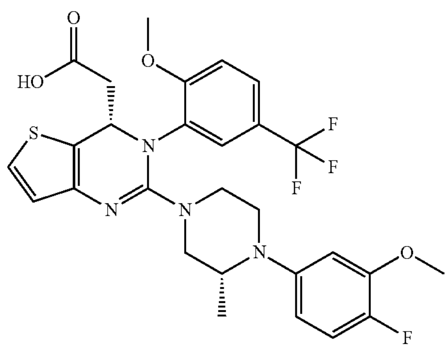 [SMILES: COc1cc(N2CCN(C3=Nc4ccsc4[C@H](CC(=O)O)N3c3cc(C(F)(F)F)ccc3OC)C[C@H]2C)ccc1F] | 593.2 | ¹HNMR (400 MHz, METHANOL-$d_4$) δ 7.51 (br d, J = 6.8 Hz, 1H), 7.23 (br d, J = 5.0 Hz, 1H), 7.14 (br d, J = 8.0 Hz, 1H), 6.91-6.80 (m, 2H), 6.55 (m, 1H)6.35 (m, 1H), 4.99 (br s, 1H), 3.88-3.68 (m, 7H), 3.48 (br d, J = 10.8 Hz, 2H), 3.32 (m, 2H), 3.14 (m, 1H), 2.79 (br s, 2H), 2.65 (br s, 2H), 2.49 (dd, J = 14.8, 7.6 Hz, 1H), 1.05 (d, J = 6.0 Hz, 1H), 0.46 (br s, 3H). SFC method [column: AD-H (250 mm * 30 mm, 5 μm), mobile phase (A: $CO_2$, B: methanol containing 0.1 ammonium hydroxide, gradient: B 30%-30%)], retention time: second peak |

Embodiment 6

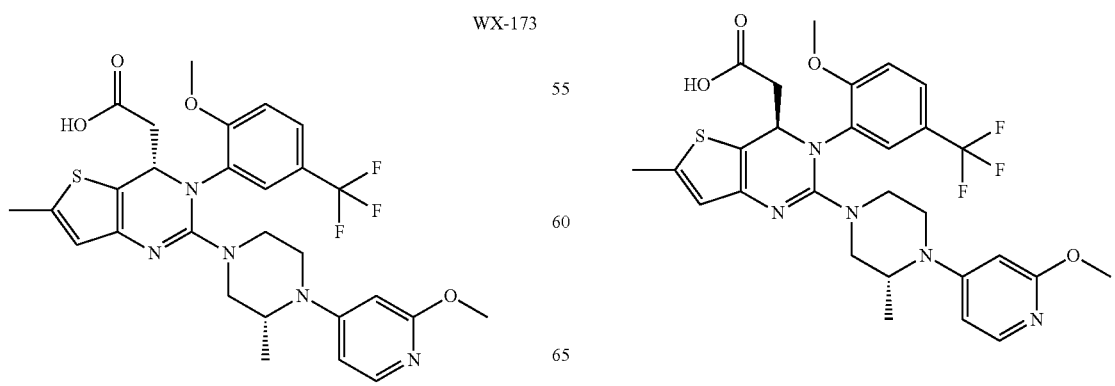

WX-173

WX-174

Synthetic Route:
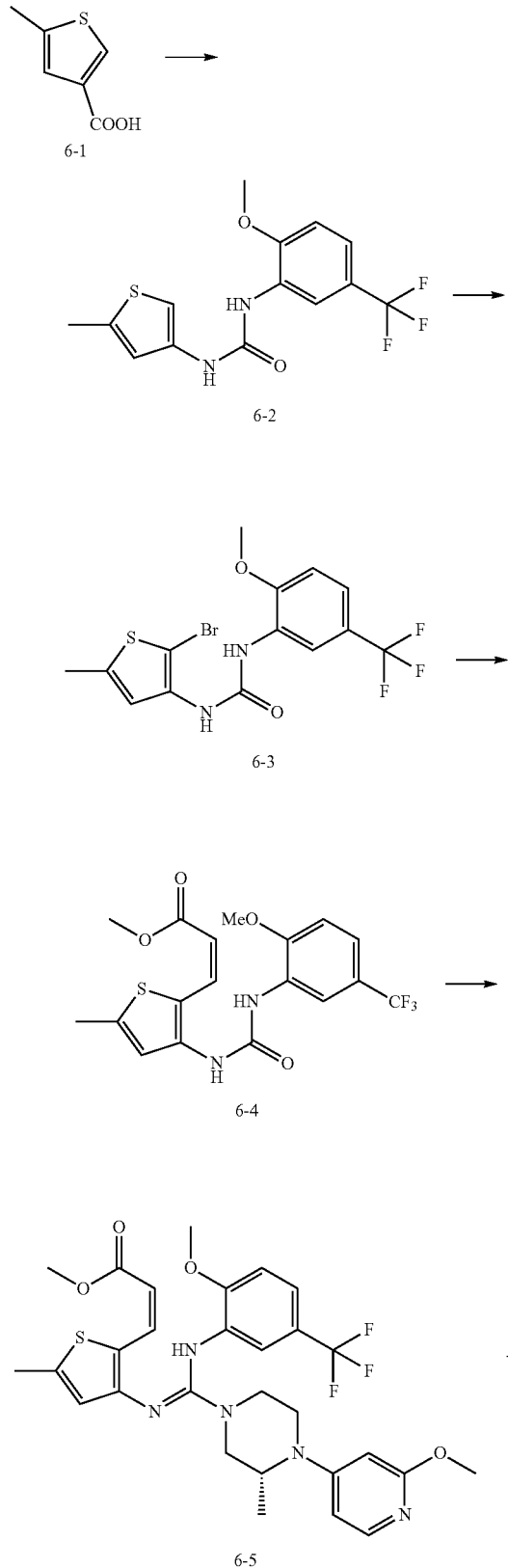
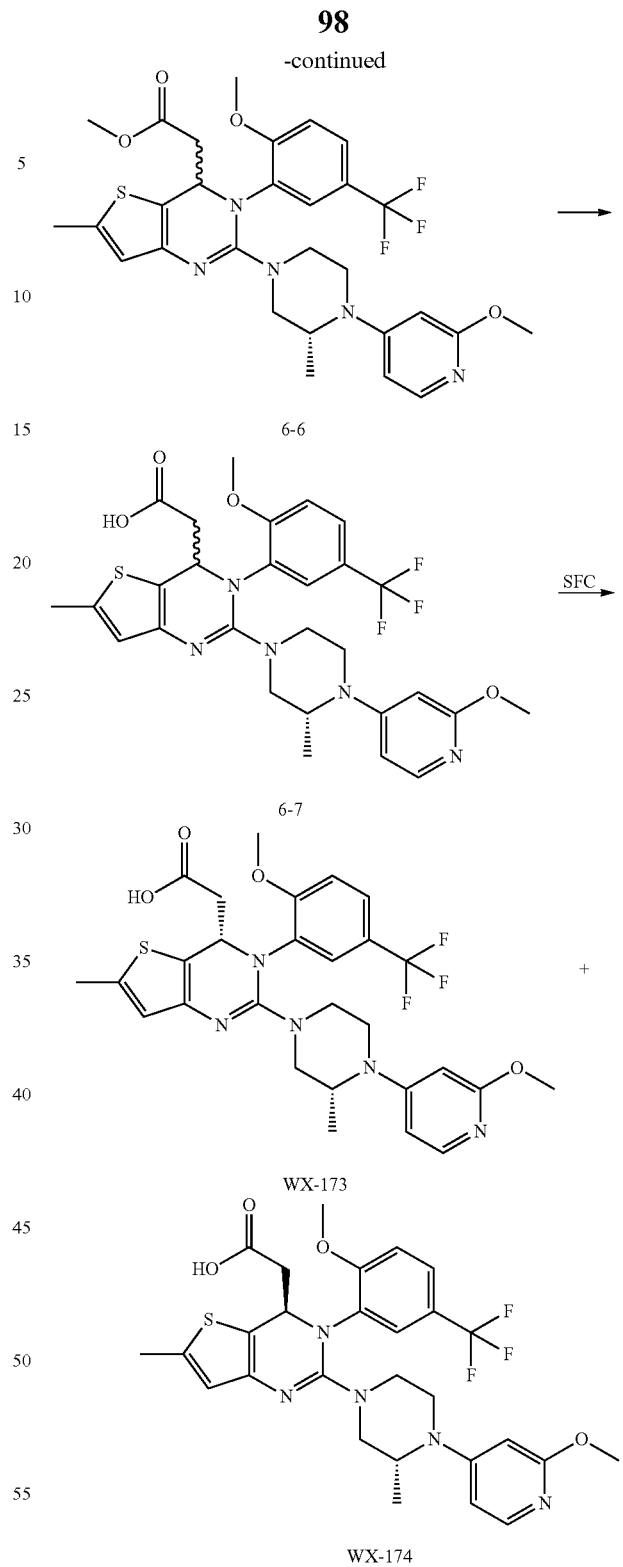
Step 1: Synthesis of Compound 6-2
To a solution of compound 6-1 (2 g, 14.07 mmol, 1 eq) and DPPA (3.87 g, 14.07 mmol, 3.05 mL, 1 eq) in toluene (20 mL) was added triethylamine (4.27 g, 42.20 mmol, 5.87 mL, 3 eq) at 15° C., the reaction solution was stirred under nitrogen atmosphere at 15° C. for 0.5 hour, then heated to 80° C. and stirred for 2 hours. Then 2-Methoxy-5-trifluoromethylaniline (2.55 g, 13.36 mmol, 0.95 eq) was added to the reaction solution, the reaction solution was stirred at 80° C. for 12 hours. Then the reaction solution was concentrated under reduced pressure. The residue was diluted with water (30 mL), extracted twice with ethyl acetate (20 mL). The organic phases were combined, washed with brine, dried over anhydrous sodium sulfate and concentrated under reduced pressure. The residue was purified by silica gel column (eluent: PE:EtOAc=1:0 to 10:1) to give compound 6-2 (4 g, 12.11 mmol, yield 86.08%). MS (ESI) m/z: 331.1 [M+1].

Step 2: Synthesis of Compound 6-3

To a solution of compound 6-2 (4 g, 12.11 mmol, 1 eq) in DCM (50 mL) was added NBS (2.26 g, 12.71 mmol, 1.05 eq) in batches under nitrogen atmosphere at 0-5° C., the mixture was stirred at 0° C. for 10 minutes. Then saturated aqueous sodium bicarbonate (30 mL) was added at 0-5° C. to quench the reaction. The mixture was extracted twice with DCM (20 mL), the combined organic phases were washed with brine (50 mL), dried over anhydrous sodium sulfate and concentrated under reduced pressure. The residue was purified by silica gel column (PE:EtOAc=1:0 to 20:1) to give compound 6-3 (2 g, 3.63 mmol, purity 74.23%, yield 29.96%). MS (ESI) m/z: 409.1 [M+1].

Step 3: Synthesis of Compound 6-4

To a solution of compound 6-3 (1.5 g, 3.67 mmol, 1 eq) and BB-11 (2.33 g, 11.00 mmol, 3 eq) in ethylene glycol dimethyl ether (20 mL) was added Pd(dppf)Cl$_2$ (268.21 mg, 366.55 μmol, 0.1 eq) and potassium phosphate (1.71 g, 8.06 mmol, 2.2 eq) at room temperature, the mixture was stirred under nitrogen atmosphere at 85° C. for 12 hours. Then the reaction solution was poured into 20 mL water and extracted with EtOAc (20 mL) twice. The combined organic phases were washed with brine (40 mL), dried over anhydrous sodium sulfate, filtered and concentrated to give a crude product, which was purified by silica gel column (PE:EtOAc=50:1 to 5:1) and neutral prep-HPLC to give compound 6-4 (170 mg, 410.23 μmol, yield 11.2%). MS (ESI) m/z: 415.1 [M+1].

Step 4: Synthesis of Compound 6-5

To a solution of compound 6-4 (170 mg, 410.23 μmol, 1 eq) and 2,6-lutidine (263.74 mg, 2.46 mmol, 286.67 μL, 6 eq) in toluene (5 mL) was added PCl$_5$ (256.28 mg, 1.23 mmol, 3 eq) in batches under nitrogen atmosphere at 15° C., the reaction solution was heated to 50° C. and stirred for 1.5 hours. Then the reaction solution was adjusted to neutral with 2M potassium hydroxide solution at 0° C. The mixture was partitioned and the organic phase was washed with 1 M citric acid solution (10 mL) and brine (10 mL) respectively. Then Compound BB-5 (129.91 mg, 533.00 μmol, 1.3 eq, HCl), disodium phosphate (349.22 mg, 2.46 mmol, 349.22 μL, 6 eq), triethylamine (124.46 mg, 1.23 mmol, 171.20 μL, 3 eq), toluene (2 mL) and water (1 mL) were respectively added to the solution at 15° C. The reaction solution was heated to 50° C. and stirred for 2 hours. Then the reaction solution was poured into water (20 mL) and the mixture was extracted twice with EtOAc (30 mL). The combined organic phases were washed with brine (50 mL), dried over anhydrous sodium sulfate, filtered and concentrated to give a crude product of compound 6-5 (200 mg, crude), which was directly used in the next step. MS (ESI) m/z: 604.3 [M+1].

Step 5: Synthesis of Compound 6-6

The crude compound 6-5 (200 mg, 331.32 μmol, 1 eq) obtained in step 4 was dissolved in toluene (20 mL) at 20° C., followed by addition of DBU (302.64 mg, 1.99 mmol, 299.64 μL, 6 eq). The mixture was stirred at 110° C. for 2 hours. Then the reaction solution was concentrated and purified by silica gel column (PE:EtOAc=10:1 to 0:1) to give mixed compound 5-2 (120 mg, 198.79 μmol, yield 48.5% for steps 4-5). MS (ESI) m/z: 604.3 [M+1].

Step 6: Synthesis of Compound 6-7

To a solution of compound 6-7 (120 mg, 198.79 μmol, 1 eq) in a mixed solvent of MeOH and water (MeOH:water=3:1, 10 mL) was added sodium hydroxide (79.52 mg, 1.99 mmol, 10 eq) at room temperature, the mixture was stirred at 70° C. for 2 hours. Then the reaction solution was concentrated to remove methanol, then water (20 mL) was added. After the impurities in the aqueous phase was extracted with EtOAc (20 mL), the aqueous phase was adjusted to pH of about 5 with 1 M hydrochloric acid. The mixture was extracted twice with EtOAc (30 mL). The combined organic phases were washed with brine (50 mL), dried over anhydrous sodium sulfate, filtered and concentrated to give a crude product, which was purified by prep-HPLC to give compound 6-7 (90 mg, 135.91 μmol, yield 68.4%, purity 90.4%). MS (ESI) m/z: 590.2 [M+1].

Step 7: Synthesis of Compound WX-173 and WX-174

Compound 6-7 (90 mg, 135.91 μmol, 1.00 eq) was purified by preparative SFC [column: IC-H (250 mm*30 mm, 5 μm), mobile phase (A: CO$_2$, B: methanol containing 0.1 ammonium hydroxide, gradient: B 40%-40%)] to give compound WX-173 (32.1 mg, purity 92.31%, yield 37%, retention time: first peak) and WX-174 (40.1 mg, purity 95.02%, yield 47.5%, retention time: second peak). MS (ESI) m/z: 590.2 [M+1].

Referring to the synthesis method of steps 1-8 in embodiment 6, compound WX-153 in the following table were synthesized.

| compound No. | Structure | MS + 1 | $^1$HNMR (analysis) |
|---|---|---|---|
| WX-153 | 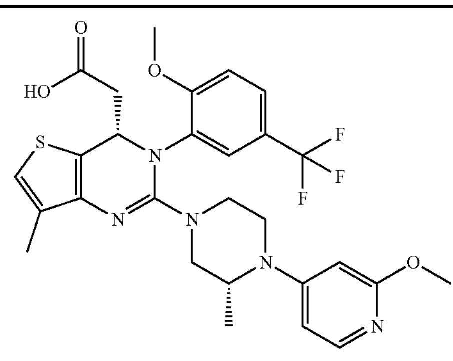 | 590.2 | $^1$HNMR (400 MHz, METHANOL-d$_4$) δ 7.77-7.70 (m, 1H), 7.50 (dd, J = 1.63, 8.66 Hz, 1H), 7.20 (br s, 1H), 6.86 (s, 1H), 6.47 (dd, J = 2.26, 6.53 Hz, 1H), 6.07 (d, J = 2.26 Hz, 1H), 4.94 (br s, 1H), 4.12-3.74 (m, 8H), 3.66 (br d, J = 9.79 Hz, 2H), 3.19 (br d, J = 11.54 Hz, 1H), 3.05-2.86 (m, 3H), 2.58 (dd, J = 8.03, 14.81 Hz, 1H), 2.28 (d, J = 0.75 Hz, 3H), 0.41 (br s, 3H). SFC method [column: AD (250 mm * 30 mm, 5 μm), mobile phase (A: CO$_2$, B: isopropanol containing 0.1 ammonium hydroxide, gradient: B 25%-25%)], retention time: first peak |

-continued

| compound No. | Structure | MS + 1 | ¹HNMR (analysis) |
|---|---|---|---|
| WX-173 | 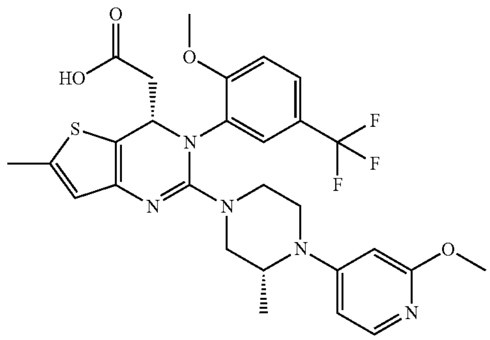 | 590.2 | ¹HNMR (400 MHz, METHANOL-$d_4$) δ 7.73 (d, J = 6.4 Hz, 1H), 7.53 (d, J = 7.6 Hz, 1H), 7.19 (br s, 1H), 6.67 (s, 1H), 6.46 (dd, J = 6.4, 2.4 Hz, 1H), 6.06 (d, J = 2.0 Hz, 1H), 4.89 (br s, 1 H), 4.08 (br s, 1H), 3.82 (s, 7H), 3.61 (t, J = 26.0 Hz, J = 11.2 Hz 2H), 3.27 (br s, 1H), 2.72-3.15 (m, 3H), 2.58 (dd, J = 14.0, 6.8 Hz, 1H), 0.50 (br s, 3H). SFC method [column: IC-H (250 mm * 30 mm, 5 μm), mobile phase (A: $CO_2$, B: methanol containing 0.1 ammonium hydroxide, gradient: B 40%-40%)], retention time: first peak |
| WX-174 | 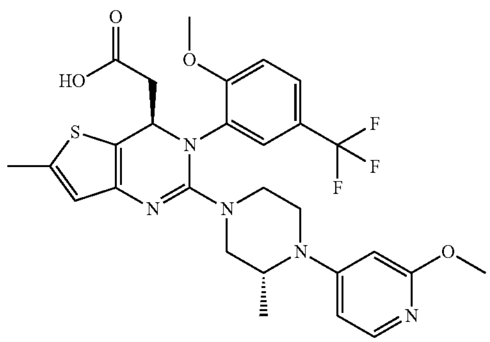 | 590.2 | ¹HNMR (400 MHz, METHANOL-$d_4$) δ 7.72 (d, J = 6.0 Hz, 1 H), 7.53 (d, J = 8.4 Hz, 1 H), 7.19 (br s, 1 H), 6.61 (s, 1 H), 6.39 (dd, J = 6.0, 2.4 Hz, 1 H), 5.91 (s, 1 H), 4.89 (br s, 1 H), 4.03-3.77 (m, 8 H), 3.62 (br s, 1 H), 3.46 (br d, 1 H), 3.16 (br s, 2 H), 2.88 (br s, 2 H), 2.52 (dd, J = 14.00, 8.40 Hz, 1 H), 2.41 (s, 3 H), 1.01 (br d, J = 6.0 Hz, 3 H). SFC method [column: IC-H (250 mm * 30 mm, 5 μm), mobile phase (A: $CO_2$, B: methanol containing 0.1 ammonium hydroxide, gradient: B 40%-40%)], retention time: second peak |

Test Embodiment 1

Fluorescence Decay Assay Against Human Cytomegalovirus

The antiviral activity of the compound against human cytomegalovirus (HCMV) was evaluated by determining the half maximal effective concentration ($EC_{50}$) of the compound. The HCMV used in this assay was inserted with enhanced green fluorescent protein (EGFP) by gene recombination, so the viral replication in cells could be reflected by the expression level of GFP. The inhibitory activity of the compound on HCMV GFP expression was evaluated by determining the fluorescence intensity in the wells of different concentrations of the compound using a high content cell analysis platform Acumen eX3.

Fluorescence Decay Assay Against HCMV

MRC5 cells were inoculated into a black 96-well cell culture plate at a density of 20,000 cells per well. The plate was incubated overnight in a 37° C., 5% $CO_2$ incubator. US3-6-EGFP-HCMV-AD169 viruses were added to the cell culture well at a certain MOI (0.003-0.1) and the plate was incubated for 3 hours in a 37° C., 5% $CO_2$ incubator. After adsorption of viruses, the medium containing viruses was aspirated and 200 μL of cell culture medium containing different concentrations of the compound (4-fold dilution, 6 test concentrations) was added. The final concentration of DMSO in the medium was 1%. Virus control wells (with DMSO added, but no compound was added) and inhibition control wells (with a high concentration of control compound added) were set. The cell plate was incubated for 10 days in a 37° C., 5% $CO_2$ incubator and the liquid was renewed on the 4$^{th}$ day and 7$^{th}$ day. After 10 days of culture, the fluorescence intensity was determined using a high content cell analysis platform Acumen eX3 (TTP LabTech). The original data was used for calculating the antiviral activity of the compound.

$$\text{inhibition \%} = 100 - \frac{\text{signal of compound well} - \text{mean signal of inhibition control well}}{\text{signal of virus control well} - \text{mean signal of inhibition control well}} \times 100\%$$

The inhibition % was imported into GraphPad Prism software for data processing to give a corresponding dose-response curve for the compound and the $EC_{50}$ of the test compound was obtained.

The results were shown in table 1:

TABLE 1

| Compound | $EC_{50}$ (μM) |
|---|---|
| WX-075 | 0.295 |
| WX-076 | 0.001 |
| WX-087 | >1 |
| WX-088 | 0.002 |
| WX-089 | >1 |
| WX-090 | 0.079 |
| WX-097 | 0.001 |
| WX-098 | 0.031 |
| WX-099 | 0.024 |
| WX-100 | 0.073 |
| WX-106 | >1 |
| WX-107 | 0.004 |
| WX-108 | 0.340 |
| WX-109 | 0.004 |
| WX-112 | 0.001 |
| WX-113 | 0.107 |

TABLE 1-continued

| Compound | EC$_{50}$ (μM) |
|---|---|
| WX-127 | 0.830 |
| WX-128 | 0.015 |
| WX-129 | 0.014 |
| WX-130 | >0.1 |
| WX-131 | 0.055 |
| WX-132 | 0.00015 |
| WX-133 | 0.017 |
| WX-134 | >1 |
| WX-135 | 0.941 |
| WX-136 | 0.00017 |
| WX-137 | 0.031 |
| WX-138 | >1 |
| WX-139 | 0.003 |
| WX-140 | 0.144 |
| WX-141 | 0.0002 |
| WX-142 | 0.056 |
| WX-143 | 0.00089 |
| WX-144 | 0.261 |
| WX-145 | 0.002 |
| WX-146 | 0.352 |
| WX-147 | 0.00017 |
| WX-148 | 0.012 |
| WX-149 | 0.00067 |
| WX-150 | 0.020 |
| WX-151 | 0.000503 |
| WX-153 | 0.00026 |
| WX-160 | 0.0444 |
| WX-161 | 0.000317 |
| WX-169 | >0.538 |
| WX-170 | 0.000264 |
| WX-171 | >0.01 |
| WX-172 | 0.000099 |
| WX-173 | 0.000849 |
| WX-174 | >0.01 |
| WX-196 | 0.001914 |
| WX-197 | >0.01 |
| WX-198 | 0.000713 |
| WX-199 | >0.01 |
| WX-200 | >0.01 |
| WX-201 | 0.00053 |
| WX-203 | >0.01 |
| WX-204 | 0.000172 |

Conclusion: the compounds of the present invention exhibit a good inhibitory activity against human cytomegalovirus replication in vitro.

Test Embodiment 2

Plasma Protein Binding Rate Test of the Compound

The protein binding rate of the test compound in CD-1 mice, SD rats, and human plasma was evaluated by equilibrium dialysis. The test compound was diluted into the plasma of the above three species respectively to prepare a sample with a final concentration of 2 μM. The sample was added to a 96-well equilibrium dialysis device, and dialyzed using a phosphate buffer solution at 37° C. for 4 hours. Warfarin was used as a control compound in the experiment. The concentration of the test compound and warfarin in the plasma and the buffer was determined by LC-MS/MS.

The results were shown in table 2. The compounds of the present invention have a reasonable plasma protein binding rate in the plasma of the three species, indicating that the ratio of the free drug concentration of the test compound is moderate in the plasma of the above three species and the compounds have a good druggability.

TABLE 2

| Compound No. | plasma protein binding PPB bound (%) |
|---|---|
| WX-088 | 97.6(H), 97.2(R), 97.8(M) |
| WX-109 | 90.3(H), 89.2(R), 94.5(M) |
| WX-132 | 97.8(H), 98.3(R), 98.9(M) |
| WX-139 | 94.0(H), 95.9(R), 98.6(M) |
| WX-141 | 94.0(H), 93.9(R), 98.3(M) |
| WX-143 | 93.1(H), 93.4(R), 98.5(M) |
| WX-145 | 97.7(H), 98.6(R), 99.9(M) |
| WX-147 | 98.2(H), 98.6(R), 99.8(M) |
| WX-149 | 97.6(H), 98.3(R), 99.8(M) |
| WX-151 | 95.3(H), 95.0(R), 98.9(M) |
| WX-153 | 98.1(H), 98.0(R), 98.9(M) |
| WX-161 | 98.0(H), 97.7(R), 99.6(M) |
| Compound A | 98.7(H), 98.5(R), 98.6(M) |

Note:
H refers to human,
R refers to rat, and
M refers to mouse.

Test Embodiment 3

Human Cytomegalovirus (HCMV) Transplantation Model in Mouse

A gelatin sponge containing HCMV was transplanted into mice. After 9 days of continuous administration, the gelatin sponge was collected for plaque detection. The anti-HCMV effect of the compound in the model was evaluated by determining the amount of HCMV in the gelatin sponge.

The animals selected for the experiment were NOD SCID mice (purchased from Shanghai Slac Laboratory Animal Co., Ltd.), 5 weeks, male, 5 animals per group. The day when the mice were transplanted with gelatin sponge was set to be day 0. Human foreskin fibroblasts (HFF, MOI=0.03) were previously infected with HCMV viruses (strain: GFP-AD169). The HMV cells infected with HCMV were added to a 1 cm$^2$ gelatin sponge for incubation. Animals were anesthetized by intraperitoneal injection of pentobarbital sodium at a dose of 75 mg/kg (10 mL/kg). After the animals entered deep anesthesia, the prepared gelatin sponge was subcutaneously transplanted into the back of the mice. From 1$^{st}$ day to 9$^{th}$ day, the mice were orally administered with the test compound at a dose of 8 mg/kg (10 mL/kg) once a day. At 4 hours after the administration on the 9th day, the gelatin sponge was taken out and digested. The plaque was detected. The test data showed that compound WX-136, WX-141 and WX-151 exhibited a decrease in HCMV viral load of 2.33 log PFU/mL, 2.38 log PFU/mL and 2.30 log PFU/mL, respectively, indicating that these compounds had an excellent efficacy in vivo. During the pharmacodynamic study in vivo, the mice were stable in weight and had no abnormal clinical observations, indicating that this class of compounds had no significant side effects on mice at the dose.

What is claimed is:

1. A compound represented by formula (II), a pharmaceutically acceptable salt or a tautomer thereof,

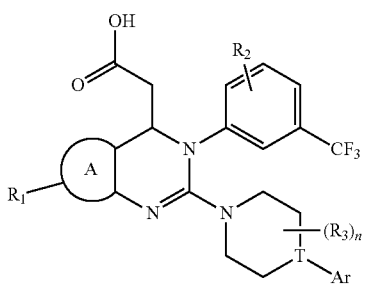

(II)

wherein,
ring A is a 5-membered heteroaromatic ring;
$R_1$ is H or halogen, or selected from the group consisting of $C_{1-6}$ alkyl and $C_{1-6}$ heteroalkyl, each of which is optionally substituted by 1, 2 or 3 R;
$R_2$ is H, or $C_{1-6}$ alkoxy which is optionally substituted by 1, 2 or 3 R;
$R_3$ is H, or selected from the group consisting of $C_{1-6}$ alkyl and $C_{1-6}$ heteroalkyl, each of which is optionally substituted by 1, 2 or 3 R;
T is N or C(R);
n is 1 or 2;
Ar is selected from the group consisting of phenyl and 6-membered heteroaryl, each of which is optionally substituted by 1, 2 or 3 R;
R is H, F, Cl, Br, I, OH, CN, $NH_2$ or C(=O)$NH_2$, or selected from the group consisting of $C_{1-6}$ alkyl and $C_{1-6}$ heteroalkyl, each of which is optionally substituted by 1, 2 or 3 R';
R' is F, Cl, Br, I, OH, CN, $NH_2$, COOH, Me, Et, $CF_3$, $CHF_2$, $CH_2F$, $NHCH_3$ or $N(CH_3)_2$;
the heteroatom or heteroatom group in the 5-membered heteroaromatic ring, 6-membered heteroaryl or $C_{1-6}$ heteroalkyl is selected from the group consisting of —C(=O)NH—, —NH—, —S(=O)$_2$NH—, —S(=O)NH—, —O—, —S—, N, —C(=O)O—, —C(=O)—, —S(=O)— and —S(=O)$_2$—;
in any of the above cases, the number of the heteroatom or the heteroatom group is independently 1, 2 or 3.

2. The compound the pharmaceutically acceptable salt or the tautomer thereof as defined in claim 1,
wherein n is 1.

3. The compound, the pharmaceutically acceptable salt or the tautomer thereof as defined in claim 2, wherein R is H, F, Cl, Br, I, OH, CN, $NH_2$ or C(=O)$NH_2$, or selected from the group consisting of $C_{1-3}$ alkyl, ($C_{1-3}$ alkyl)-O—, ($C_{1-3}$ alkyl)-S—, ($C_{1-3}$ alkyl)-NH— and N,N'-di($C_{1-3}$ alkyl)amino, each of which is optionally substituted by 1, 2 or 3 R';
or, R is H, F, Cl, Br, I, OH, CN, $NH_2$, C(=O)$NH_2$, Me, Et,

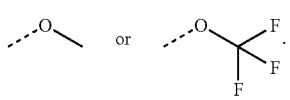

4. The compound, the pharmaceutically acceptable salt or the tautomer thereof as defined in claim 2, wherein, ring A is thienyl, furyl, oxazolyl, isothiazolyl or isoxazolyl;

or, the moiety

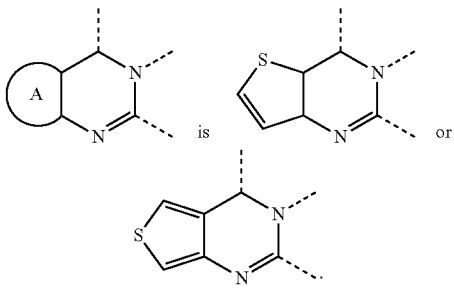

5. The compound, the pharmaceutically acceptable salt or the tautomer thereof as defined in claim 2, wherein, $R_1$ is H, F, Cl, Br or I, or selected from the group consisting of $C_{1-3}$ alkyl, ($C_{1-3}$ alkyl)-O— and ($C_{1-3}$ alkyl)-S—, each of which is optionally substituted by 1, 2 or 3 R;
or, $R_1$ is H, F, Cl, Br or I, or selected from the group consisting of Me and Et, each of which is optionally substituted by 1, 2 or 3 R;
or, $R_1$ is H, F, Cl, Br, I, Me or Et.

6. The compound, the pharmaceutically acceptable salt or the tautomer thereof as defined in claim 2, wherein, $R_2$ is H or ($C_{1-3}$ alkyl)-O— which is optionally substituted by 1, 2 or 3 R;
or, $R_2$ is H or

which is optionally substituted by 1, 2 or 3 R;
or, $R_2$ is H,

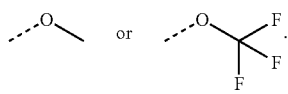

7. The compound, the pharmaceutically acceptable salt or the tautomer thereof as defined in claim 2, wherein, $R_3$ is H, or selected from the group consisting of $C_{1-3}$ alkyl, ($C_{1-3}$ alkyl)-O— and ($C_{1-3}$ alkyl)-S—, each of which is optionally substituted by 1, 2 or 3 R;
or, $R_3$ is H, or selected from the group consisting of Me, Et and

each of which is optionally substituted by 1, 2 or 3 R;
or, $R_3$ is H, Me, Et, $CF_3$,

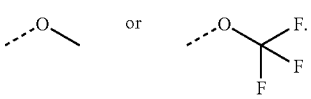

8. The compound, the pharmaceutically acceptable salt or the tautomer thereof as defined in claim 2, wherein, T is N, CH, C(F), C(Cl), C(Br) or C(I).

9. The compound, the pharmaceutically acceptable salt or the tautomer thereof as defined in claim 2, wherein, Ar is selected from the group consisting of phenyl, pyridyl, pyrimidinyl, pyrazinyl and pyridazinyl, each of which is optionally substituted by 1, 2 or 3 R;

or, Ar is selected from the group consisting of

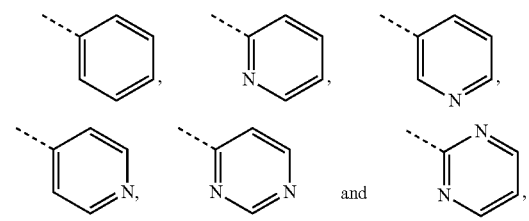

each of which is optionally substituted by 1, 2 or 3 R;

or, Ar is

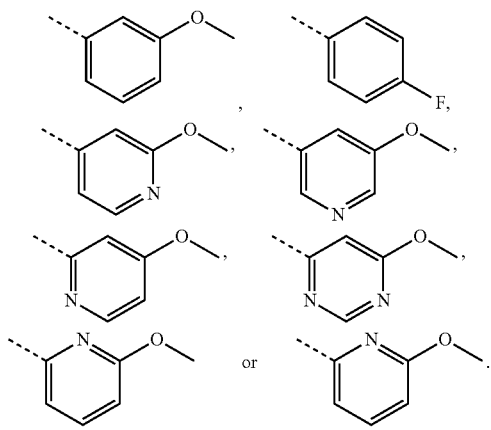

10. The compound, the pharmaceutically acceptable salt or the tautomer thereof as defined in claim 4, wherein, the moiety

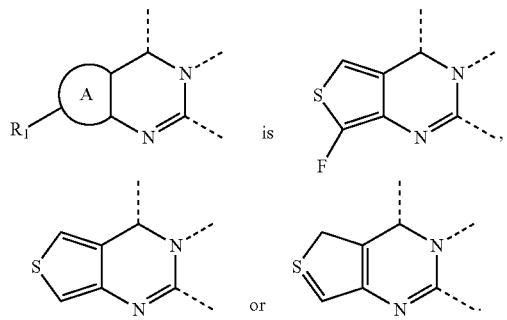

11. The compound, the pharmaceutically acceptable salt or the tautomer thereof as defined in claim 1, wherein, R is H, F, Cl, Br, I, OH, CN, NH$_2$ or C(=O)NH$_2$, or selected from the group consisting of C$_{1-3}$ alkyl, (C$_{1-3}$ alkyl)-O—, (C$_{1-3}$ alkyl)-S—, (C$_{1-3}$ alkyl)-NH— and N,N'-di(C$_{1-3}$ alkyl) amino, each of which is optionally substituted by 1, 2 or 3 R';

or, R is H, F, Cl, Br, I, OH, CN, NH$_2$, C(=O)NH$_2$, Me, Et,

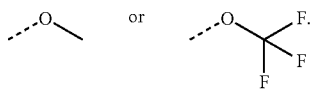

12. The compound, the pharmaceutically acceptable salt or the tautomer thereof as defined in claim 1, wherein, ring A is thienyl, furyl, oxazolyl, isothiazolyl or isoxazolyl;

or, the moiety

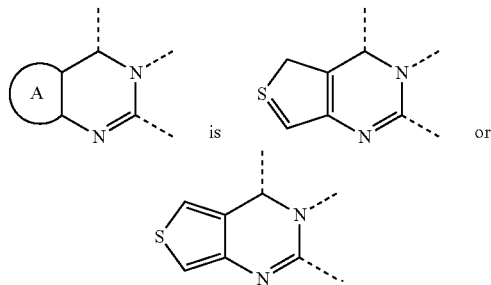

13. The compound, the pharmaceutically acceptable salt or the tautomer thereof as defined in claim 1, wherein, R$_1$ is H, F, Cl, Br or I, or selected from the group consisting of C$_{1-3}$ alkyl, (C$_{1-3}$ alkyl)-O— and (C$_{1-3}$ alkyl)-S—, each of which is optionally substituted by 1, 2 or 3 R;

or, R$_1$ is H, F, Cl, Br or I, or selected from the group consisting of Me and Et, each of which is optionally substituted by 1, 2 or 3 R;

or, R$_1$ is H, F, Cl, Br, I, Me or Et.

14. The compound, the pharmaceutically acceptable salt or the tautomer thereof as defined in claim 1, wherein, R$_2$ is H or (C$_{1-3}$ alkyl)-O— which is optionally substituted by 1, 2 or 3 R;

or, R$_2$ is H or

which is optionally substituted by 1, 2 or 3 R;

or, R$_2$ is H,

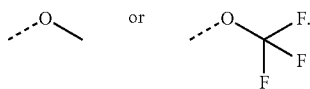

15. The compound, the pharmaceutically acceptable salt or the tautomer thereof as defined in claim 1, wherein, R$_3$ is H or selected from the group consisting of C$_{1-3}$ alkyl, (C$_{1-3}$ alkyl)-O— and (C$_{1-3}$ alkyl)-S—, each of which is optionally substituted by 1, 2 or 3 R;

or, R$_3$ is H, or selected from the group consisting of Me, Et and

each of which is optionally substituted by 1, 2 or 3 R;

or, R₃ is H, Me, Et, CF₃,

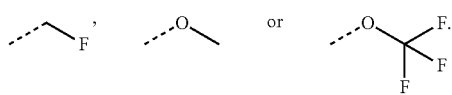

16. The compound, the pharmaceutically acceptable salt or the tautomer thereof as defined in claim 1, wherein, T is N, CH, C(F), C(Cl), C(Br) or C(I).

17. The compound, the pharmaceutically acceptable salt or the tautomer thereof as defined in claim 1, wherein, Ar is selected from the group consisting of phenyl, pyridyl, pyrimidinyl, pyrazinyl and pyridazinyl, each of which is optionally substituted by 1, 2 or 3 R;

or, Ar is selected from the group consisting of

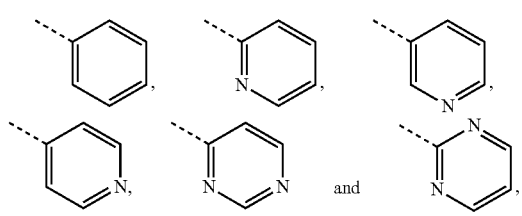

each of which is optionally substituted by 1, 2 or 3 R;

or, Ar is selected from the group consisting of

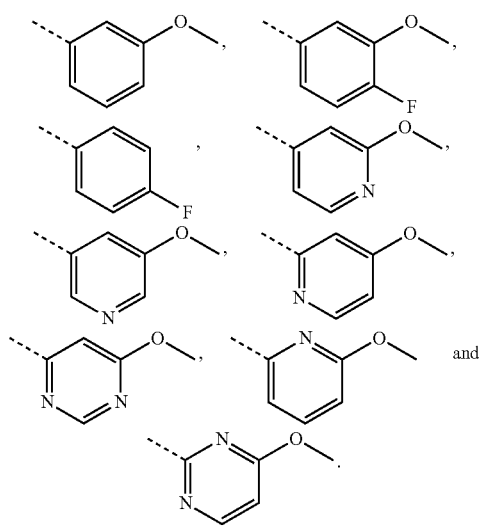

18. The compound, the pharmaceutically acceptable salt or the tautomer thereof as defined in claim 12, wherein, the moiety

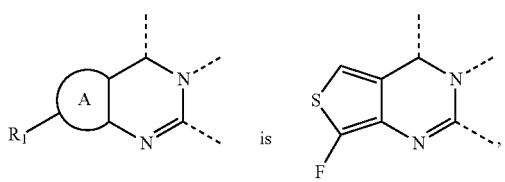

is

-continued

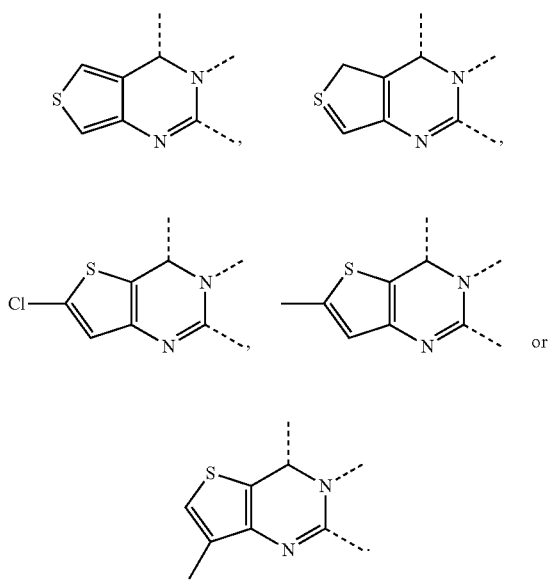

19. The compound, the pharmaceutically acceptable salt or the tautomer thereof as defined in claim 1, wherein, the moiety

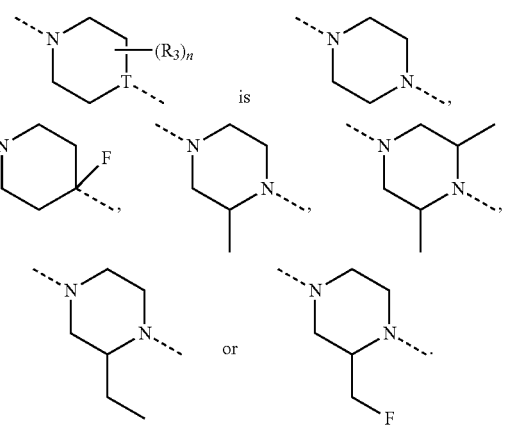

20. The compound, the pharmaceutically acceptable salt or the tautomer thereof as defined in claim 1, which is selected from the group consisting of (I-1)

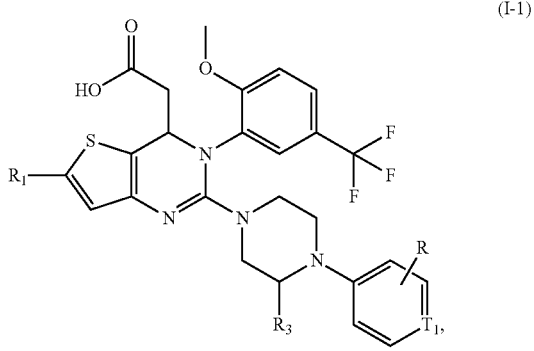

(I-2)
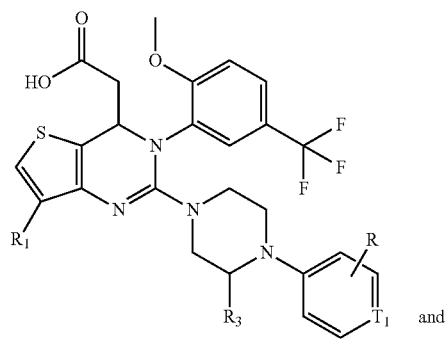
and
(I-3)
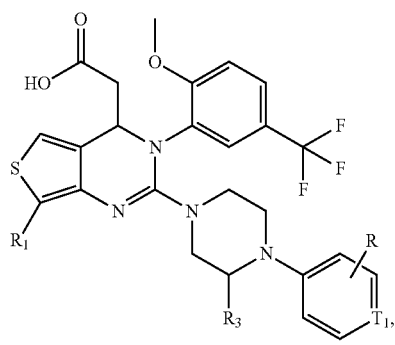
wherein,
R$_1$, R$_3$ and R are as defined in claim 1;
T$_1$ is N or CH;
or, is selected from the group consisting of
(I-1A)
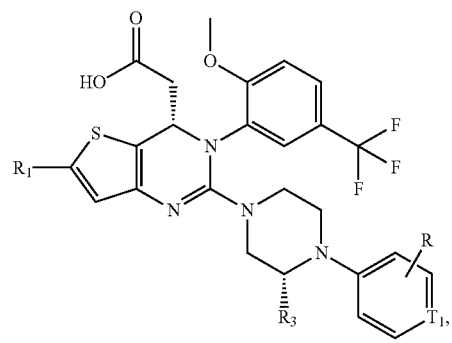
(I-1B)
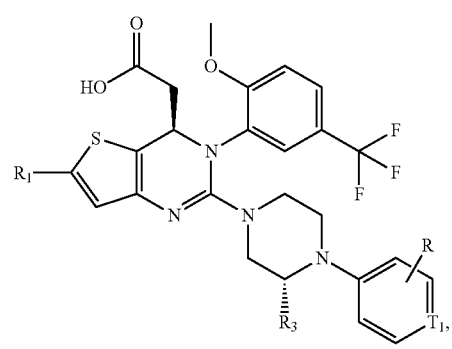
(I-1C)
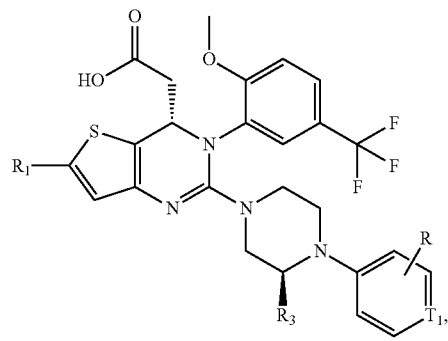
(I-1D)
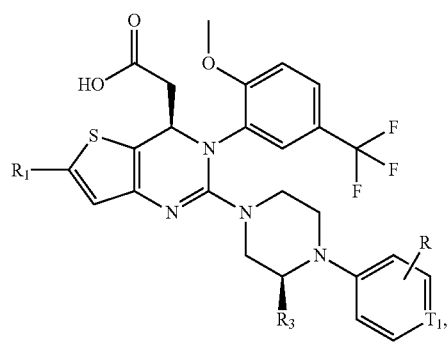
(I-2A)
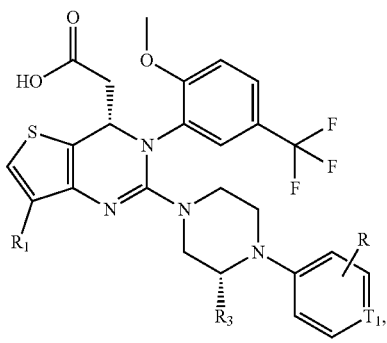
(I-2B)
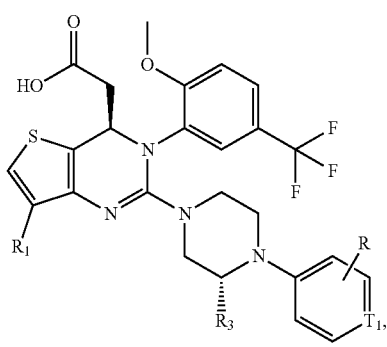

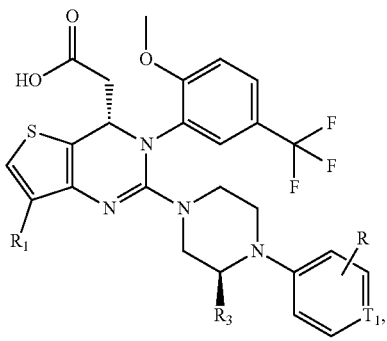
(I-2C)
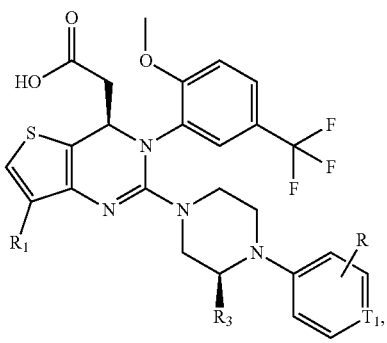
(I-2D)
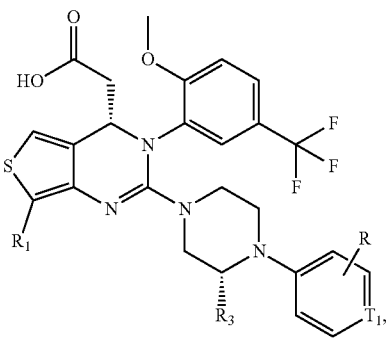
(I-3A)
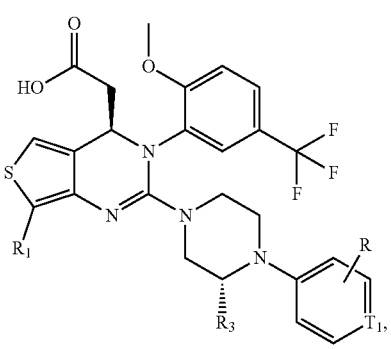
(I-3B)
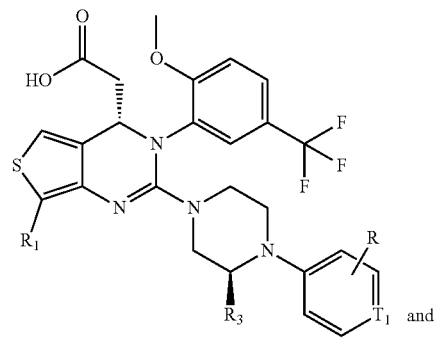
(I-3C)
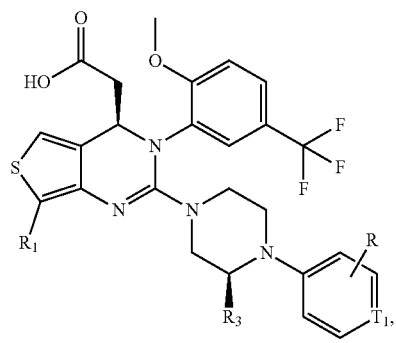
(I-3D)
wherein,
R₁, R₃ and R are as defined in claim 1;
T₁ is N or CH.
21. A compound, a pharmaceutically acceptable salt or a tautomer thereof, which is selected from the group consisting of
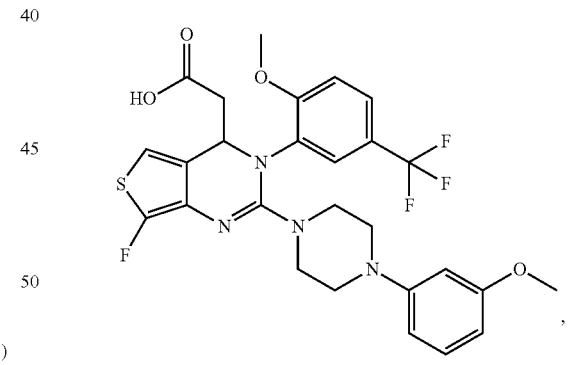
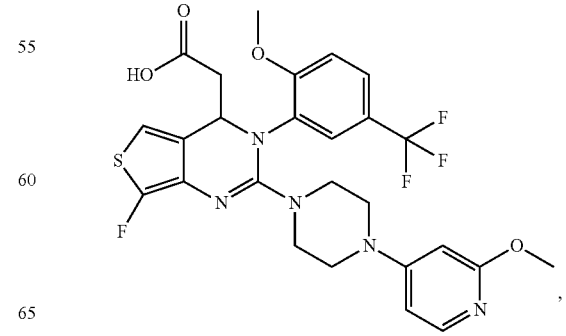

115
-continued
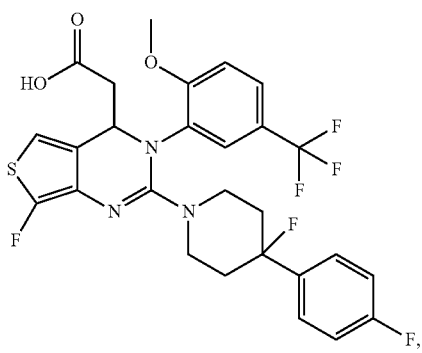
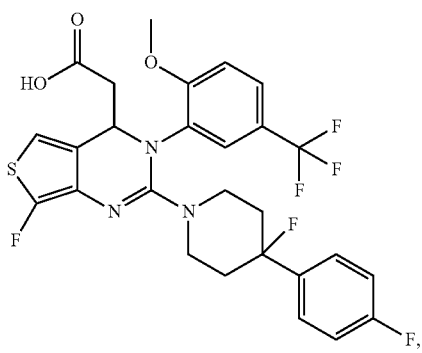
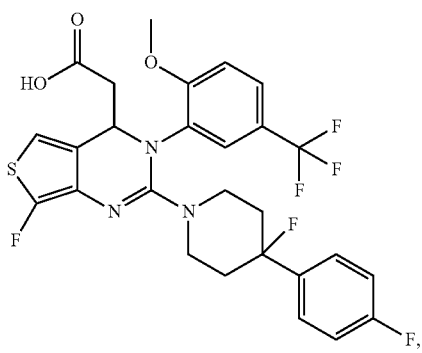
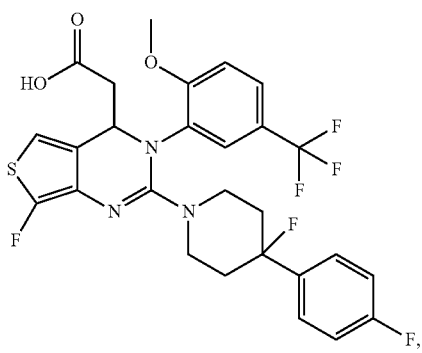
116
-continued
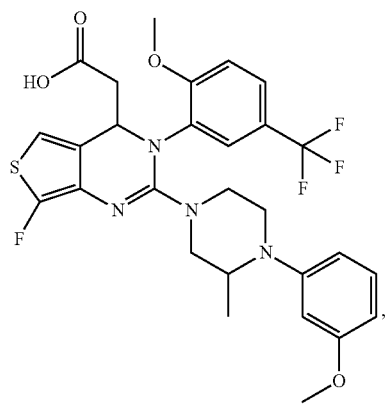
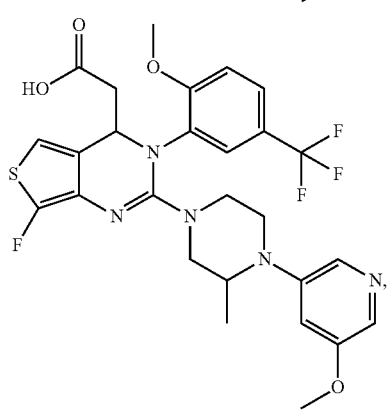
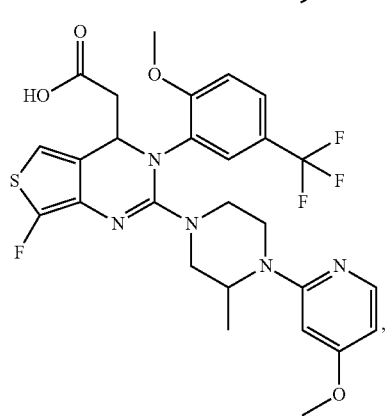
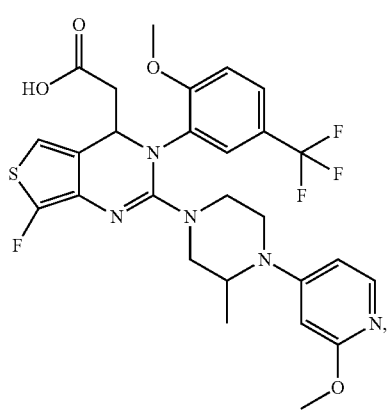

117
-continued
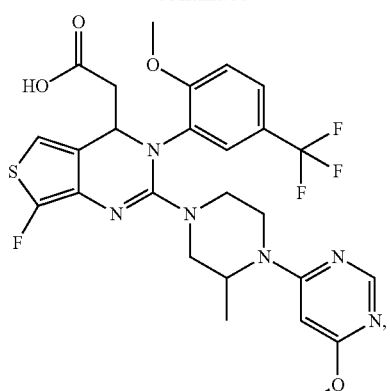
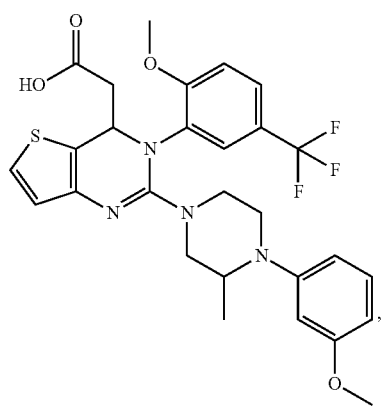
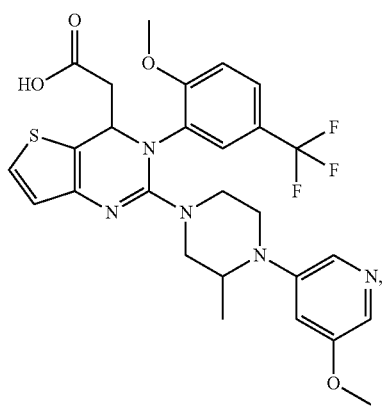
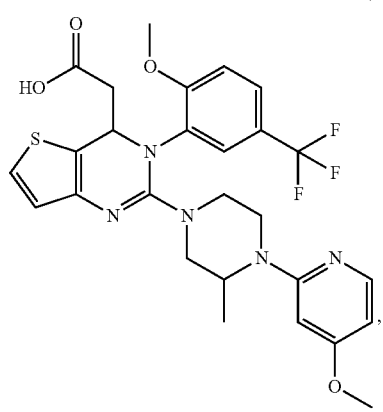
118
-continued
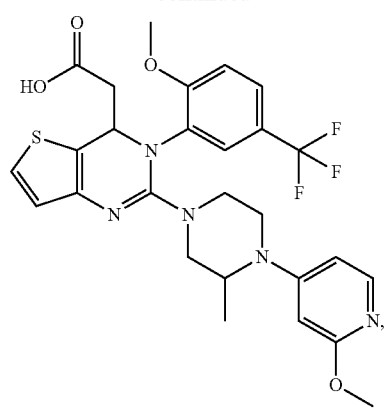
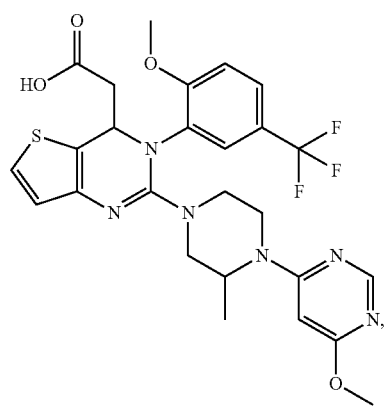
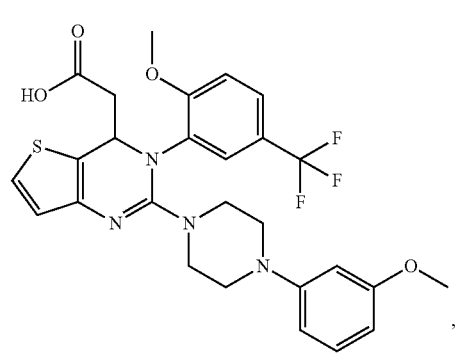
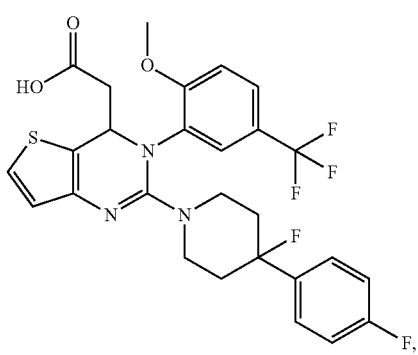

119
-continued
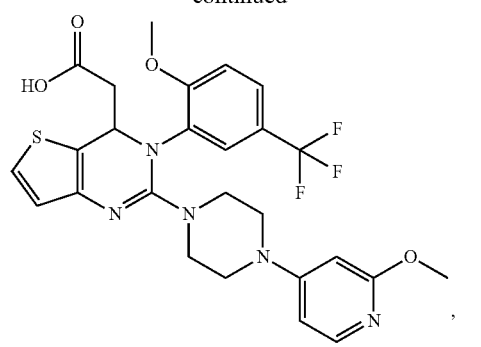
,
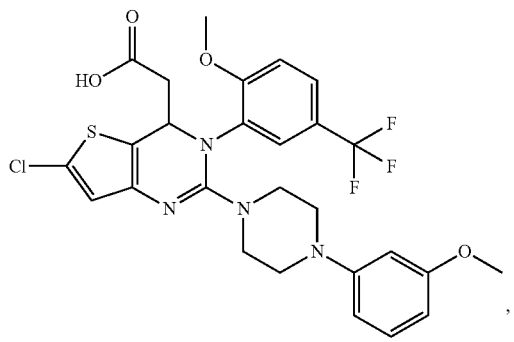
,
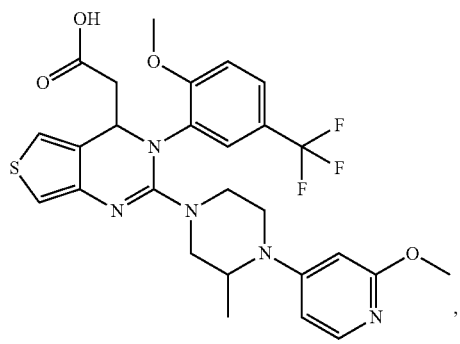
,
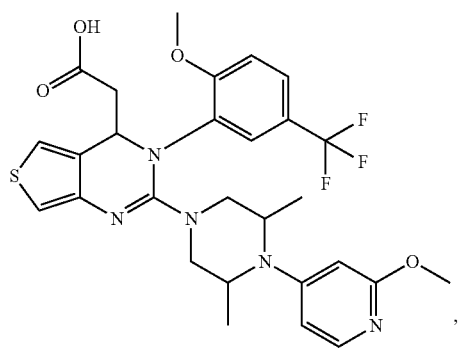
,
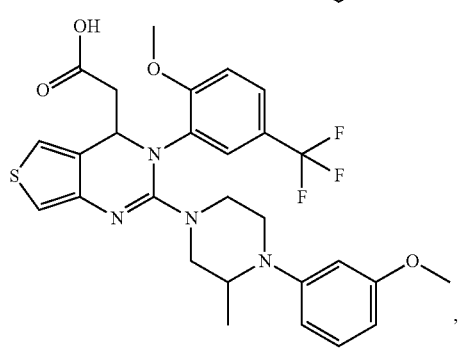
,
120
-continued
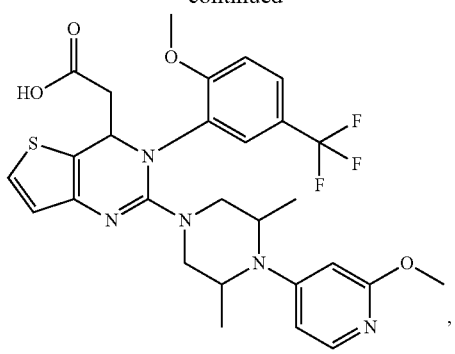
,
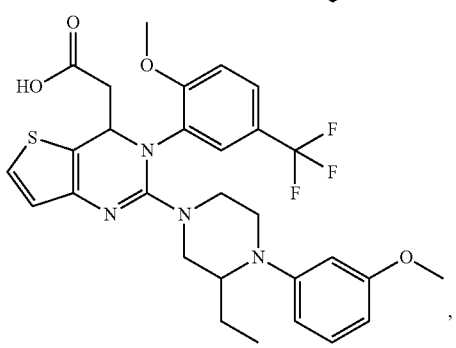
,
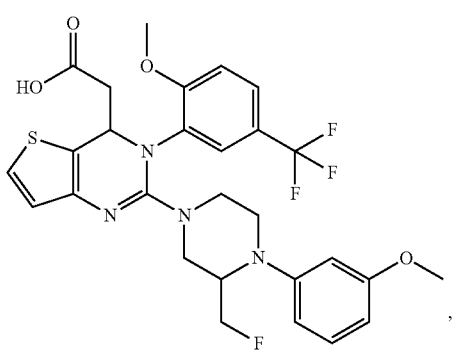
,
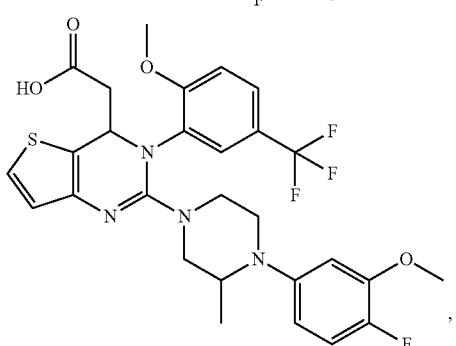
,
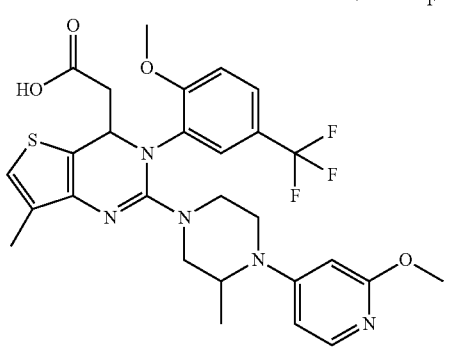
and

121
-continued
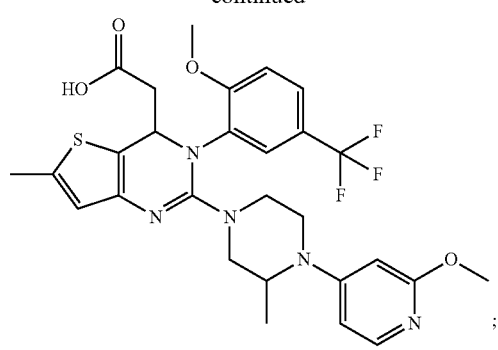
or, is selected from the group consisting of
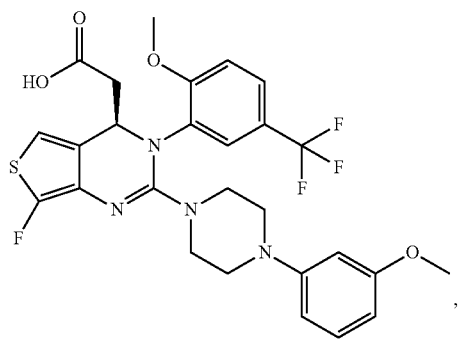
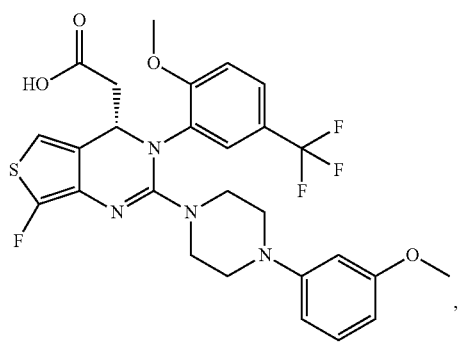
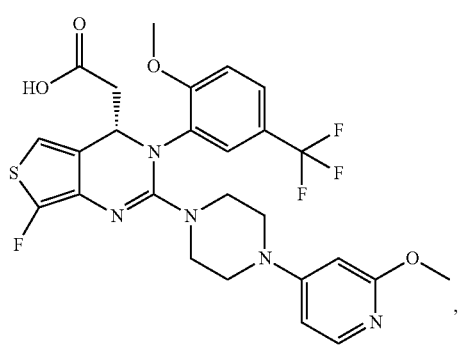
122
-continued
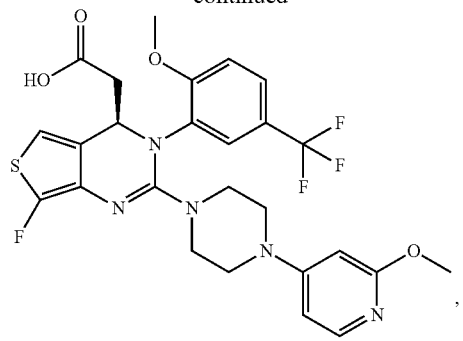
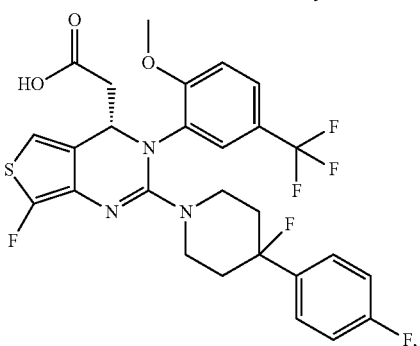
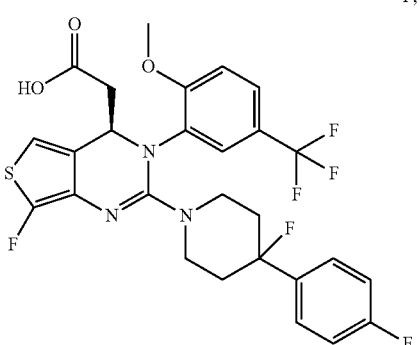
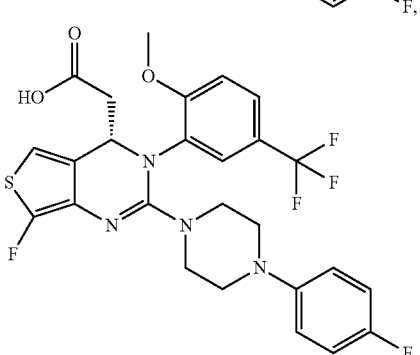
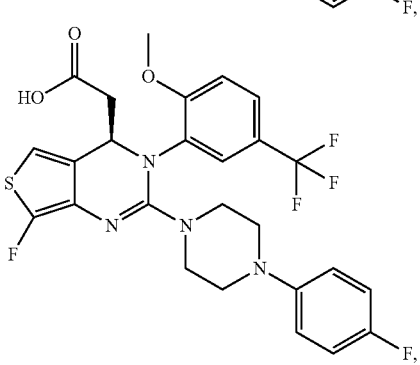

123
-continued
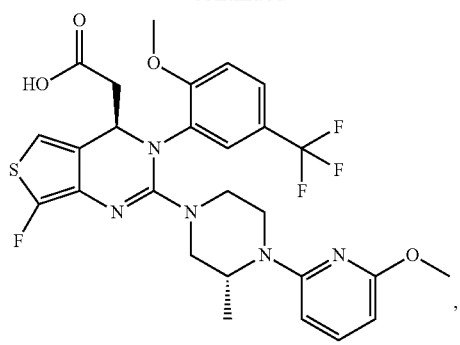
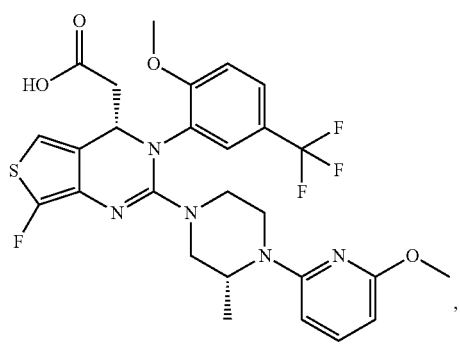
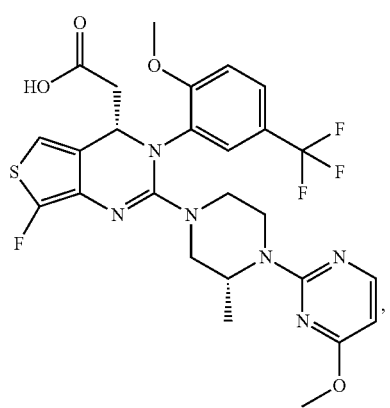
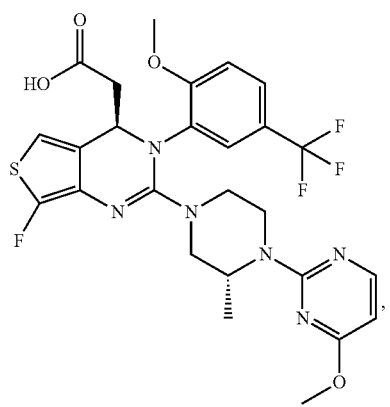
124
-continued
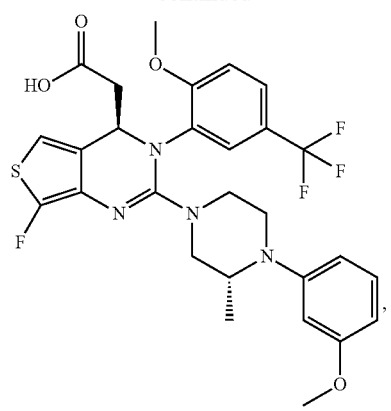
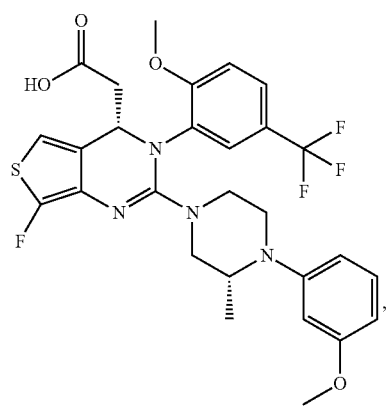
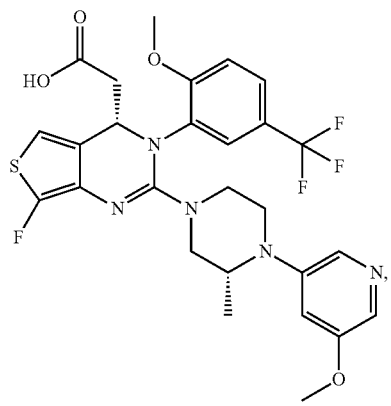
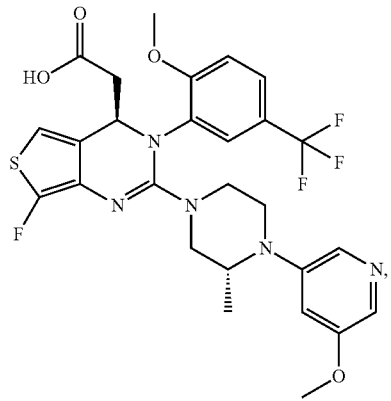

125
-continued
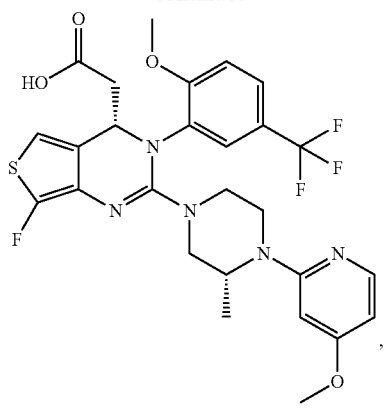
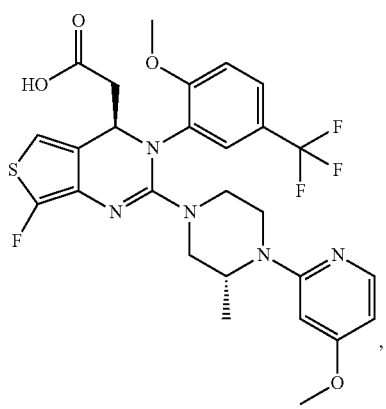
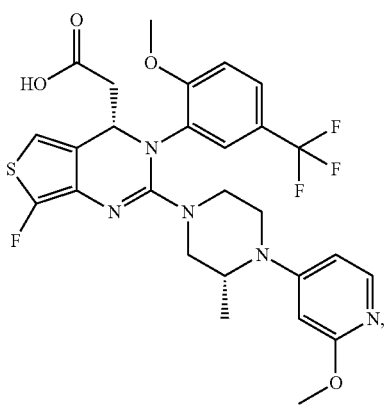
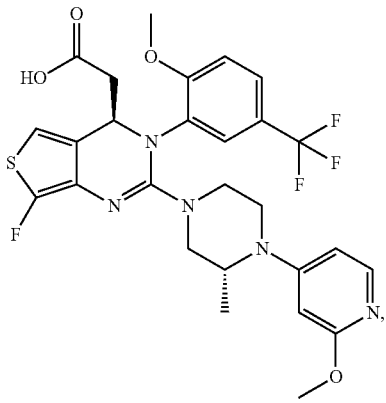
126
-continued
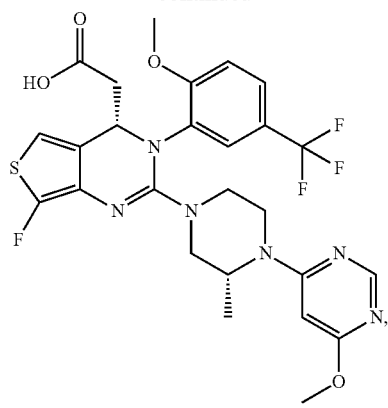
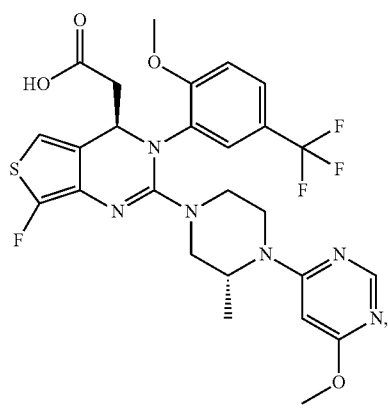
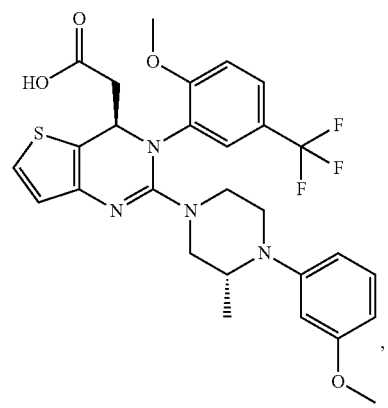
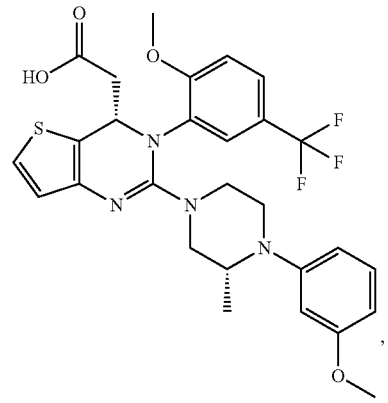

127
-continued
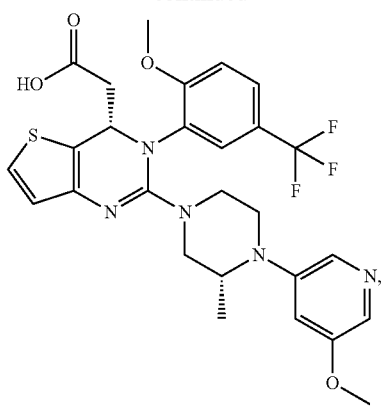
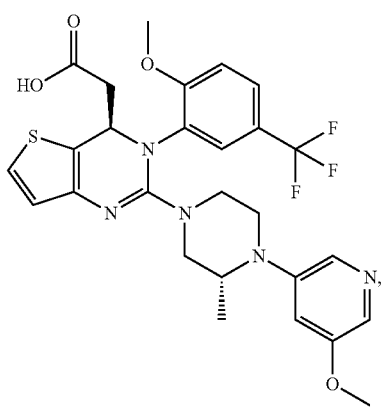
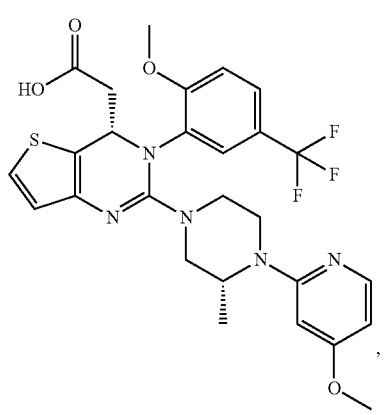
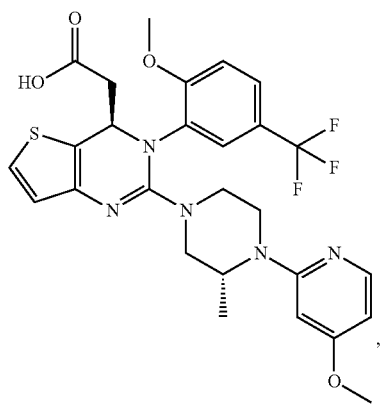
128
-continued
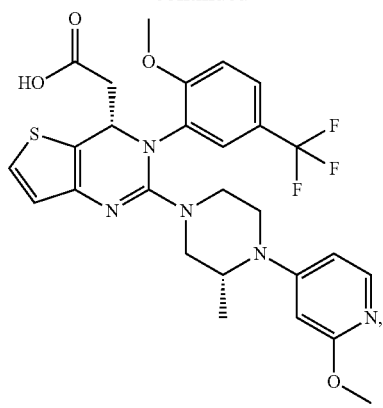
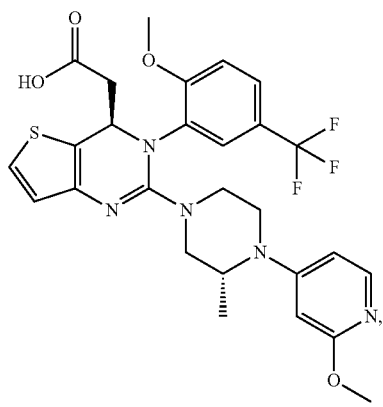
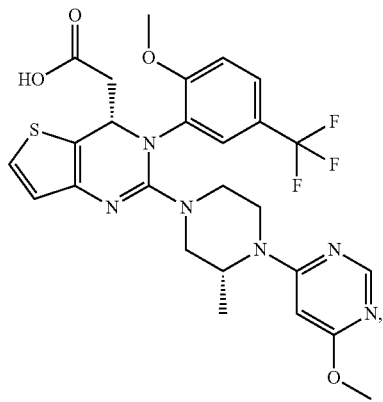
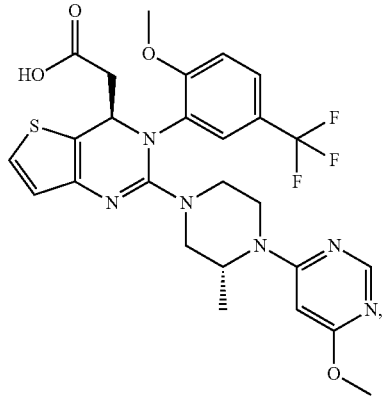

129
-continued
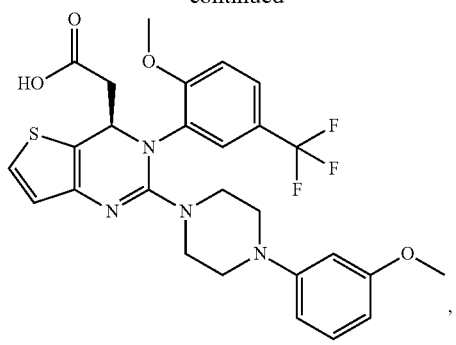
,
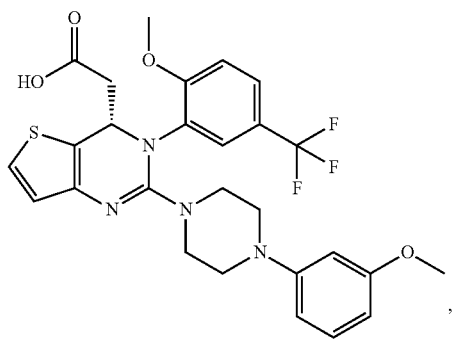
,
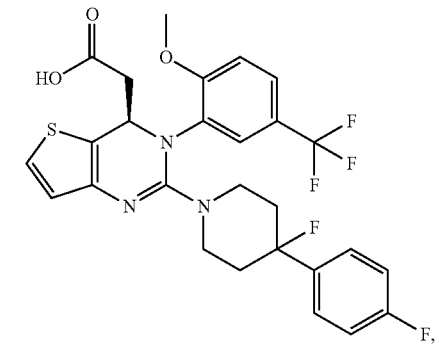
,
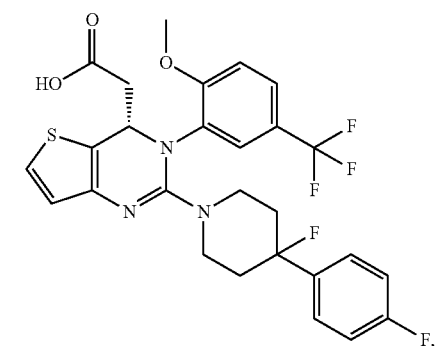
,
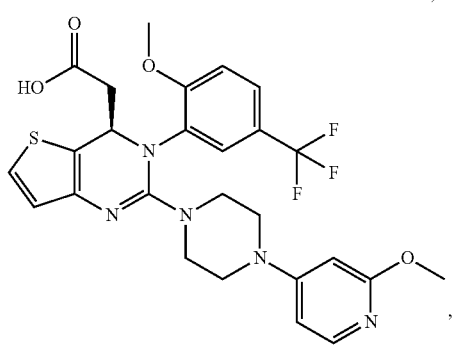
,
130
-continued
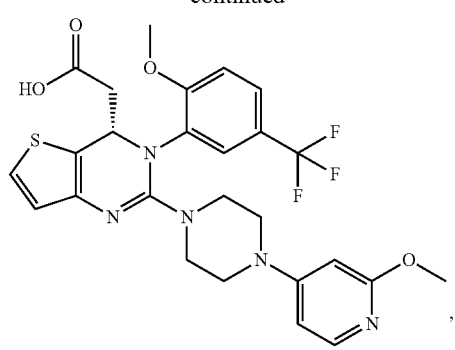
,
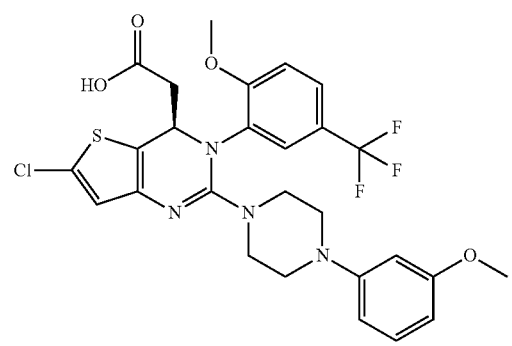
,
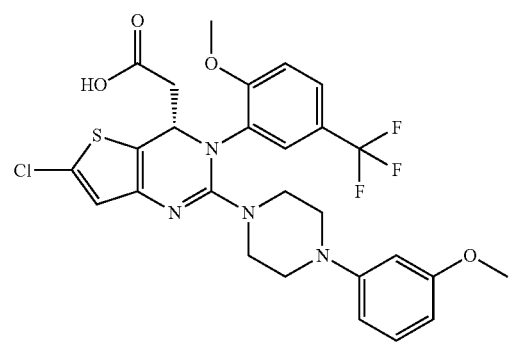
,
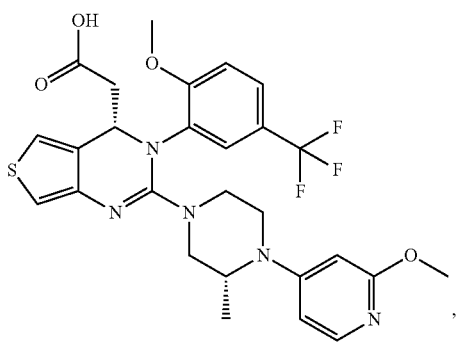
,
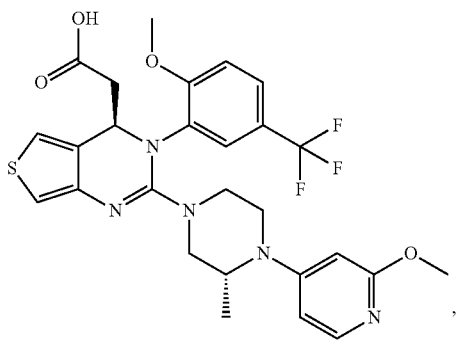
, 131
-continued
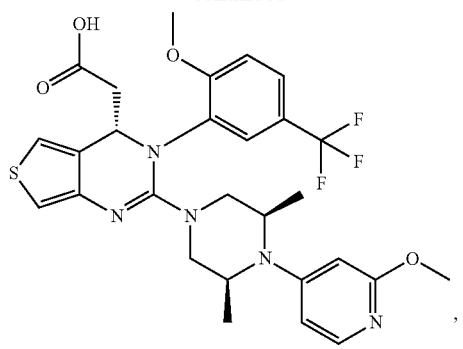
,
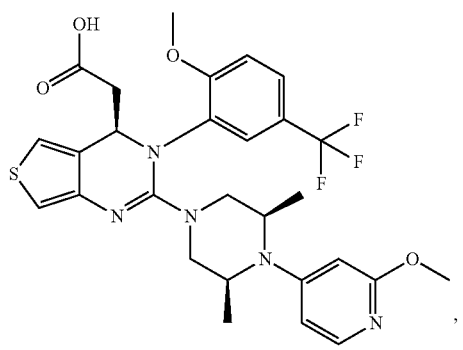
,
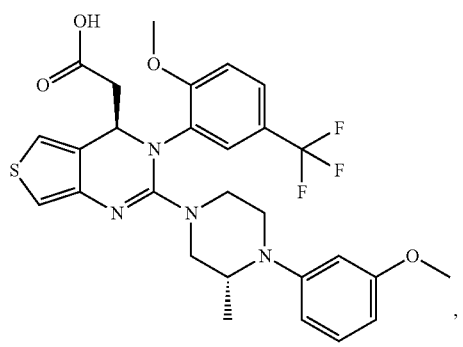
,
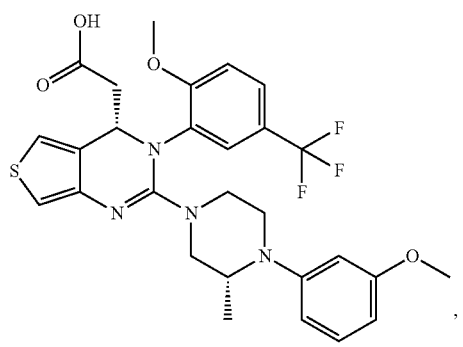
,
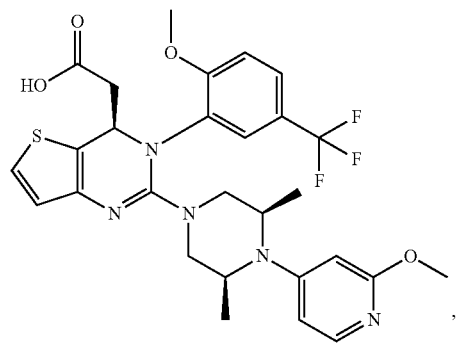
,
132
-continued
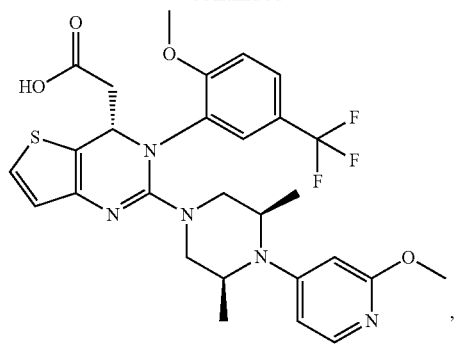
,
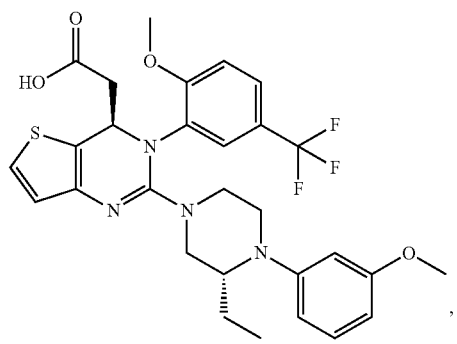
,
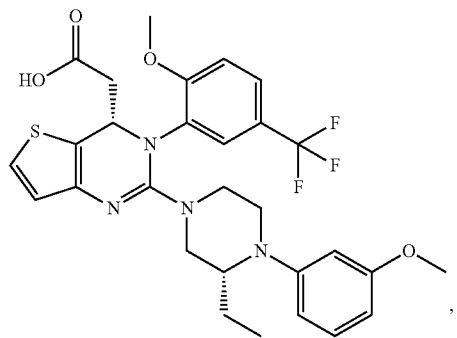
,
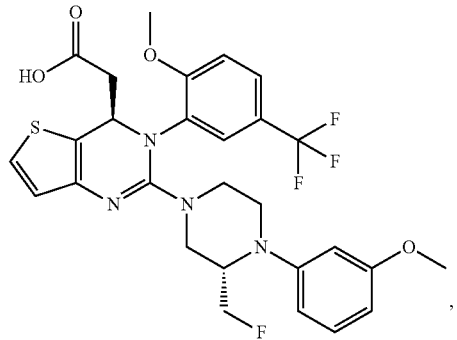
,
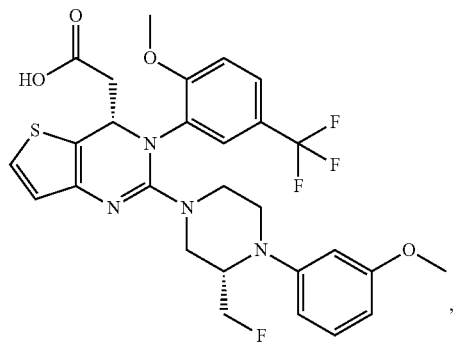
, 133
-continued

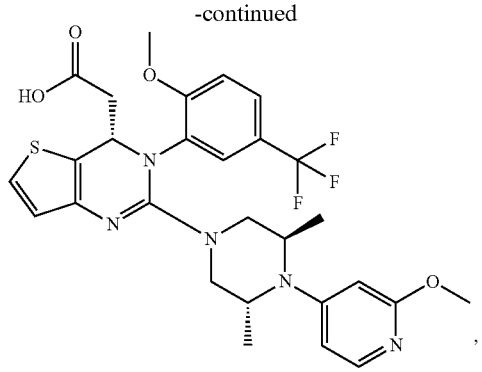
,

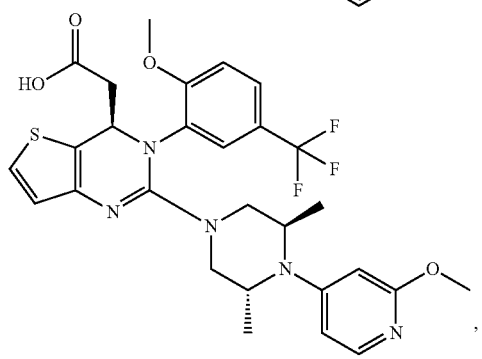
,

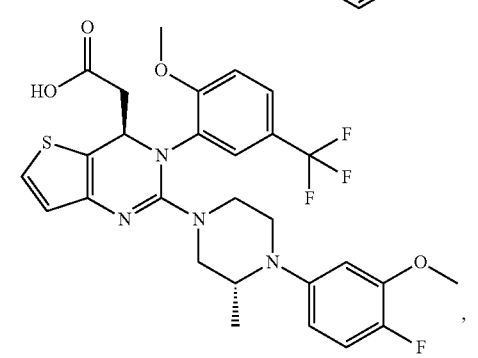
,

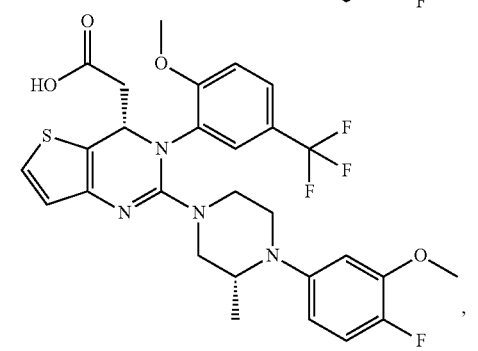
,

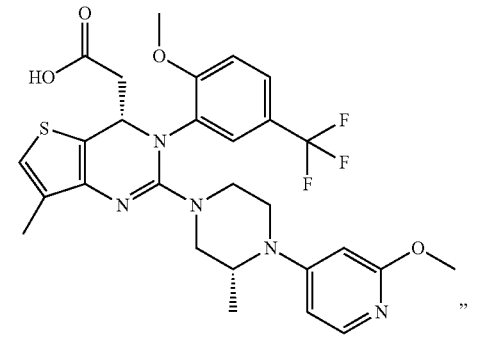
,

134
-continued

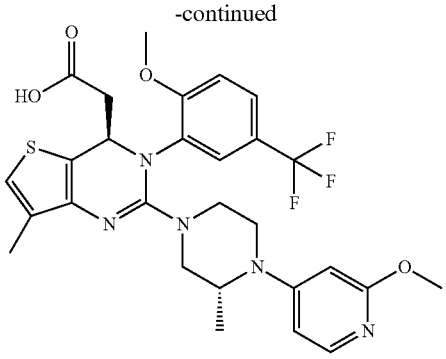
,

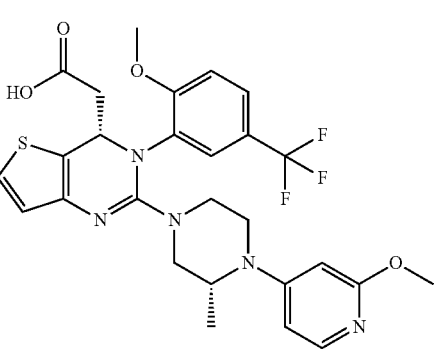
and

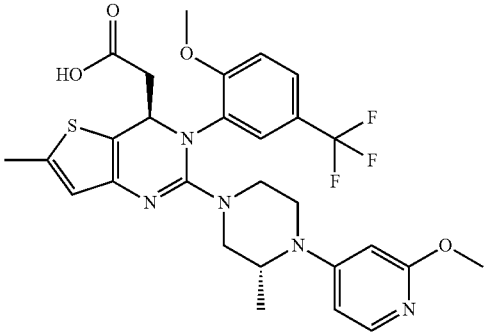
.

22. A pharmaceutical composition, comprising the compound, the pharmaceutically acceptable salt or the tautomer as defined in claim 1, as well as one or more than one pharmaceutically acceptable excipient.

23. A pharmaceutical composition, comprising the compound, the pharmaceutically acceptable salt or the tautomer as defined in claim 21, as well as one or more than one pharmaceutically acceptable excipient.

24. A method for treating a human cytomegalovirus (HCMV) infection in a patient in need thereof, comprising administering to the patient a medicament comprising an effective amount of the compound, the pharmaceutically acceptable salt or the tautomer as defined in claim 1.

25. A method for treating a human cytomegalovirus (HCMV) infection in a patient in need thereof, comprising administering to the patient a medicament comprising an effective amount of the compound, the pharmaceutically acceptable salt or the tautomer as defined in claim 21.

* * * * *